US012076503B2

(12) United States Patent
Krolik et al.

(10) Patent No.: US 12,076,503 B2
(45) Date of Patent: Sep. 3, 2024

(54) TUBULAR STRUCTURES WITH VARIABLE SUPPORT

(71) Applicant: Q'APEL MEDICAL, INC., Fremont, CA (US)

(72) Inventors: Jeffery Krolik, Campbell, CA (US); Rajan Khokhar, Santa Cruz, CA (US)

(73) Assignee: Q'APEL MEDICAL, INC., Fremont, CA (US)

( * ) Notice: Subject to any disclaimer, the term of this patent is extended or adjusted under 35 U.S.C. 154(b) by 0 days.

(21) Appl. No.: 16/323,776

(22) PCT Filed: Jul. 26, 2017

(86) PCT No.: PCT/US2017/044046
§ 371 (c)(1),
(2) Date: Feb. 7, 2019

(87) PCT Pub. No.: WO2018/022813
PCT Pub. Date: Feb. 1, 2018

(65) Prior Publication Data
US 2021/0069466 A1 Mar. 11, 2021

Related U.S. Application Data

(60) Provisional application No. 62/367,634, filed on Jul. 27, 2016.

(51) Int. Cl.
*A61M 25/00* (2006.01)
*A61M 25/01* (2006.01)
(Continued)

(52) U.S. Cl.
CPC .... *A61M 25/0052* (2013.01); *A61M 25/0023* (2013.01); *A61M 25/0053* (2013.01);
(Continued)

(58) Field of Classification Search
CPC .......... A61M 25/0023; A61M 25/0051; A61M 25/0052; A61M 25/0053; A61M 25/005;
(Continued)

(56) References Cited

U.S. PATENT DOCUMENTS

| 4,248,234 A | 2/1981 | Assenza |
| 4,498,473 A | 2/1985 | Gereg |

(Continued)

FOREIGN PATENT DOCUMENTS

| CN | 103476351 A | 12/2013 |
| CN | 103356287 | 11/2016 |

(Continued)

OTHER PUBLICATIONS

Lacken, Alma, International Search Report, Jul. 1, 2016, 10 pages, Australian Patent Office, Woden ACT, Australia.

(Continued)

*Primary Examiner* — Robert J Utama
*Assistant Examiner* — Leah J Swanson
(74) *Attorney, Agent, or Firm* — Wilson Sonsini Goodrich & Rosati

(57) ABSTRACT

A lumenal element configured to transit a body lumen comprising a lumenal member (102) and an outer member (200) disposed over at least part of the lumenal member with a structural support (350), e.g. a mesh or stent, having a facing surface facing a surface of the lumenal member and wherein the facing surface includes at least one non-smooth surface portion, discontinuity, or non-uniformity, wherein the structural support is between the lumenal member and the outer member wherein the outer member is at least partly sealed to adjacent surfaces of the lumenal member sufficient to withstand fluid pressure within a space about the structural support, wherein the lumenal member has a first flexibility in the area of the structural support, and increasing (Continued)

the flexibility of the area of the structural support by moving at least a part of the outer member out of contact with the structural support. The flexibility of a lumenal element can be changed. Also disclosed a method of assembly of the lumenal element.

68 Claims, 28 Drawing Sheets

(51) Int. Cl.
*A61M 25/09* (2006.01)
*A61M 25/06* (2006.01)

(52) U.S. Cl.
CPC ........ *A61M 25/0102* (2013.01); *A61M 25/09* (2013.01); *A61M 2025/0063* (2013.01); *A61M 2025/0687* (2013.01); *A61M 2025/09008* (2013.01)

(58) Field of Classification Search
CPC ...... A61M 2025/0063; A61M 25/0012; A61M 2025/0059; A61M 2025/0024; A61M 2025/0025; A61M 2025/0004
See application file for complete search history.

(56) References Cited

U.S. PATENT DOCUMENTS

| | | | |
|---|---|---|---|
| 4,762,130 A | 8/1988 | Fogarty et al. | |
| 4,796,629 A * | 1/1989 | Grayzel | A61M 25/104 604/103.09 |
| 4,815,450 A | 3/1989 | Patel | |
| 5,176,637 A | 1/1993 | Sagae | |
| 5,328,469 A | 7/1994 | Coletti | |
| 5,337,733 A | 8/1994 | Bauerfeind | |
| 5,378,237 A | 1/1995 | Boussignac | |
| 5,460,608 A * | 10/1995 | Lodin | A61M 25/005 604/103.09 |
| 5,470,322 A | 11/1995 | Horzewski et al. | |
| 5,531,689 A | 7/1996 | Burns et al. | |
| 5,609,583 A | 3/1997 | Hakki | |
| 5,718,861 A | 2/1998 | Andrews et al. | |
| 5,772,681 A | 6/1998 | Leoni | |
| 5,843,120 A | 12/1998 | Israel et al. | |
| 5,897,277 A | 4/1999 | Barre et al. | |
| 6,033,379 A | 3/2000 | Barra | |
| 6,231,598 B1 | 5/2001 | Berry et al. | |
| 6,613,038 B2 | 9/2003 | Bonutti | |
| 6,629,952 B1 | 10/2003 | Chien et al. | |
| 6,786,886 B2 | 9/2004 | Miller et al. | |
| 6,814,715 B2 | 11/2004 | Bonutti | |
| 6,827,710 B1 | 12/2004 | Mooney | |
| 7,645,275 B2 | 1/2010 | O'Connor et al. | |
| 7,695,465 B2 | 4/2010 | Tomaschko et al. | |
| 7,766,896 B2 | 8/2010 | Kornkven Volk et al. | |
| 7,780,692 B2 | 8/2010 | Nance | |
| 7,957,790 B2 | 6/2011 | Kleen | |
| 7,998,132 B2 | 8/2011 | Gregorich et al. | |
| 8,125,755 B2 | 2/2012 | Garcia | |
| 8,303,570 B2 | 11/2012 | Gregorich et al. | |
| 8,488,295 B2 | 7/2013 | Garcia | |
| 8,523,786 B2 | 9/2013 | Van Weymarn-Scharli | |
| 8,556,804 B2 | 10/2013 | Smith et al. | |
| 8,562,517 B2 | 10/2013 | Van Weymarn-Scharli | |
| 8,597,277 B2 | 12/2013 | Lenker | |
| 8,814,848 B2 | 8/2014 | Gregorich et al. | |
| 8,821,478 B2 | 9/2014 | Hanson et al. | |
| 9,155,451 B2 | 10/2015 | Smith et al. | |
| 9,265,526 B1 | 2/2016 | Abdou | |
| 9,370,639 B2 | 6/2016 | Plassman et al. | |
| 9,561,345 B2 | 2/2017 | Garrison et al. | |
| 9,623,206 B2 | 4/2017 | Melsheimer | |
| 9,629,980 B2 | 4/2017 | O'Day | |
| 9,889,273 B2 | 2/2018 | Cully et al. | |
| 10,123,683 B2 | 11/2018 | Smith et al. | |
| 10,441,745 B2 | 10/2019 | Yang et al. | |
| 10,463,427 B2 | 11/2019 | Smith et al. | |
| 10,792,056 B2 | 10/2020 | Vale et al. | |
| 10,806,331 B2 | 10/2020 | Smith et al. | |
| 10,835,112 B2 | 11/2020 | Smith et al. | |
| 10,926,060 B2 | 2/2021 | Stern et al. | |
| 11,123,522 B2 | 9/2021 | Krolik et al. | |
| 11,376,065 B2 | 7/2022 | Smith et al. | |
| 11,382,690 B2 | 7/2022 | Smith et al. | |
| 11,446,469 B2 | 9/2022 | Logan et al. | |
| 2001/0003297 A1 | 6/2001 | Pedersen et al. | |
| 2003/0229296 A1 | 12/2003 | Ishikawa et al. | |
| 2004/0116851 A1 | 6/2004 | Johansen et al. | |
| 2005/0171591 A1 | 8/2005 | McHale et al. | |
| 2006/0069346 A1 | 3/2006 | Smith et al. | |
| 2007/0173921 A1 | 7/2007 | Wholey et al. | |
| 2008/0039691 A1 | 2/2008 | Smith et al. | |
| 2008/0097399 A1 | 4/2008 | Sachar | |
| 2009/0030282 A1 | 1/2009 | Garcia et al. | |
| 2009/0171278 A1 | 7/2009 | Hirszowicz et al. | |
| 2010/0004593 A1 | 1/2010 | Gregorich | |
| 2010/0145265 A1 | 6/2010 | Min et al. | |
| 2011/0034987 A1 | 2/2011 | Kennedy | |
| 2011/0237888 A1 | 9/2011 | Matsushita | |
| 2012/0172964 A1 | 7/2012 | Schneider | |
| 2012/0232479 A1 | 9/2012 | Vo et al. | |
| 2012/0253193 A1 | 10/2012 | Hanson et al. | |
| 2012/0277729 A1 | 11/2012 | Melsheimer | |
| 2013/0030519 A1 | 1/2013 | Tran et al. | |
| 2013/0096535 A1 | 4/2013 | Gregorich et al. | |
| 2013/0282099 A1 | 10/2013 | Huynh | |
| 2013/0289478 A1 | 10/2013 | Kim et al. | |
| 2014/0236120 A1 | 8/2014 | Tsai et al. | |
| 2014/0277384 A1 | 9/2014 | Melsheimer | |
| 2017/0035988 A1 | 2/2017 | Melsheimer et al. | |
| 2017/0136211 A1 | 5/2017 | Arguelle | |
| 2017/0252062 A1 | 9/2017 | Fitterer | |
| 2018/0015257 A1 | 1/2018 | Krolik et al. | |
| 2021/0069466 A1 | 3/2021 | Krolik et al. | |
| 2021/0205586 A1 | 7/2021 | Krolik et al. | |
| 2021/0361910 A1 | 11/2021 | Mullins et al. | |
| 2022/0233814 A1 | 7/2022 | Mullins et al. | |
| 2022/0361946 A1 | 11/2022 | Smith et al. | |
| 2022/0379078 A1 | 12/2022 | Logan et al. | |
| 2023/0338049 A1 | 10/2023 | Jalgaonkar et al. | |

FOREIGN PATENT DOCUMENTS

| | | | |
|---|---|---|---|
| DE | 19729499 | | 1/1999 |
| EP | 0761252 A1 | | 3/1997 |
| EP | 1839591 B1 | | 12/2009 |
| EP | 1894594 | | 12/2009 |
| EP | 2248483 | | 11/2010 |
| EP | 3723821 B1 | | 9/2021 |
| EP | 3986519 A1 | | 4/2022 |
| EP | 2739217 B1 | | 7/2022 |
| EP | 4203815 A1 | | 7/2023 |
| JP | 63192457 | | 8/1988 |
| JP | 2006509597 | | 3/2006 |
| JP | 2011505918 | | 3/2011 |
| JP | 2011-250963 | | 12/2011 |
| JP | 2016-510647 | | 4/2016 |
| WO | WO1996013303 | | 5/1996 |
| WO | WO1998030269 | | 7/1998 |
| WO | WO 1999/015108 A2 | | 4/1999 |
| WO | WO 2004/060434 A2 | | 7/2004 |
| WO | WO 2007/022383 | | 2/2007 |
| WO | WO 2007/028058 | | 3/2007 |
| WO | WO 2007/051183 A1 | | 5/2007 |
| WO | WO 2008/142685 A2 | | 11/2008 |
| WO | WO 2009/076224 | | 6/2009 |
| WO | WO 2011/011765 A2 | | 1/2011 |
| WO | WO 2011/017189 A1 | | 2/2011 |
| WO | WO 2012/071105 | | 5/2012 |
| WO | WO 2012/112949 | | 8/2012 |
| WO | WO 2014/150403 A1 | | 9/2014 |
| WO | WO 2016/118671 | | 7/2016 |
| WO | WO-2016204759 A1 * | 12/2016 | ............ A61B 8/481 |

(56) References Cited

FOREIGN PATENT DOCUMENTS

| WO | WO 2018/022813 | 2/2018 |
|---|---|---|
| WO | WO-2020254447 A1 | 12/2020 |
| WO | WO-2023168415 A1 | 9/2023 |

OTHER PUBLICATIONS

Lacken, Alma, Written Opinion of International Search Authority, Jul. 1, 2016, 18 pages, Australian Patent Office, Woden ACT, Australia.
Ochsenbein, Simon, International Search Report, Nov. 16, 2017, 9 pages, Australian Patent Office, Woden ACT, Australia.
Ochsenbein, Simon, Written Opinion of the International Searching Authority, Nov. 16, 2017, 9 pages, Australian Patent Office, Woden ACT, Australia.
Amaro, Henrique, Extended European Search Report, Aug. 16, 2018, 5 pages, European Patent Office, Munich, Germany.
Bielsa, David, Extended European Search Report, Mar. 5, 2020, 8 pages, European Patent Office, Munich, Germany.
Kawashima, Toru, Notice of Reasons for Rejection, Dec. 3, 2019, Japan Patent Office, Tokyo, Japan.
Amaro, Henrique, Extended European Search Report, Aug. 2, 2019, 4 pages, European Patent Office, Munich, Germany.
Office Action, China Application No. 201680016802.9, Nov. 4, 2019, 9 Pages, National Intellectual Property Administration, P. R. China.
Search Report, China Application No. 201680016802.9, Oct. 25, 2019, 2 Pages, National Intellectual Property Administration, P. R. China.
Reed, Richard, Full Examination Report, No. 2016209354, Oct. 24, 2019, 6 pages, IP Australia, Sydney Australia.
Reed, Richard, Second Examination Report, No. 2016209354, Oct. 22, 2020, 8 pages, IP Australia, Sydney Australia.
Reed, Richard, Third Examination Report, No. 2016209354, Oct. 22, 2020, 4 pages, IP Australia, Sydney Australia.
Reed, Richard, Acceptance, No. 2016209354, Oct. 26, 2020, 4 pages, IP Australia, Sydney Australia.
U.S. Appl. No. 15/545,309 Office Action dated Apr. 6, 2020.
U.S. Appl. No. 15/545,309 Office Action dated Dec. 15, 2020.
U.S. Appl. No. 15/545,309 Office Action dated Jan. 22, 2024.
U.S. Appl. No. 15/545,309 Office Action dated Mar. 10, 2022.
U.S. Appl. No. 15/545,309 Office Action dated Nov. 29, 2022.
U.S. Appl. No. 17/209,167 Office Action dated May 24, 2021.

\* cited by examiner

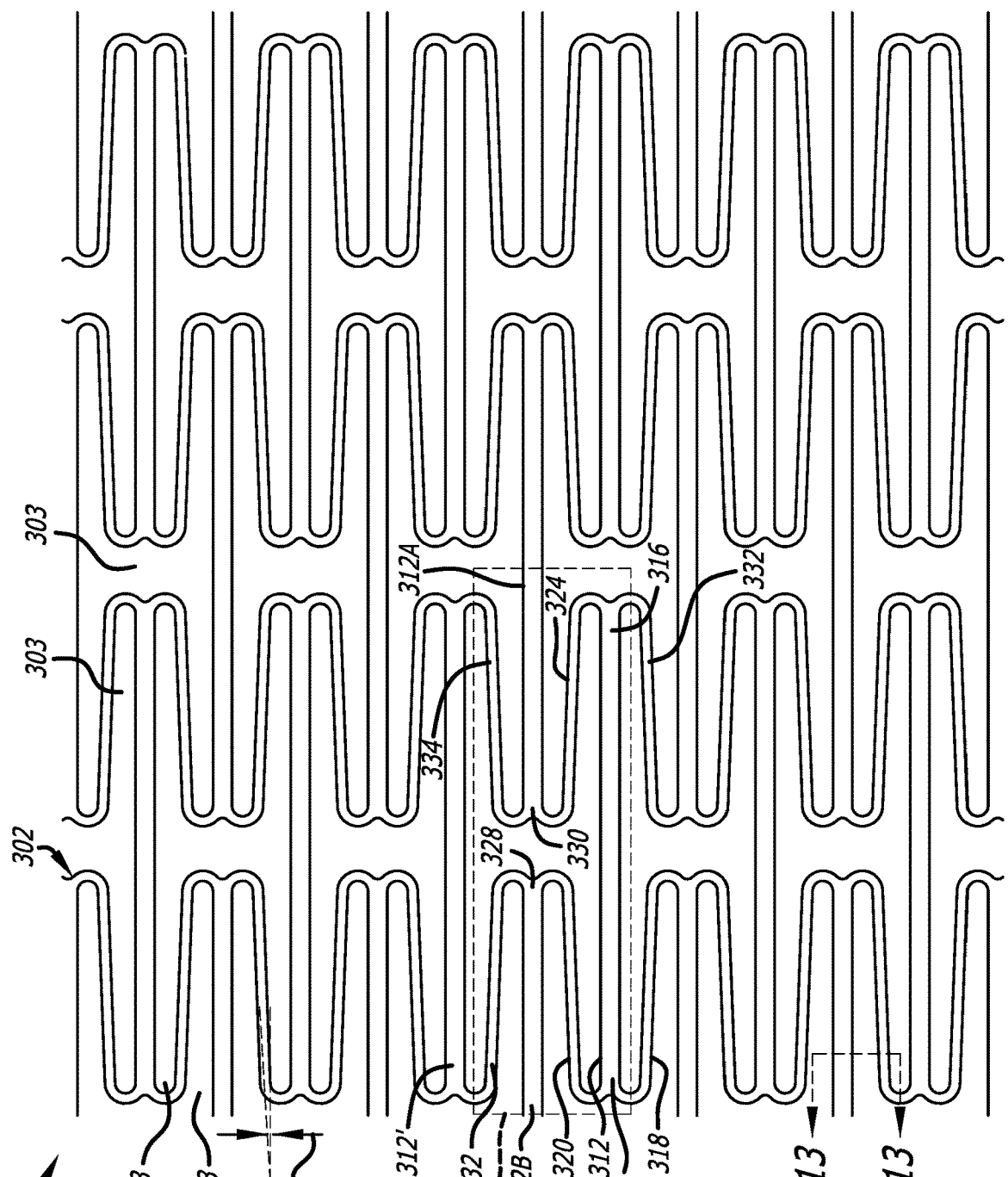
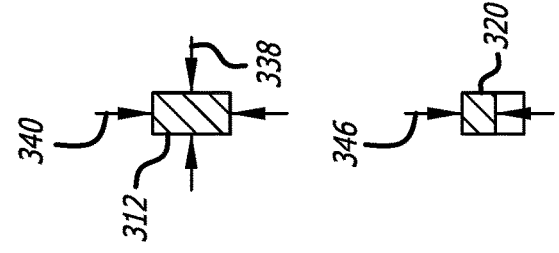
FIG. 12
FIG. 13

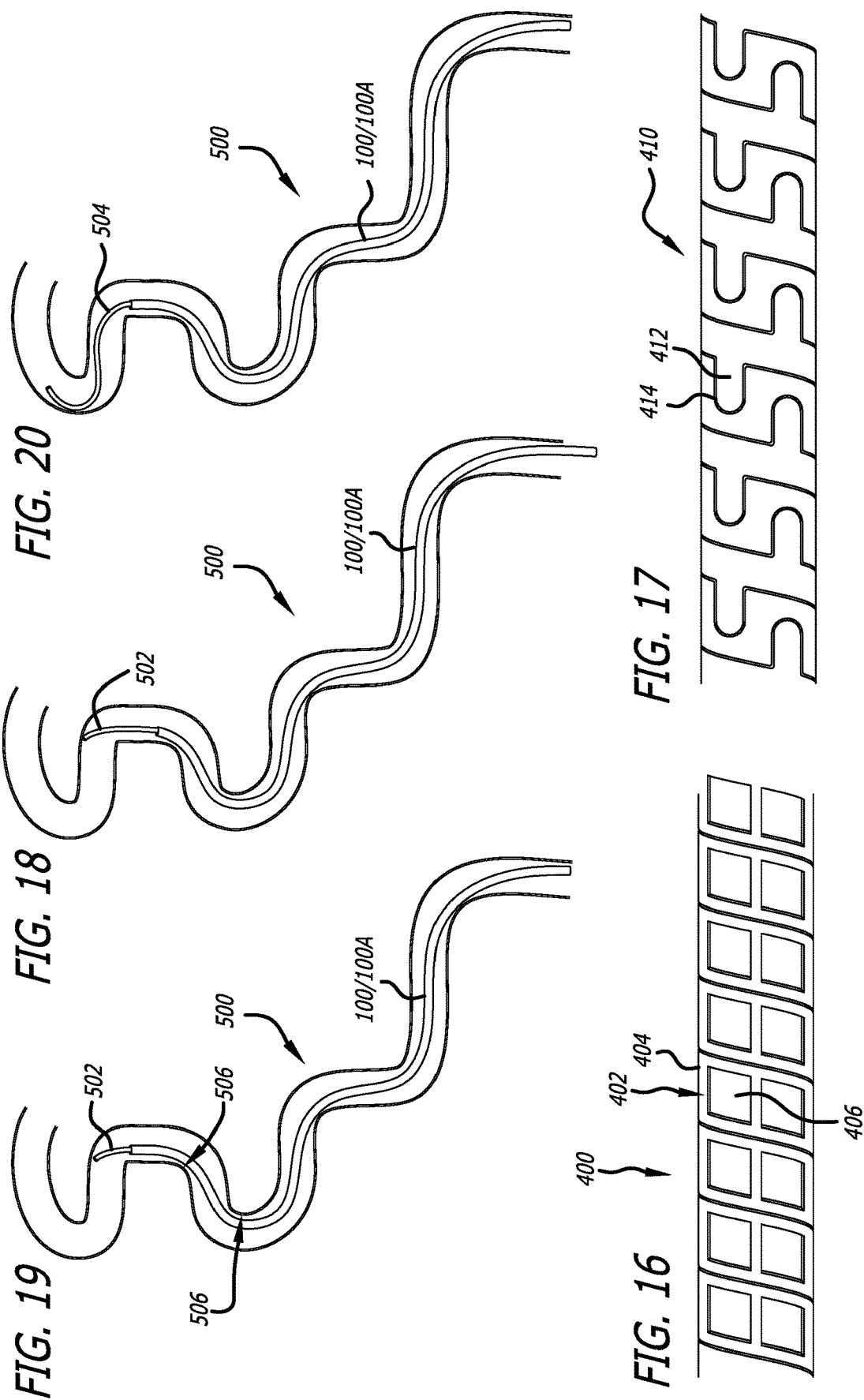

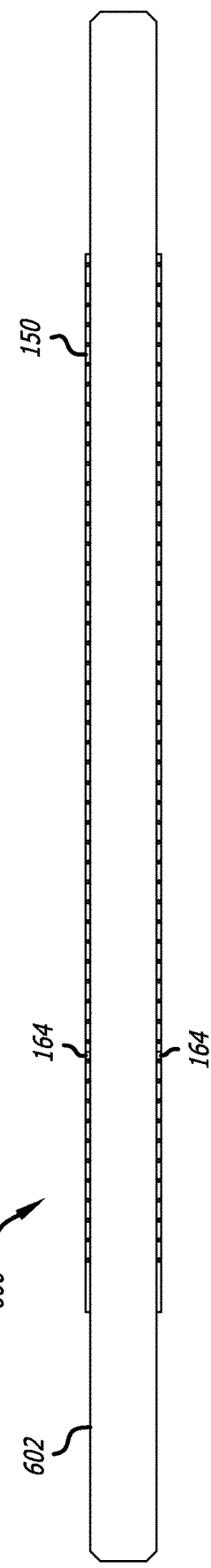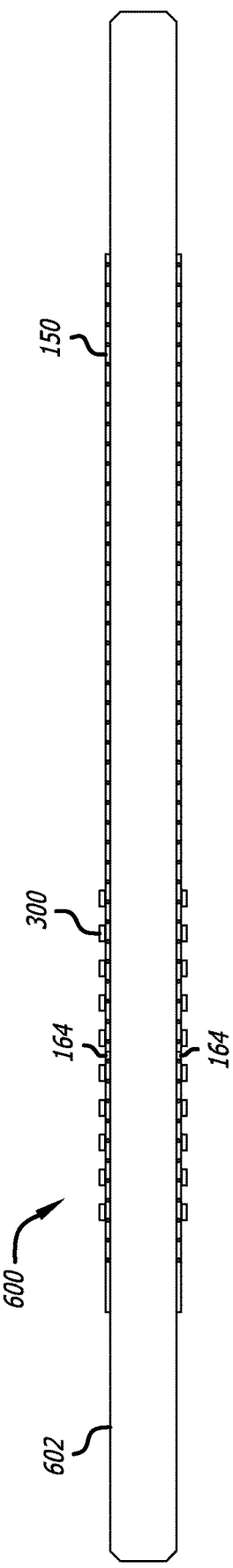

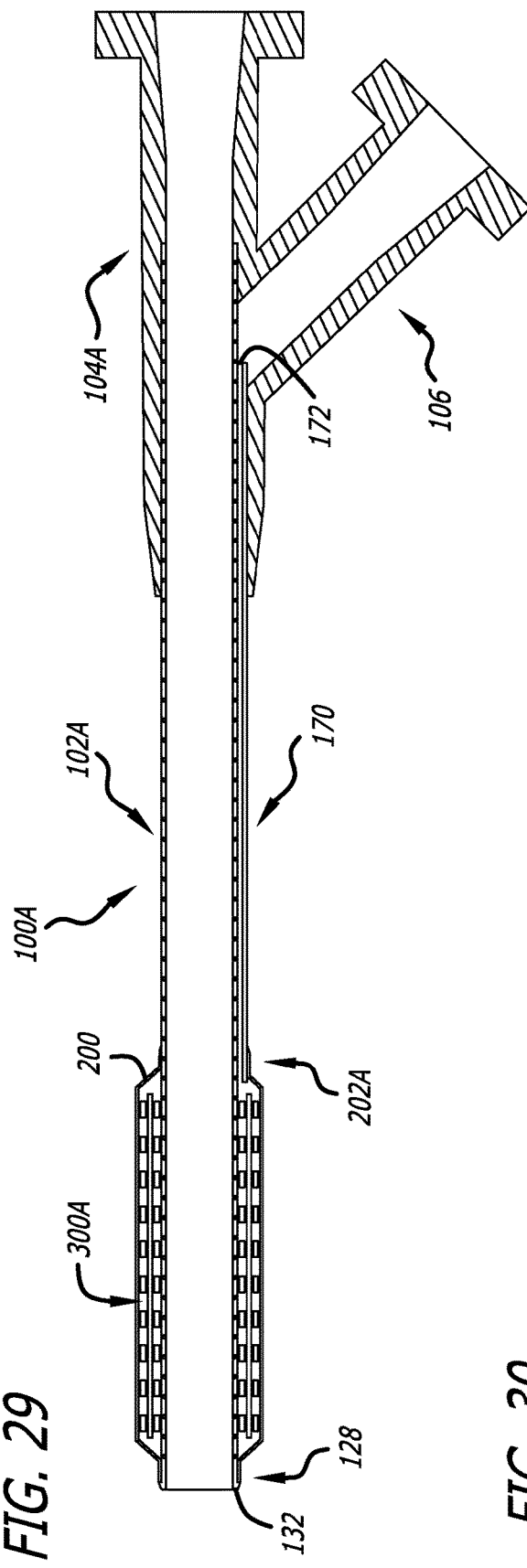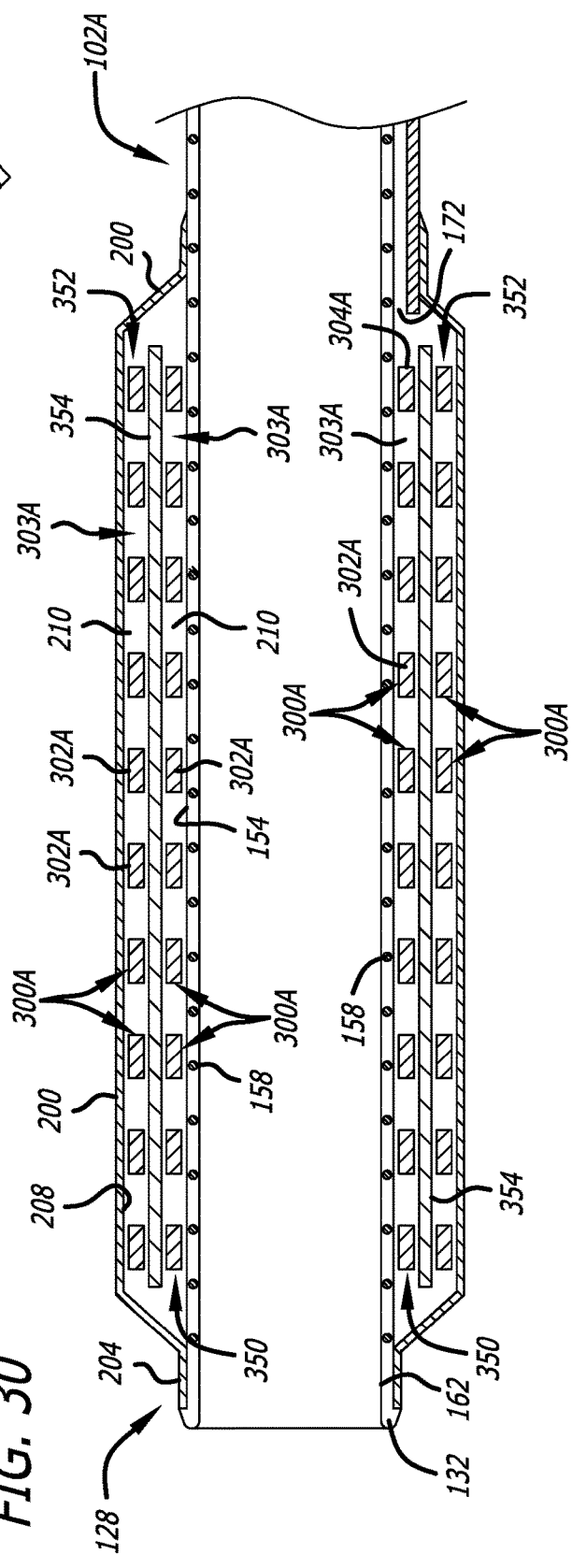

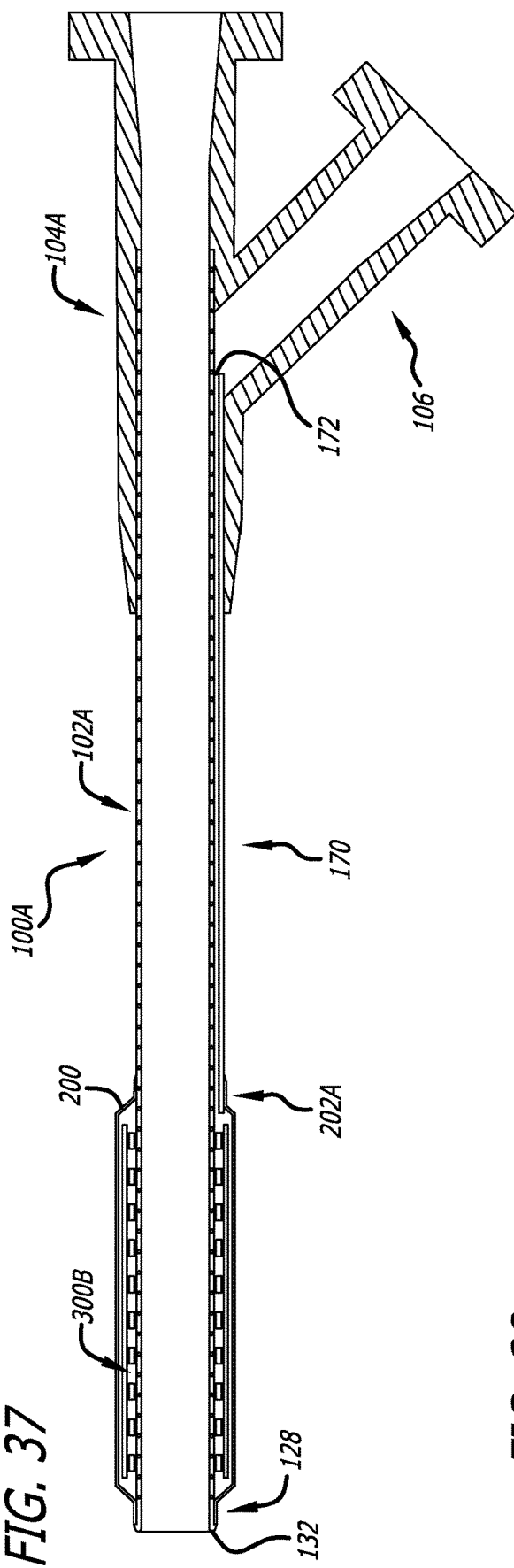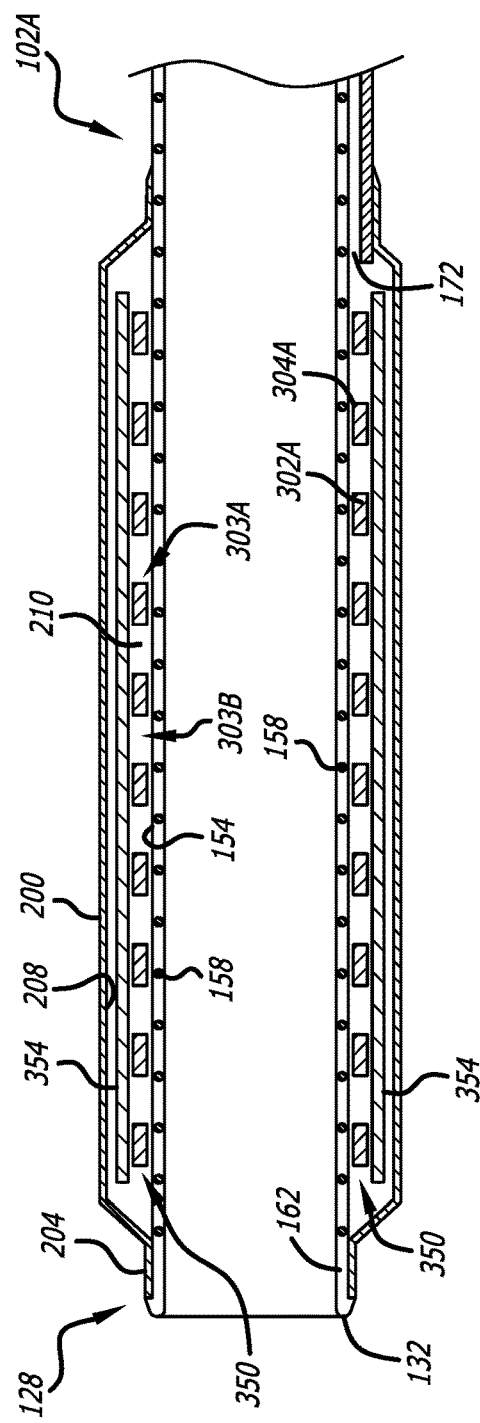
FIG. 37
FIG. 38

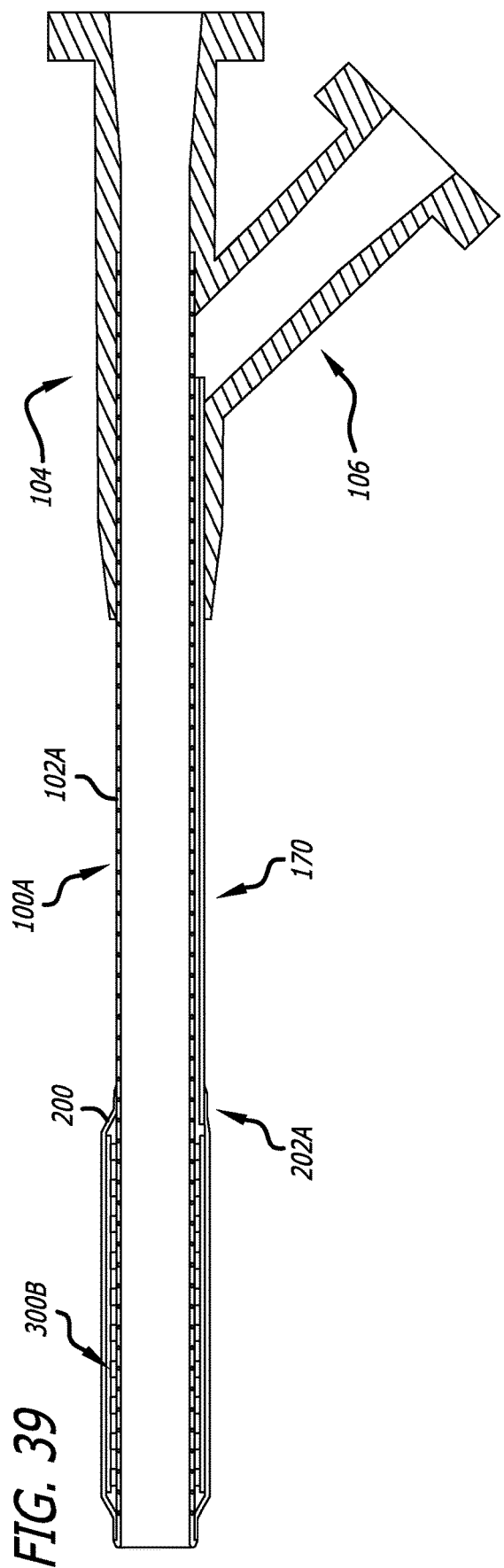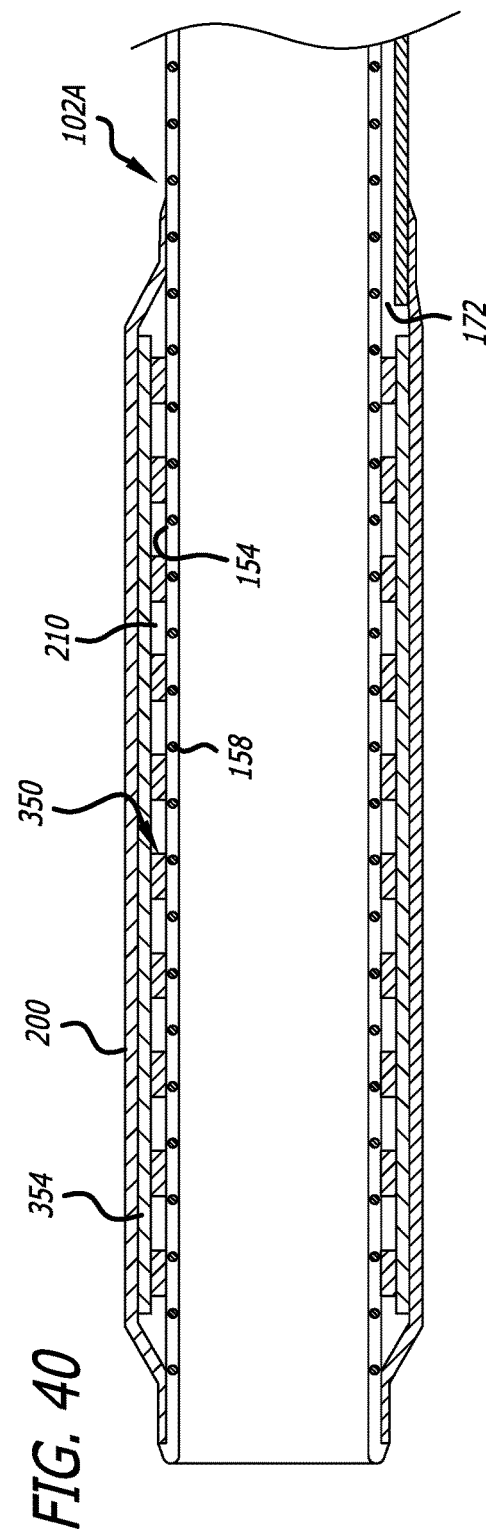

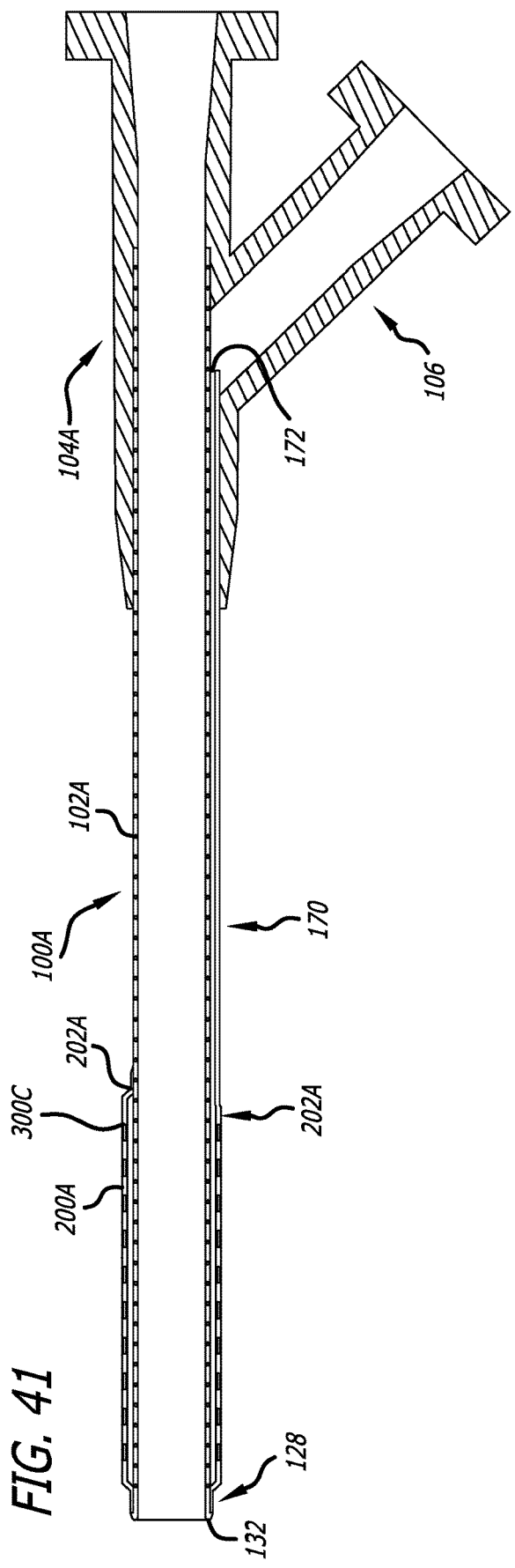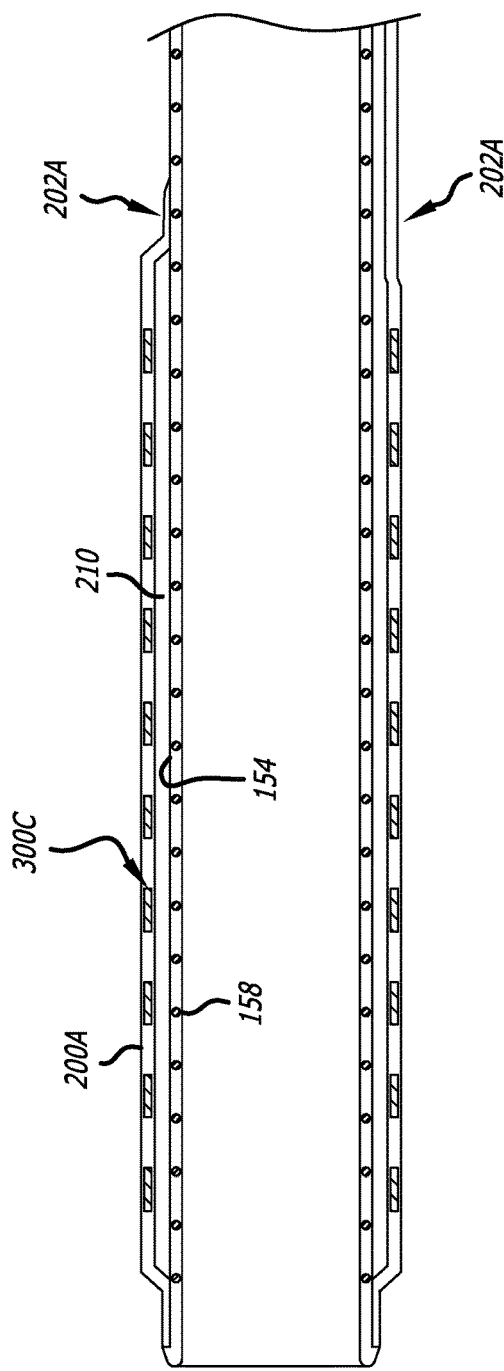

TUBULAR STRUCTURES WITH VARIABLE SUPPORT

CROSS REFERENCE TO RELATED APPLICATIONS

This application is a National Stage of International Application No. PCT/US17/44046, filed Jul. 26, 2017, which claims priority from U.S. 62/367,634 filed Jul. 27, 2016, the entire contents of which are incorporated herein by reference.

BACKGROUND

These inventions relate to flexible shafts, including shafts having lumens and to shafts tubular structures, including both of those that may be suitable for transiting mammalian lumens, including vasculature and other lumens, including for humans, to such structures having variable support, and to catheters.

SUMMARY

In one example of lumenal members, a flexible lumenal member includes an inner member and has an outer member outside of the inner member. A medial member is between the inner and outer members, wherein the outer member is collapsible about the medial member and wherein the outer member and the medial member are configured such that collapse of the outer member about the medial member increases a stiffness of the assembly by contact between a surface or surfaces of the medial member with a surface or surfaces of an adjacent member or members. The medial member may be a support structure or an assembly of elements including a support structure, where the support structure has a surface or surfaces that may include surface discontinuities, in one example in the form of raised structures or cavities forming surface discontinuities, and such surface discontinuities may increase a frictional engagement between the medial member and an adjacent surface when they come into contact. In one example, the support structure is a mesh or stent, including any of the stent or stent-like structures described herein, or any other support structures or similar structures as those described herein. In an example where a medial member extends longitudinally and the support structure has an inside surface having surface discontinuities, an inside dimension of the support structure spanning the interior of the support structure may vary longitudinally, for example as a function of the variations in the surface discontinuities, and also may vary arcuately or rotationally around the interior of the support structure at any given longitudinal position. For example, where the surface discontinuities are formed by raised structures, the spacing across the interior of the support structure from a raised structure to a surface on the opposite side may be a first distance and the spacing across the interior of the support structure from a point adjacent a raised structure to a surface on the opposite side may be a second distance greater than the first distance. Where the support structure forms a right circular cylinder, the distances would be equivalent to the inside diameters. In an example where a support structure extends longitudinally and has an outside surface having surface discontinuities, an outside dimension of the support structure spanning the support structure may vary longitudinally, for example as a function of the variations in the surface discontinuities, and also may vary arcuately or rotationally around the exterior of the support structure at any given longitudinal position. For example, where the surface discontinuities are formed by raised structures, the spacing from an outer surface of the raised structure to the opposite side of the support structure may be a first distance and the spacing from an outer surface adjacent the raised structure to the opposite side of the support structure may be a second distance less than the first distance. Where the support structure forming at least part of the medial member forms a right circular cylinder, the distances would be equivalent to outside diameters. Medial members forming or incorporating support structures as described in this paragraph and medial members forming or incorporating support structures such as described elsewhere herein can be used in any of the assemblies described herein.

In an example of a support structure such as one that may be used as or with a medial member in any of the assemblies described herein, the support structure may be in the form of a stent, stent-like structure or mesh structure, including any of those described herein or similar thereto, and may include on at least one surface of the support structure a raised structure, for example a raised structure extending outward relative to the at least one surface of the support structure. In one example, a raised structure can extend away from the adjacent surface, or a raised structure can be formed as a structure adjacent one or more cavities in material adjacent the raised structure. In an example, a support structure, for example a stent, in one example a stent around a portion of an inner tubular structure and within an outer tubular member (including any of those described herein), includes a plurality of limbs wherein at least one limb includes at least one raised structure extending toward an interior of the support structure. The limb has a thickness, and the raised structure extends a distance less than the thickness of the limb. The limb has a surface area, and a surface area of the raised structure is less than the surface area of the limb. In one example, the limb includes a plurality of raised structures. In a further example, the support structure includes a plurality of limbs, and at least some of the plurality of limbs includes respective raised structures. When the support structure is included around a portion of an inner tubular structure, any raised structures can contact respective adjacent surfaces on the inner tubular structure, and such contact can resist movement or geometry changes of an assembly in which the support structure is included. In other examples of support structures described herein, the surface geometries facing the adjacent surfaces on the inner tubular structure or the outer tubular member can be uniformly smooth or without surface discontinuities or without surface variations.

In one configuration, the inner member includes a lumen, for example which can receive a component, including but not limited to a guidewire, dilator, therapeutic device, intervention device and/or other components. In that or another configuration, the medial member can take a number of configurations. In one example of a configuration of the medial member, the medial member can be a stent, for example a stent that is generally understood in the medical industry as being for implanting into a body, or the medial member can be a skeleton or movable support structure for example that may be bendable, flexible or otherwise movable, including skeletons or movable support structures having linear or curving segments separated by open spaces. The linear and/or curving segments can have a repeating pattern or a non-repeating pattern. In any of the foregoing or additional configurations, the medial member may be enclosed within an envelope, for example one which prevents contact between the medial member and vasculature into which the assembly can be inserted. In one configuration, the medial member may be sealed within a cavity, in one example an annular cavity, and in another configuration, the medial member may be enclosed within a cavity that is fully sealed or closed but for one or more fluid passageways for allowing fluid to enter and exit the cavity.

In another example of lumenal members, including any of the foregoing examples and configurations, a flexible lumenal member includes an inner member, over a portion of which an intermediate structural member extends. An outer member extends over at least part, and in the present examples all, of the intermediate structural member. In a relaxed state of the flexible lumenal member, the intermediate structural member and the outer member, the intermediate structural member has a first outer dimension, in at least some examples an outer diameter, and the outer member has at least one second inner dimension, in at least some examples an inner diameter, less than the first outer dimension of the structural member. In such a configuration, the outer member may be biasing or pressing against the intermediate structural member toward the inner member. For example, the outer member can have an uninflated or unexpanded configuration that presses against the intermediate structural member. In one configuration, the unassembled outer member in a relaxed configuration has an inner diameter that is less than the outer diameter of the intermediate structural member in the configuration of the intermediate structural member when it is positioned on the inner member. In one example where the unassembled outer member has an inner diameter less than the outer diameter of the intermediate structural member when the outer member is in a relaxed configuration, the outer member can be expanded or enlarged sufficiently to slide over the intermediate structural member and positioned as desired, and then released, in which case the outer member returns toward the relaxed configuration, pressing on the intermediate structural member. For example, the outer member is resiliently flexible. The intermediate structural member, either alone or with the inner member, stops the further relaxation of the outer member. With the final assembly, and when the apparatus is ready for use, the intermediate structural member is under compression from the resiliency of the outer member.

In another example of a lumenal structure, a lumenal element or a tubular element may combine with one or more additional elements to form a nested structure, at least two components of which may be concentric, at least two components of which may be tubular, and in which one or more structural support elements may be positioned intermediate the lumenal or tubular element and an outer element. In one configuration of the structural support element, the structural support element has a skeleton or framework configuration, for example a plurality of interconnected straight or curved elements separated by open spaces. In one example, a plurality of interconnected straight or curved elements can be highly interconnected, or sparsely interconnected or in between. The straight or curved elements can be struts, each one of which can be interconnected at respective ends with one or more other struts, at nodes. A node can have two struts, thereby contributing to a more sparsely interconnected structure, three struts thereby contributing to a greater interconnected structure, four struts contributing toward a greater interconnected structure, and so on. Similarly, all nodes can have the same number of struts, or there can be groups of nodes having different numbers of struts where a given group has the same number of nodes, which also contributes to the level of interconnectedness. The structural support element can have articulating members, and/or may include a cellular structure interconnected by one or more links, for example struts. In a number of examples, the structural support element can be a stent, for example a stent that is generally understood in the medical industry as being for implanting into a body, for any of a number of procedures. The stent can be an open cell stent, closed cell stent, hybrid cell stent, slotted tube stent, or other stent configuration, including mesh tubes generally. Examples of a stent include the flexible-expandable stent configurations shown in U.S. Pat. No. 5,843,120. The structural support element is flexible, and returnable to its original form without losing substantially the original form. It may also be collapsible and expandable without losing substantially the original form.

In any of the examples of an intermediate structural member described herein, the intermediate structural member can be positioned within an enclosure, for example an outer tubular element, which enclosure is secured to an inner lumenal element or tubular element such that the intermediate structural member is between the enclosure and the inner lumenal element or inner tubular element. The enclosure may be sealed while still permitting fluid communication with a source of pressurized fluid to enlarge or inflate, for example with a liquid or a gas, the enclosure. In one example, the enlargement occurs by way of expansion of the enclosure in the form of an outer cover, for example an outer tubular element. In some examples, the enlargement releases the intermediate structural member, allowing it to move more freely.

In any of the examples of the intermediate structural members, medial structural members, stents or tubular meshes referenced herein, such structural member can include inner and/or outer peripheral surfaces that can frictionally engage adjacent surfaces of the assembly. For example, with a structural member extending between an inner tubular element and an outer tubular element, the surfaces of the structural member contacting one or the other of the inner tubular element and the outer tubular element can press sufficiently into the surface or surfaces to help limit relative movement therebetween. In some configurations, surfaces on the structural member can be sufficiently well-defined to have a perceptible angle or non-round surface that can help to limit relative movement between the structural member and the adjacent tubular member. In other configurations, a surface finish on the structural member can help to increase the frictional force required to move the structural member and the adjacent contacting surface or surfaces relative to each other. Such structural members can be metal, including but not limited to nitinol, stainless steel and similar metals, polished or unpolished, or other materials.

In a further example, which may be configured with any of the foregoing examples or configurations, the examples of intermediate structural members may be used in a variable stiffness catheter. In one example, the catheter has a first flexibility in one condition and a second flexibility in a second condition. The one condition can be an inflated outer envelope, outer tube or outer element around a structural support element, which structural support element is on a lumenal element of the catheter. The outer element is enlarged or inflated to allow an increased flexibility in the catheter. The outer element can be enlarged or inflated an amount sufficient to reduce a surface area of contact between the outer element and the structural support element, which may leave a surface area of contact between the outer element and the structural support element of anywhere from 95% to zero. A reduced surface area of contact can result in greater flexibility of at least a portion of the lumenal element, in the present example the catheter. Reduced or zero surface area of contact between the structural support element and the outer element increases the freedom of movement of the catheter in the area of the structural support element, for example so that any contribution of frictional engagement between the structural support element and the outer element is reduced or eliminated, with the remaining resistance to movement being contributed by the structural support element itself, the inner lumenal element and any surface area of contact between the two of them. If the outer element is constricted, reduced, deflated or otherwise brought into greater contact with the structural support element (for example by withdrawing fluid or by otherwise applying vacuum or negative pressure or by elastic tension in the outer element), flexibility of at least a portion of the lumenal element, the catheter in this example, is reduced, for example arising from greater frictional contact between the outer element and the adjacent surface or surfaces of the structural support element. In one configuration of the foregoing, enlargement or inflation of the outer element occurs by injection or intrusion of a media, for example a fluid, for example a liquid such as saline, into the area of the structural support element. The fluid pressure can be used to increase or enlarge the outer element for example increasing the outer dimension of the outer element so that the inner surface of the outer element no longer contacts one or more adjacent surfaces of the structural support element. In one example, the outer element is enlarged or inflated sufficiently to eliminate all contact with the structural support element. The fluid can be a mixture of saline and contrast, a gas such as $CO_2$, or other appropriate fluids. In some configurations, release of the outer element from the structural support element also helps to release the structural support element from the inner lumenal element of the catheter, for example to reduce or eliminate frictional engagement between the structural support element and the adjacent surface of the inner lumenal element of the catheter.

In a further example, which may be configured with any of the foregoing examples or configurations, the examples of intermediate structural members, may be used in a variable stiffness catheter whereby the stiffness of a portion of the catheter is changed by pressing or contacting a structural support element, which structural support element is contained within a cavity or otherwise unremovable from the catheter without damaging the catheter, and changed again by unpressing or removing contact with the structural support element. In one example, the catheter has a structural support element in a cavity of the catheter and fluid is used in the cavity to allow or remove contact with the structural support element as desired. In one example, fluid is used to pressurize the cavity and reduce the amount of contact with the structural support element, and reducing pressure increases the amount of contact with a structural support element. In one example of reducing pressure to increase the amount of contact with a structural support element, an inherent resiliency in an outer element can be used to increase contact between the outer element and the structural support element when fluid pressure is reduced. Alternatively, an increase in pressure can be used to increase frictional contact with such a structural support element, depending on design of the assembly.

In another example, which may be configured with any of the foregoing examples or configurations, the examples of intermediate structural members may be used in a catheter having an inner lumenal member, a structural support element, for example a stent, tubular mesh, or other structural member, and the catheter may further include an outer tubular element over at least part of the structural support element wherein the outer tubular element is configured to be in a normally collapsed state. In one configuration, the normally collapsed state is one that occurs through elastic contraction of the material of the outer tubular element, and in one configuration the elastic contraction applies pressure to the structural support element. Pressure against the structural support element produces a frictional force between the structural support element and the material of the outer tubular element to inhibit movement therebetween. In one example, an outer tubular element is expanded and placed over the structural support element on the lumenal element, and then allowed to release or collapse about the structural support element, for example configured to apply an inward pressure on the structural support element. The outer tubular element can be generally uniform in geometry and material throughout its length, but also can have different characteristics incorporated into the outer tubular element over its length and/or circumference, for example variations in durometer, thickness, geometry as well as construction (for example single piece versus multiple piece).

In a further example, which may be configured with any of the foregoing examples or configurations, intermediate structural members may be used in a catheter having an inner lumenal member, an outer tubular member, and a structural support member positioned between the inner lumenal member and the outer tubular member whereby increasing or decreasing contact between one or more surfaces of the structural support member with one or both of the inner lumenal member and the outer tubular member changes a stiffness of a portion of the catheter. Increasing or decreasing contact can be done by inflation or enlargement, for example inflation or enlargement of the outer tubular member and/or the inner lumenal member, for example sufficient to decrease the surface area of contact of one or more elements with one or more surfaces of the structural support member. In one example, flexibility of the catheter can be increased by enlarging the outer tubular member relative to the structural support member, for example by injection of fluid into a cavity around the structural support member. Flexibility of the catheter can be decreased by reducing the enlargement, for example by removing fluid from a cavity around the structural support member.

In another example, which may be configured with any of the foregoing examples or configurations, a catheter has a tubular mesh having a plurality of longitudinally extending struts interconnected by a plurality of connecting struts. Individual ones of the plurality of connecting struts can connect respective circumferentially or arcuately spaced longitudinal struts. In one example, a series of aligned longitudinal struts are circumferentially or arcuately spaced from another series of aligned longitudinal struts, and offset longitudinally. In another example, respective angles between a connecting strut and a respective longitudinal strut are acute angles. The acute angles can be angles anywhere between greater than zero and less than 90°.

In a further example, which may be configured with any of the foregoing examples or configurations, an intermediate structural member may be used between the inner and outer tubular elements for providing variability in stiffness of the assembly. In one configuration, the intermediate structural member is a flexible cylindrical member comprising a plurality of elements wherein a transverse cross-section of the flexible cylindrical member includes at least two, and in many examples at least three, elements arranged around the cylinder. In one configuration, the plurality of elements are interlinked or interconnected within the intermediate structural member. In a further configuration, the plurality of elements have discrete lengths, and in another configuration each of the plurality of elements have lengths that are less than the overall length of the structural support member, and in one configuration none of the plurality of elements extend proximally to a manual control apparatus or to a proximal catheter hub. In another configuration, the plurality of elements are different sizes, and may include different cross-sectional areas, and the plurality of elements may be identifiable in groups, one group having the same characteristics different from those in another group, for example different cross-sectional areas, different sizes, different lengths, and the like. In one example, there is a larger number of elements from one group in the intermediate structural member than the number of elements from another group. In one example, the plurality of elements are uniformly distributed over the cylinder when in a relaxed or neutral state. In one example, the intermediate structural member includes two groups of interconnected elements, the first group arranged in a transverse cross-section to have a first number of elements substantially evenly distributed about the cylinder, and the second group to have a second number of elements substantially evenly distributed, in one configuration six from the first group and 12 from the second group. The plurality of elements forming the intermediate structural member in one example are arranged in a substantially symmetrical form when in the relaxed or neutral configuration.

In a further example, which may be configured with any of the foregoing examples or configurations, a variable stiffness shaft, for example tubular elements, lumenal elements, catheters, and the like, may include a structural support member arranged relative to the shaft such that the shaft can be changed from a first shape configuration, such as a shape configuration as manufactured, to a second different shape configuration and the structural support member helps to keep the shaft in the second shape configuration. The structural support member can help to keep the shaft in the second shape configuration even in spite of application of some external forces, or even in spite of manufactured memory such as the original manufactured shape. In one configuration, the structural support member can be in a first configuration, for example a released or flexible configuration, and the shaft in the location of the structural support member can be changed or reshaped to a second shape configuration at which the structural support member is then fixed or stiffened, clamped or sandwiched to retain its then configuration. As a result, the shaft in the area of the structural support member then maintains its second shape configuration, and that portion of the shaft is inhibited from returning to its first shape configuration, even in the presence of external forces on the shaft or inherent memory in the first configuration. In one example, a catheter can be introduced into a tortuous body lumen with a structural support member associated with the catheter in a released or flexible configuration. Once the catheter is in the desired position within the body lumen, with whatever twists and turns imposed on it while transiting the body lumen, the structural support member can be stiffened, clamped or sandwiched in its then-existing second shape, and that portion of the catheter associated with the structural support member is held in the same shape. During stiffening or while the catheter portion has an increased stiffness, little or no force is applied to the vessel walls by the catheter. Therefore, the structural support member helps to impose on that portion of the catheter the shape of the body lumen in which it is positioned, giving that portion of the catheter a shape memory that is maintained even in the presence of external forces and/or any shape memory instilled at manufacture. An outer tubular element also helps to fix, stiffen, clamp or sandwich the structural support member in these examples. Therefore, a flexible shaft element, including medical catheters, can be stiffened and maintained in a large number of shapes configurations regardless of a starting shape configuration or manufactured shape configuration.

In another example of a medial member, the medial member can include an assembly of at least one structural support member and a secondary material. The secondary material may extend interior to or exterior to the structural support member, or the structural support member may be embedded in or enclosed in the secondary material. In one example, the secondary material can extend between the structural support member and an inner tubular member, and in another example the secondary material can extend between the structural support member and an outer tubular element. In a further example, the structural support member may be encased in or embedded in the secondary material. The secondary material may be a plastic, fabric, or other material suitable for the application, for example for increasing or decreasing relative movement between the structural support member and adjacent surfaces as desired.

In an example of a medial member formed as an assembly, the medial member can include a plurality of structural support members, for example a first structural support member extending longitudinally, and a second structural support member laterally outward of the first structural support member, or encircling the first structural support member or where the first structural support member is nested inside the second structural support member. The first and second structural support members may have identical configurations or different configurations, where each structural support member can have a configuration such as described herein. The medial member may also include a secondary material between the first and second structural support members. The secondary material may be a sleeve extending about the first structural support member, and may be a film, a perforated or porous membrane or material, and may be configured to allow free sliding movement between the first and second structural support members, or for increasing frictional engagement between the first and second structural support members.

In another example of flexible lumenal members having an inner member and an outer member outside of the inner member, the outer member may include a support structure forming part of the outer member, for example embedded within the outer member or attached to or forming part of an internal or interior surface of the outer member.

As used herein, "outer" in the context of outer tubular member, outer member, outer element, outer cover, outer envelope or outer wall refers to a position relative to the structural support member, and "outer" in this context does not mean outer-most.

These and other examples are set forth more fully below in conjunction with drawings, a brief description of which follows.

BRIEF DESCRIPTION OF THE DRAWINGS

FIG. 12 is a schematic of a mesh pattern for use as a structural support element for a catheter.

FIG. 13 is a transverse section of two struts in the mesh pattern taken along line 13-13 of FIG. 12.

FIG. 16 is a schematic representation of a mesh pattern for use as a structural support element.

FIG. 17 is a schematic representation of a further mesh pattern for use as a structural support element.

FIG. 18 is a schematic representation of a catheter assembly in vasculature, for example human vasculature, with a guide element.

FIG. 19 is a schematic representation of a catheter assembly in the vasculature of FIG. 18 advanced with the assistance of a guide element.

FIG. 20 is a schematic representation of a catheter assembly in the vasculature of FIG. 18 with an intervention device in place.

FIG. 21 is a schematic representation of a mandrel and a catheter shaft being assembled there on.

FIG. 22 is a schematic representation of the schematic of FIG. 21 with a structural support element assembled there on.

FIG. 27 is a schematic representation of the mandrel assembly of FIG. 21 with the catheter assembled there on.

FIG. 29 is a longitudinal cross section of another example of a catheter assembly similar to the catheter assembly of FIGS. 8-9 with another example of a structural support.

FIG. 30 is a detail of a distal end portion of the catheter of FIG. 29.

FIG. 37 is a longitudinal cross section of another example of a catheter assembly similar to the catheter assembly of FIGS. 8-9 with another example of an assembly for varying or controlling a stiffness of a portion of the catheter assembly, and with an inflation lumen in an expanded, enlarged or inflated configuration.

FIG. 38 is a detail of a distal portion of the catheter of FIG. 37.

FIG. 39 is a view similar to that of FIG. 37 with the inflation lumen in a reduced, constricted or deflated configuration.

FIG. 40 is a detail of a distal portion of the catheter of FIG. 39.

FIG. 41 is a longitudinal cross section of another example of a catheter assembly similar to the catheter assembly of FIGS. 8-9 with another example of an assembly for varying or controlling a stiffness of a portion of the catheter assembly, and with an inflation lumen combined with a support structure, in an expanded, enlarged or inflated configuration.

FIG. 42 is a detail of a distal portion of the catheter of FIG. 41.

DETAILED DESCRIPTION

Figure 1:
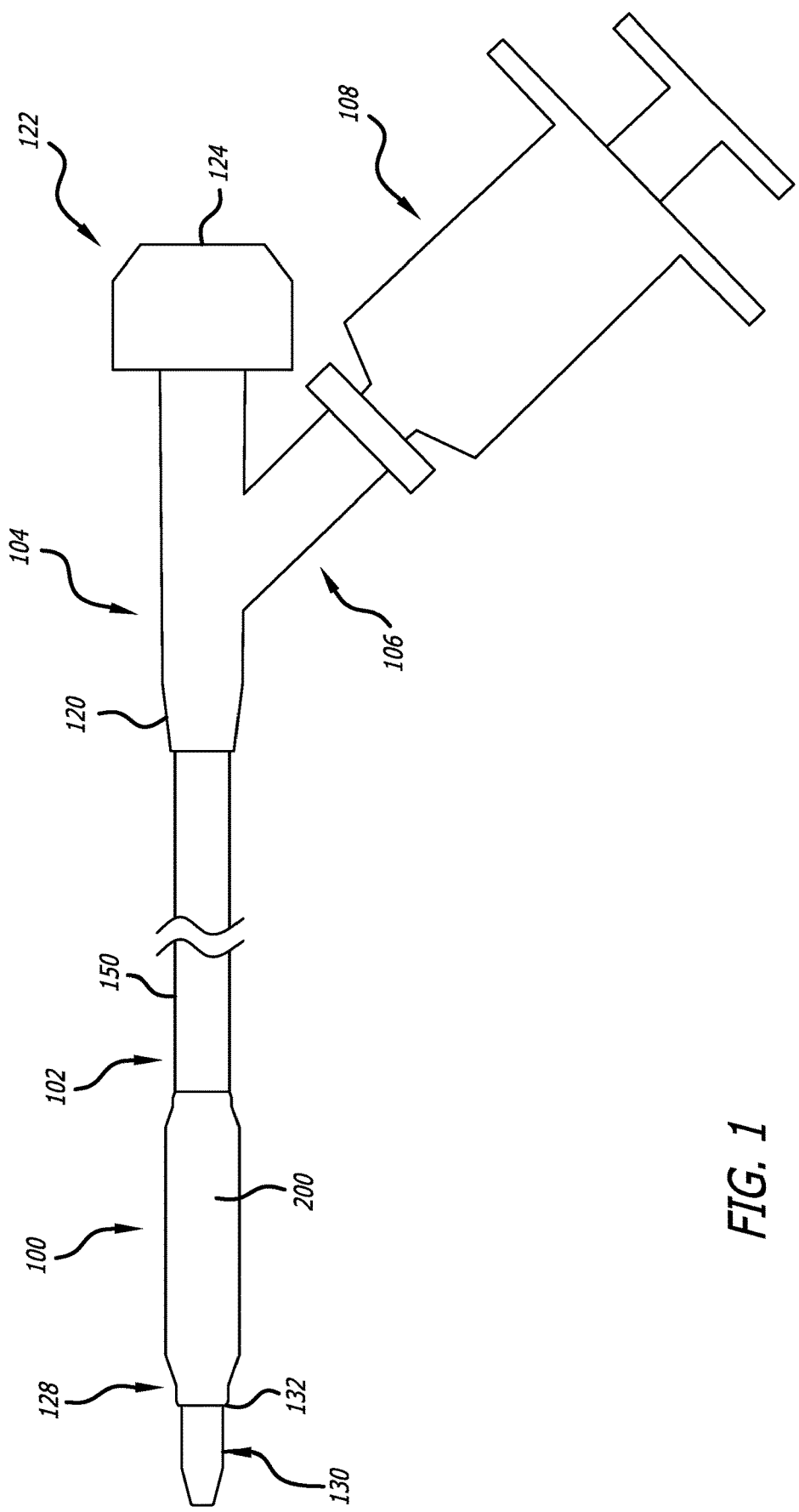
FIG. 1 is a side elevation view of a catheter assembly in accordance with one aspect of the present inventions.

This specification taken in conjunction with the drawings sets forth examples of apparatus and methods incorporating one or more aspects of the present inventions in such a manner that any person skilled in the art can make and use the inventions. The examples provide the best modes contemplated for carrying out the inventions, although it should be understood that various modifications can be accomplished within the parameters of the present inventions.

Examples of lumenal or tubular structures and of methods of making and using the lumenal or tubular structures are described. Depending on what feature or features are incorporated in a given structure or a given method, benefits can be achieved in the structure or the method. For example, tubular structures using inner and outer tubular elements, which may but need not be concentric, may be configured to have one stiffness in a first state and another stiffness in another state, for example may be configured to be relatively rigid when in a relaxed state, and less rigid when one or more elements in the tubular structures are activated. Inner and outer tubular elements can also be configured with an intermediate structural framework that can provide a more reliable support assembly when in a support configuration, for example when the inner and outer tubular elements and the structural framework are pressed together. Configurations of inner and outer tubular elements may also be used to more securely releasably fix the tubular elements in a desired geometry, for example to support passage of another element, for example an interventional device or other device, during a procedure.

Examples of inner and outer lumenal element or tubular elements and medial member forming intermediate structural frameworks can also be used to provide a more reliable support structure per unit length of an assembly of the tubular elements and structural framework. Elements of one or more of the inner and outer tubular elements and structural framework can be configured to incorporate a desired flexibility or stiffness per unit length. In one example, a structural framework can be used intermediate the inner and outer tubular elements that provides a given flexibility or stiffness per unit length, and a different structural framework can be used to manufacture or assemble another combination having a different flexibility or stiffness per unit length. In another example, a structural framework can be used to provide a given flexibility or stiffness as a function of inflation or deflation of a component adjacent the structural framework. In one configuration, the structural framework can provide an increased stiffness when an adjacent component presses against it, for example when deflation brings the component into contact with the structural framework, and can provide a decreased stiffness when the adjacent component has a reduced amount of contact with the structural framework.

In some configurations of lumenal or tubular structures, improvements can be achieved also in assembly, and in some configurations, assemblies can be produced having an assembled or final configuration with a desired stiffness or flexibility, and wherein such stiffness or flexibility can be selectively or intermittently reduced through one or more actions. For example, an assembly can be produced where a component in a relaxed or natural state presses against a structural framework, in one example where a resilient tubular structure presses against a structural framework. In another example, a user can reduce a stiffness or flexibility in an assembly by releasably inflating or enlarging at least one of the tubular structures, which can reduce a stiffness or flexibility in at least part of the assembly.

These and other benefits will become more apparent with consideration of the description of the examples herein. However, it should be understood that not all of the benefits or features discussed with respect to a particular example must be incorporated into a tubular structure, component or method in order to achieve one or more benefits contemplated by these examples. Additionally, it should be understood that features of the examples can be incorporated into a tubular structure, component or method to achieve some measure of a given benefit even though the benefit may not be optimal compared to other possible configurations. For example, one or more benefits may not be optimized for a given configuration in order to achieve cost reductions, efficiencies or for other reasons known to the person settling on a particular product configuration or method.

Examples of a number of tubular structure configurations and of methods of making and using the tubular structures are described herein, and some have particular benefits in being used together. However, even though these apparatus and methods are considered together at this point, there is no requirement that they be combined exactly as described, used together in the exact combinations, or that one component or method be used only with the other components or methods, or combinations as described. Additionally, it will be understood that a given component or method could be combined with other structures or methods not expressly discussed herein while still achieving desirable results.

Catheters are used as examples of a tubular structure that can incorporate one or more of the features and derive some of the benefits described herein, and in particular vascular catheters. Catheters used for navigation and for support for other components in vessels have a number of configurations, and such catheters can benefit from one or more of the present inventions. Tubular structures other than catheters can benefit from one or more of the present inventions.

As used herein, "substantially" and "approximately" shall mean the designated parameter or configuration, plus or minus 10%.

A lumenal or tubular structure can be incorporated into a number of devices, which may include apparatus and methods for varying the stiffness or flexibility of, or support provided by, such lumenal or tubular structure. The present examples described herein relate to lumenal or tubular structures for catheters, for example catheters for traversing vasculature, including human vasculature. However, it is understood that the components and assemblies described herein can be used in a variety of structures and applications, including catheters for other applications, and other lumenal or tubular structures. The present examples will include vascular catheters, but other structures are applicable as well.

In one example of a lumenal or tubular structure (FIGS. 1-7), a catheter assembly 100 includes a catheter having a shaft 102. The catheter assembly 100 is configured to be sufficiently flexible to transit human vasculature. The catheter assembly further includes a catheter hub 104. The catheter hub can take a number of configurations, and may be used to receive and provide a number of structures and components and/or fluids in the use and application of the catheter, and may be used with a number of other instruments and/or components as would be understood to one of ordinary skill in the art. In the present example, the catheter hub includes an inflation or injection port 106 for receiving an injection or inflation device, in the present example denominated as syringe 108 having a syringe body or barrel 110 and plunger 112, for example for injecting and withdrawing fluid from or into the barrel 110. The syringe will be used to hold and inject or withdraw saline into or from the catheter hub 104 or lumen (in the example of FIGS. 8-9 described more fully below). The syringe is mounted or secured in the inflation port 106 in a conventional way.

The catheter hub 104 includes a main body 114 extending longitudinally and defining in part a main axis of the catheter hub, at the proximal portion of the catheter. The catheter hub body 114 includes an internal wall defining a bore 116 extending from a proximal end 118 of the catheter hub to a distal end 120 of the catheter hub, and is configured in a conventional manner for receiving devices and materials, and may receive in the present example a dilator 122 as illustrated. The dilator can be omitted, or replaced by a cover or by other components. In the present example, the dilator 122 includes a dilator hub 124 mounted on or secured to the proximal end 118 of the catheter hub, and a dilator shaft 126 extending longitudinally of the catheter hub inside the wall 116 and within the catheter shaft 102. In the present example, the dilator shaft 126 extends through a distal end portion 128 of the catheter shaft and includes a dilator tip 130. In the present example, the dilator tip extends beyond a distal end surface 132 of the catheter shaft, for example a distance typical for catheter and dilator assemblies. The dilator 122 is a conventional dilator, configured for use with a catheter such as any of those described herein. In one example, the dilator is configured for receiving a guidewire or other guide device (not shown) through the central lumen of the dilator.

The inflation port 106 includes an internal wall 134 defining a bore extending to the central bore 116 of the catheter hub. The inflation bore 134 is in fluid communication with the central bore 116, and fluid from the inflation port 106 can flow into and out of the central bore 116 around the dilator shaft with the operation of the syringe 108, as well as under the influence of any other forces or influences in the design of the catheter. An interference fit between the dilator distal end and the catheter shaft distal end keeps fluid in the central bore 116.

Figure 2:
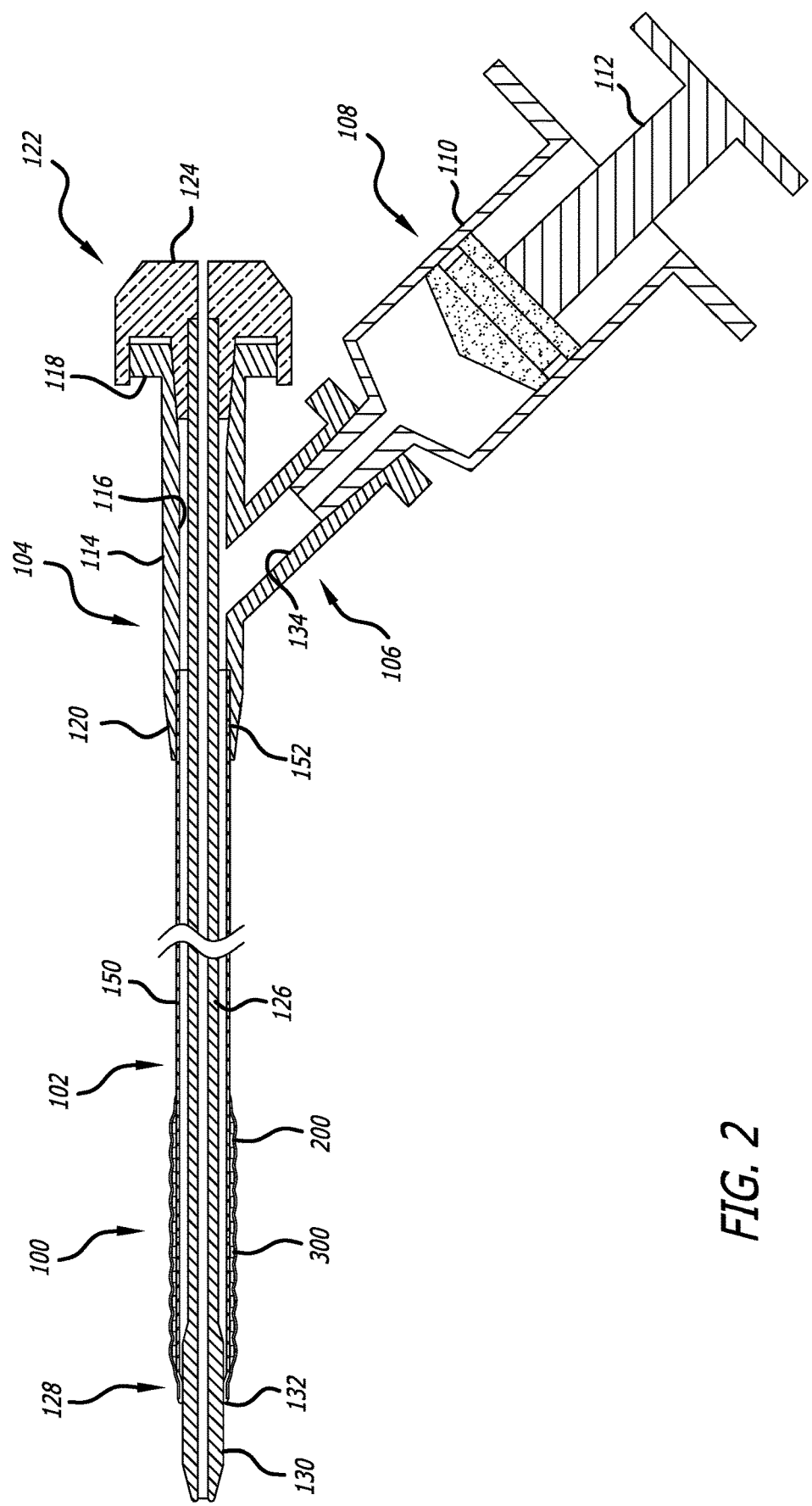
FIG. 2 is a longitudinal cross section of the catheter assembly of FIG. 1.

The catheter shaft 102 includes a lumenal member, in the present example a tubular member 150. A proximal portion 152 of the tubular member 150 is mounted, secured and sealed in the distal portion 120 of the catheter hub in a conventional manner. The tubular member extends longitudinally from the catheter hub to the distal end portion 128 of the catheter shaft, and specifically terminates in the present example at the distal end surface 132. The tubular member is formed so as to be sufficiently flexible for transiting human vasculature and body lumens, including cardiac, peripheral, and cerebral vasculature, which can be tortuous. The tubular member 150 in the present example has a substantially circular cross-section, but can have other cross-sectional profiles. The tubular member is substantially coaxial with the central axis of the catheter hub 104 when in the shape as illustrated in FIGS. 1 and 2.

The tubular member 150 is substantially cylindrical over substantially its entire length. The tubular member also has a substantially uniform wall thickness over substantially its entire length, for example 0.003"-0.020", and it also has a substantially uniform inner diameter, for example 0.025"-0.100", over its entire length from inside the catheter hub up to just proximal of the distal end portion 128, which is described more fully below. However, it is understood that other tubular geometries can be used, and the catheter shaft can be formed with other cross-sectional profiles. Alternatively, the catheter shaft 102 can have other constructions and geometries than those described herein, and such other constructions and/or geometries may include lumens, as desired, for example for passage of apparatus or fluids, such as guide wires, tubular devices, instruments, saline, contrast, and other devices and materials.

The tubular member 150 is formed from a suitable material, which may be determined by the intended application. In the present examples, the tubular member 150 is formed from an elastomeric material conventional for vascular catheters, for example PEBA, polyurethane, or similar. The internal and external surfaces of the tubular member are configured to have the desired finishes for their intended purposes. In the present example, the outside surface 154 (FIG. 3) permits easy movement through other devices and through vasculature, as necessary. The inside surface 156 permits fluid flow within the tubular member and easy movement of the dilator shaft 126 and any other devices or materials as desired, such as interventional devices/instruments.

Figure 3:
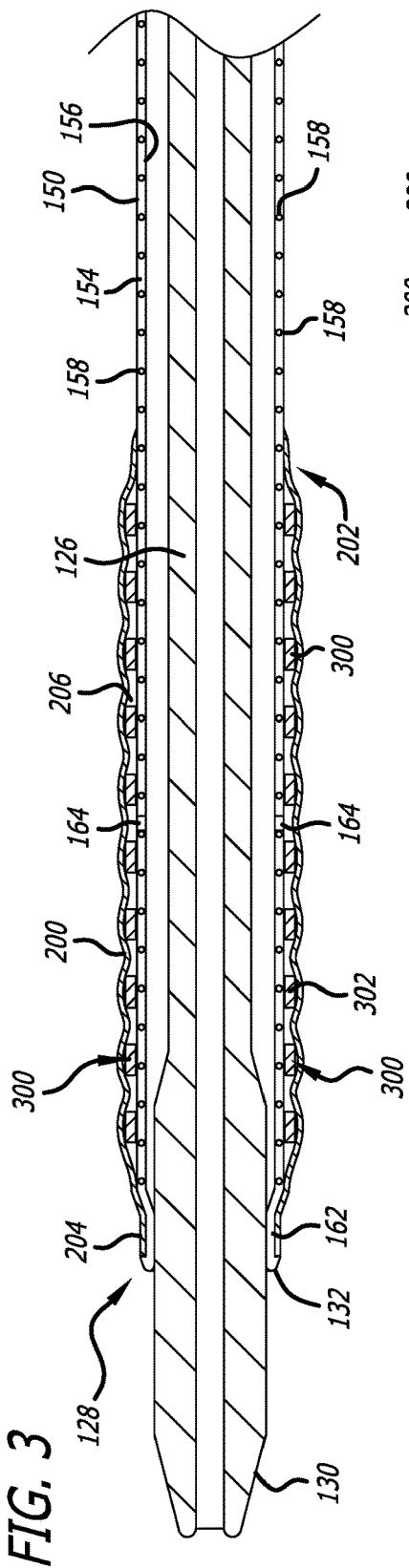
FIG. 3 is a detail of the cross section of the assembly of FIG. 2.
Figure 4:
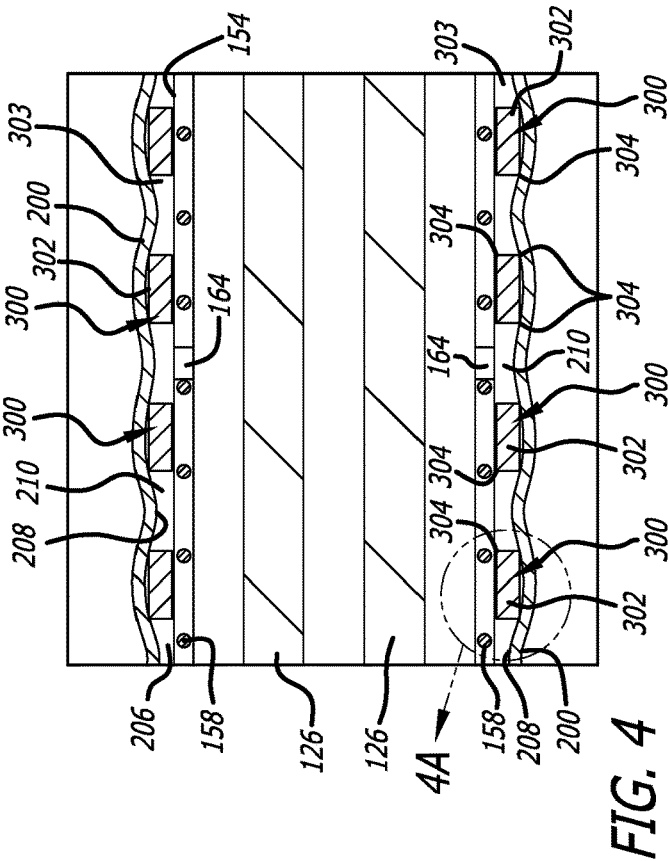
FIG. 4 is a detail of the cross-section illustrated in FIG. 3.

In the illustrated example, the tubular member 150 includes strengthening elements. In the present example, the strengthening elements include one or more helical coil structures 158 (FIGS. 3 and 4). In the present example, the helical coil 158 is a single continuous helical coil extending from inside the catheter hub 104 to a point adjacent the distal end portion 128 of the tubular structure. The helical coil can take the form of conventional reinforcement for conventional catheter tubes, and may be stainless steel, for example 304 or 316 stainless steel, with a diameter of 0.001"-0.007", and a pitch of 0.003"-0.020". Furthermore, the coil may be formed from a wire with a non-circular shape in cross section, such as a rectangle or oval cross section. The coil can be formed from other materials, with other coil and strand diameters and/or with other pitches, to provide the desired strength, reinforcement and/or stiffness. Other strengthening devices can be used, either alternatively or additionally. For example, braid structures can be used. In the present example, the strengthening elements are embedded in or coextruded with the tubular member 150, for example as would be conventional.

The tubular member 150 extends distally to the distal end portion 128, where the coil 158 terminates. The elastomeric tubular member continues distally at a converging portion 160, which then terminates at a cylindrical or annular wall portion 162. The distal end portion 128 is formed with a diameter so as to provide an interference fit with the dilator tip 130, both of which are configured to provide the desired interference fit.

The tubular member 150 geometry and structure in the present example extends uninterrupted from the proximal to the distal end portions except for one or more apertures or fluid openings 164 (FIGS. 3-4). The apertures 164 extend completely through the tubular wall between strands of the coil and provide a fluid path between the inside and the outside of the tubular member at a location of the openings, which in the present example are within an outer tubular member described more fully below. The fluid openings allow fluid to pass from the lumen within the tubular member 150, for example fluid from the inflation port 106, to a cavity or recess or balloon outside the tubular member 150. In the present example, there are two fluid openings through the wall of the tubular catheter member.

Use of fluid to expand and/or contract the volume of a cavity containing a structural support element allows changing conditions of the tubular structure. For example, inflation and deflation or reduction in pressure or application of vacuum can change a stiffness or flexibility of a structure. In one example, inflating a cavity containing a structural support element can increase the flexibility of the catheter in the area of the structural support element, and reducing the pressure, applying vacuum or allowing deflation of the cavity can decrease the flexibility of the catheter. In this way, the catheter can have a selective adjustability of its stiffness or flexibility.

The configuration of the tubular member 150, as the inner layer or inner tubular element, can be configured in a number of ways. Flexibility can be enhanced along the length, including in the distal portion of the tubular element, by changing the durometer of the material as a function of its length, and/or adjusting the wall thickness of the tubular member as a function of length or distance from the catheter hub. Alternatively and/or additionally, the reinforcement can be modified as a function of distance from the catheter hub, for example by changing the geometry or the spacing of the material. In the example of a helical coil, the pitch of the coil can be changed, or the diameter of the coil or strand element embedded in the tubular member. The reinforcement material can be metal or non-metal, and may be stainless steel, nitinol, polymeric fiber, metallic wire with a radio opacity property, tantalum, tungsten, or alloys of these materials or other materials.

The catheter 100 further includes an adjustable member outside of the catheter tubular member 150, extending over at least a portion of the outer surface of the tubular member 150. In the area of the adjustable member, the catheter tubular member 150 is an inner tubular member relative to the outer adjustable member. In some configurations, the adjustable member is used to selectively establish or change a flexibility or stiffness of a portion of the catheter, for example the portion of the catheter around which the adjustable member is positioned. The adjustable member can be used to sandwich one or more underlying components within an envelope, cavity or area over or around which the adjustable member extends. The adjustable member can be used to increase surface areas of contact between adjacent elements, and to establish or increase internal forces that must be overcome to move or change a geometry of a portion of the catheter. The adjustable member can also be used to effectively separate itself from a portion or all of an underlying component, which may allow separation of additional components from each other, and which may also allow position adjustments or other adjustments of one or more underlying components. The adjustable member can be configured to be normally in a first condition or normally in a second condition (for example having a memory characteristic), for example normally producing contact with underlying components or normally separating from underlying components, or normally applying pressure or normally released from applying pressure. Alternatively, the adjustable member can be configured to remain in a given state until acted upon, for example without any memory characteristic. In the examples described herein, the adjustable member is configured to be normally in a collapsed, reduced or application mode where pressure or force is applied by the adjustable member to one or more underlying components. The adjustable member is adjusted by positive action to change the adjustable member from its collapsed, reduced or application mode at least in part, for example to reduce a surface area of contact between the adjustable member and an underlying component. In the present examples, the adjustable member is movable radially. Also in the present examples, the adjustable member applies pressure to an underlying component along the entire length of the underlying component substantially simultaneously.

An example of an adjustable member (FIGS. 1-9 and 11A-B) is tubular member 200. In the present example, the tubular member 200 extends over a portion of the catheter shaft 102. The tubular member 200 forms an outer tubular member (outer tube) to the extent that it is outward of the adjacent portion of the catheter shaft 102. However, it is understood that one or more other components can be outward of the outer tubular member 200. A proximal end 202 of the outer tube is secured to an adjacent portion of the catheter tubular member 150, circumferentially around the entire portion of the proximal end 202 of the outer tube. The proximal end can be sealed, welded, bonded, for example thermally or adhesively, or otherwise secured to the outer surface of the catheter tubular member 150, for example in a manner similar to concentric catheter tubes may be secured to each other in conventional catheters. With the present outer tube, the outer tube is secured to the catheter tubular member 150 at both ends of the outer tubular element in such a way that the junction can withstand expected internal fluid pressures developed between the outer tubular member and the catheter tubular member 150.

The outer tube 200 extends distally from the proximal end portion 202 over the catheter tubular member 150 to a distal end portion 204 of the outer tubular member, surrounding the distal end portion 128 of the catheter tubular member 150. The distal end portion 204 is sealed, welded, bonded or otherwise secured to the adjacent distal end portion of the catheter tubular member in the same manner as for the proximal end portion 202. The outer tube 200 forms between the proximal and distal end portions a cavity, envelope or annular space 206 between the inside surface 208 of the outer tube 200 and the opposite or facing outer surface 154 of the inner tubular member 150. The cavity 206 forms in the present examples a balloon which can be enlarged or inflated as a function of the flexibility and strength of the outer tubular member 200. In some configurations, the adjacent portion of the inner tubular member may also be sufficiently flexible to provide a measure of additional inflation or enlargement, inwardly toward the central axis of the catheter, but the present configurations have the inner tubular member 150 with the embedded coil 158 such that the wall of the inner tubular member does not change diameter significantly under the presently contemplated pressures within the cavity 206, and remains a constant diameter before, during and after inflation or enlargement of the outer tubular element and an before during and after deflation or full collapse of the outer tubular element.

In the present example, the outer tube 200 is a monolithic structure, and is formed from a material that is flexible and can increase in diameter (i.e., increase in diameter where the outer tube is substantially cylindrical or circular) upon application of an internal pressure (for example between approximately 1-200 psi) between the outer tube 200 and the inner tube 150. The outer tubular element serves as a balloon that can expand outwardly upon application of an internal pressure, for example pressure developed by a fluid, in one example a relatively incompressible fluid. The outer tubular element 200 is configured to have a maximum expandable diameter under normal operating conditions for example by selecting a material that can inherently expand or stretch to a selected or preferred diameter and maintain that diameter even with possible expected higher pressures.

The outer tubular element 200 in the present examples is formed from polyurethane, and has a wall thickness of approximately 0.003". In the present examples, the outer tubular element 200 has a relaxed internal diameter when originally formed and before assembly on the catheter of approximately 0.100", when the other components inside the outer tubular element are dimensioned as described herein. It has an expected inflated internal diameter of 0.118". The material is preferably abrasion resistant, and highly resistant to puncture. The outer tubular element 200 in the present examples has a structure similar to balloon catheters but without any folds or creases, and can be produced in a manner similar to balloon blow molding processes. In the present example, the outer tubular element 200 is formed prior to assembly to be configured to be normally collapsed when assembled in the catheter. Once installed and if the outer tubular member is enlarged or inflated, the material of the outer tubular member is configured to produce an elastic recoil when the pressure is reduced or removed. The outer tubular member can be modified in a number of ways, but in the present examples is configured to be uniform throughout its length. In other examples, the outer tubular member can be configured to have different characteristics at different places along its length, for example based on durometer, thickness, the original or relaxed or recovered shape and/or diameter, material and thickness, and circumferential configuration. However, in the present examples, the response of the outer tubular member to inflation or enlargement pressure from an internal fluid is relatively uniform throughout the outer tubular member, and reaches a predetermined outer diameter, which is maintained even with higher pressures until pressure is removed and the outer tubular member deflate, retracts or returns to the structural support element. In this way, inflation or expansion of the outer tubular element allows disengagement of layers without overstretching the outer tubular element. The outer tubular element can be configured to have a non-linear pressure versus diameter relationship such that the diameter of the outer tubular element can increase with pressure up to a predetermined diameter, after which no further expansion occurs.

In the present examples, the catheter tubular member 150 and the outer tubular element 200 form nested tubular structures which are concentric, and together they define a cavity. Alternatively, they can be other than concentric, and they can have geometries other than cylindrical or circular cross-sections.

Lumenal structures and tubular structures, including the tubular catheter 100 can include support structures, for example medial or intermediate support structures, that can provide stiffness to the lumenal and tubular structures, and in the present examples, can provide selectable or variable adjustable stiffness or flexibility to the lumenal and tubular structures. The support structure can be placed the entire length or at a number of locations along the length of the lumenal and tubular structures, and in the present examples, the support structure is positioned adjacent the distal end of the catheter. In the present example, the support structure is a medial member that is placed between the lumenal and tubular structures. In one configuration of the support structure and the lumenal or tubular structure, the support structure can have an adjustable stiffness or modifiable stiffness configuration, which configuration can be affected by its geometry and how it is combined with the lumenal or tubular structure. In one configuration, the support structure is sandwiched or interposed between two structures, one or both of which may be adjustable relative to the support structure to change the stiffness of the assembly. In that or another configuration, the support structure has surfaces contacting one or more adjacent surfaces in the lumenal or tubular structure, which contact results in frictional forces if the support structure bends or otherwise changes its configuration. The frictional forces resist the configuration change, contributing at least in part to increased stiffness or decreased flexibility of the assembly, for example in the area of the support structure.

The support structure can take a number of configurations, and when placed over a lumenal or tubular structure, the support structure can also be a tubular support structure. The support structure can take the form of a tubular mesh, including a non-random mesh configuration, a tubular skeletal structure, a tubular framework, a tubular braid, a stent, for example such structures as medically implantable stents, and other structures. "Non-random" as used herein in the context of a structural support element is one that includes elements between the ends of the structural support element that were configured in a selected or controlled way. In some configurations, for example where the support structure is a tubular mesh, skeletal structure, framework or stent, elements making up the support structure can have a relatively high degree of interconnectedness, while still providing some degree of freedom of movement. In contrast to stents, however, the present support structure does not expand radially or extend longitudinally substantially once the catheter is assembled, other than what might occur on bending of the catheter and therefore the support structure. In the art of stents, a relatively low degree of interconnectedness would be termed an open cell configuration, and a relatively high degree of interconnectedness would be termed a closed cell configuration, or one tending more toward a closed cell configuration than an open cell configuration. Higher levels of interconnectedness in a tubular mesh, skeletal structure or framework may have more interconnections between elements than fewer interconnections. Interconnectedness contributes to an ability or inability of the support structure to move or change its geometry, with movement being easier with fewer interconnections, and more difficult with more interconnections.

In addition to the inherent characteristics of the support structure to allow or resist movement or changing geometry, interactions of the support structure with adjacent surfaces also affects resistance to movement or changing geometry. For example, larger surface areas of contact between the support structure and adjacent surfaces give rise to frictional forces to a greater extent resisting movement or geometry changes than smaller surface areas of contact. Support structures having larger numbers of components with surface areas that can contact the adjacent surfaces will exhibit higher resistance to geometry changes or movement than ones having smaller numbers of components, all other things being equal. Similarly, the surface characteristics of the components of support structures may also affect the resistance to geometry changes or movement. For example, surface textures or surface edges may contribute to higher frictional forces when in contact with adjacent surfaces that may resist geometry changes or movement. In one configuration, described more fully herein, a surface of the support structure facing an adjacent surface may be configured to include raised structures, for example protrusions or raised areas or outwardly extending structures (outwardly of the surface), or a combination of raised and recessed areas, which may contribute to higher frictional forces when in contact with the adjacent surface to help resist geometry changes or movement. For example, one or more facing surfaces of the support structure may include one or more raised structures extending outward from the facing surface a distance and having an element or surface area that may come into contact with the adjacent surface, and a raised structure may have a number of configurations such as pointed, extended or distributed, or other surface configurations that can contact the adjacent surface.

The catheter 100 includes an intermediate or medial member in the form of support structure 300 (FIGS. 2-9). In the present example, the medial member is solely the support structure 300 in the form of at least one monolithic structure having a tubular shape made up of component elements such as spars, struts, or linear or curving limbs 302 interconnected with each other with open space 303 in between to form the support structure 300, and the cross sections of FIGS. 2-9 show cross sections of elements of the support structure 300 not to scale with the pitch of the coil 158, with the understanding that the example of the support structure 300 is shown in and described in more detail with respect to FIGS. 10-13. The support structure is a three-dimensional configuration of spars, struts, or linear or curving limbs and intermediate cavities or openings whose configuration can be selectively adjusted or changed and releasably fixed in place as desired. The adjacent structures can be selectively coupled and decoupled to provide support or tracking as desired. In the present examples, three components are mechanically or frictionally decoupled to a greater or lesser extent to allow selective changing or adjustment of the configuration of the support structure, after which the three components can be re-coupled, for example mechanically and with increased surface areas of contact for frictional engagement.

In the present example, the support structure 300 is positioned intermediate the tubular member 150 and the outer tubular member 200, in the cavity or annular void 206 formed between the inner tubular member and the outer tubular member 200. Also in the present example, the support structure 300 extends substantially from the proximal end portion 202 of the outer tubular element 200 to the distal end portion 204, and the configuration of the support structure is substantially consistent over the length thereof. However, the support structure can be configured to have different configurations as a function of axial position and/or circumferential position. The support structure 300 can be secured to the outer surface 158 of the inner tubular member 150, for example by tacking, adhesive, or other means, such as at one or several endpoints at the proximal and distal ends of the support structure. Such securement may assist in assembly, and such securement can be eliminated prior to final assembly if desired. Conversely, flexibility of the distal portion of the catheter can be reduced as a function of securement of the structural support 300 to the inner tubular member 150, axially and/or circumferentially. However, such reduction generally would not be reversible, and would decrease the baseline flexibility or increase the stiffness of the distal portion of the catheter and it could be difficult to increase the flexibility above the baseline or reduce the stiffness.

Figure 4A:
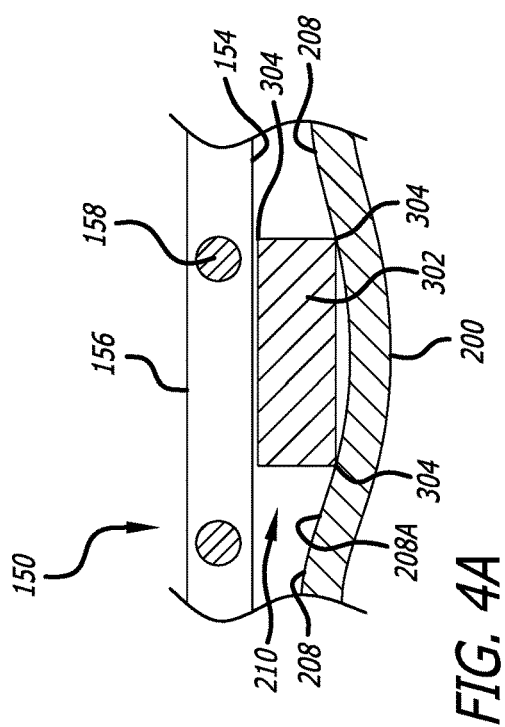
FIG. 4A detail of a portion of the cross section of FIG. 4 taken at 4A.

The components of the structural support 300, such as the limbs 302, can have a number of geometries. In the present example, each limb 302 has a substantially rectangular cross-section with a long axis parallel to the main axis of the catheter, and short axis perpendicular thereto. Having the long axis parallel increases the surface area of each limb that can contact an adjacent surface 158 of the inner tubular member and the inner surface 208 of the outer tubular member 200. However, other geometries can be used. In the present example, each limb 302 of the support structure 300 is illustrated in FIGS. 4 and 4A as being slightly spaced outward from the outer surface 158 of the inner tubular element 150. The support structure can be configured to have a larger inside diameter in a relaxed state than an outside diameter of the outer surface 158, which may then produce limited surface contact between the structural support 300 and the inner tubular member 150 when first assembled. Alternatively, the support structure can be configured to have an inside diameter in the relaxed state comparable or approximately the same as the outside diameter of the outer surface 158, so that greater surface contact occurs between the structural support and the inner tubular member. In another alternative, the structural support 300 can be configured to have a smaller inside diameter in the relaxed state, for example through an inherent bias in the support structure, to have a higher surface area of contact with the inner tubular element in the relaxed state. Higher surface area of contact promotes stiffness, relative to lower surface area of contact between the support structure 300 and the inner tubular element 150.

As illustrated in FIG. 4, each limb 302 of the structural support 300 has a relatively defined set of corners or angular transitions 304 from one side to an adjacent side. The corners 304 are exaggerated in their sharpness, but the curvature of the transition between surfaces around a perimeter of a limb can affect frictional forces arising through contact between a limb and an adjacent surface, either with the outer surface 154 of the inner tubular element or with the inner surface 208 of the outer tubular element. The quantity or extent and the quality of the edge contact between limbs and their adjacent surfaces will contribute more or less to the stiffness or flexibility of the combination. All other things being equal, sharper or more angular transitions between surfaces produce higher frictional forces and increased stiffness or decreased flexibility. Therefore, a non-round limb profile on the structural support 300 can enhance the stiffness or reduce the flexibility of the distal portion of the catheter when the structural support contact the adjacent surfaces. Similarly, textures on surfaces of the support structure contacting adjacent surfaces of the tubular elements can also increase friction and stiffness or decreased flexibility. For example, a nitinol structural support 300 that is not electro-polished may enhance the stiffness or reduce the flexibility of the distal portion of the catheter as a result of surface contact with the adjacent surfaces of the inner and/or outer tubular elements.

The structural support element can be formed from a number of materials, including stainless steel, nitinol, polymeric materials, and other suitable materials. The structures can have cross sectional geometries that are smooth or angular, and may be finished or unfinished, etched or not, abraded or not (e.g., grit blasting), and for example with nitinol, electropolished or not. A structural support element such as a stent will be configured to have a structure, material, and characteristics of such a stent, such as extends used for medical implantation.

The illustrations of catheters in FIGS. 1-9 show the catheter shaft extending straight, in what is considered a neutral configuration. In such a configuration, and as can be seen in FIG. 4, the outer surface 158 extends axially substantially straight, and the adjacent surfaces of the limbs 302 of the support structure 300 extend substantially parallel to the outer surface. Relatively little frictional engagement occurs in such a configuration between the corners 304 and the outer surface 154 until such time as the catheter bends. When the catheter bends, the concave portion of the bend may have relatively higher contact and frictional engagement with the corners 304 of the adjacent limbs, for example at both corners of a limb, whereas in the convex portion of the bend, fewer of the corners 304 might contact the adjacent outer surface 154.

The outer tubular element 200 is relatively more flexible than the inner tubular element 150. In a configuration where the outer tubular element 200 is constricted, deflated, or otherwise pressed against the support structure 300, the flexibility of the outer tubular element 200 allows the inner surface 208 to somewhat conform to the adjacent surface of the support structure. Specifically, the inner surface 208 extends over a limb 302 and curves or bends around adjacent corners 304 it contacts. Additionally, the outer tubular element 200 extends into the gaps or spaces 210 between adjacent limbs of the support structure. Consequently, possible movement of the limb 302 to the left as viewed in FIG. 4A (or outward toward the outer tubular element 200) will tend to increase the frictional engagement between the corner 304 and the adjacent surface 208A, increasing the resistance to movement of the limb. Similar actions occur with other limbs and their adjacent surfaces of the outer tubular element, thereby accumulating forces resisting movement, and also increasing the stiffness or decreasing the flexibility of that portion of the catheter. Any increase in frictional engagement between limbs of the structural support 300 and adjacent surfaces of the outer tubular element 200 and/or inner tubular element 150 as a result of bending of the catheter will depend on the location and direction of the bending.

Resistance to bending or stiffness in the distal portion of the catheter can be reduced by reducing the amount of surface area of contact between one or more limbs 302 of the support structure 300 and one or more adjacent surfaces. The extent to which such contact can be reduced may depend on which surface or surfaces release or move out of contact with the support structure, and how many surfaces release or move out of contact. In one configuration, contact between the support structure and one or more adjacent surfaces may occur simply by moving the catheter, so that the adjacent surface 154 of the inner tubular structure 150 and/or the adjacent surface 208 of the outer tubular structure 200 slide or slip over the respective limb surface. In another configuration, including those illustrated herein, one or both of the adjacent surfaces of the inner tubular structure and the outer tubular structure become separated from the respective surface or surfaces of the support structure, thereby reducing or eliminating surface contact therebetween, and thereby reducing or eliminating the contributions of those surfaces resisting movement of the catheter.

In one example (FIGS. 5-6), the outer tubular element 200 can be released, moved away or separated from one or more adjacent surfaces of the support structure 300. For example, fluid in the syringe 108 can be injected into the lumen 134 of the inflation port, and into the interior lumen of the catheter hub and the catheter. As the pressure in the interior of the catheter increases, fluid flows through the apertures 164 into the annular cavity 206 between the inner and outer tubular members. With the increase in pressure in the annular cavity, the outer tubular element expands or enlarges, and the interior walls 208 begin to move radially outward, and out of contact with, or mechanically and frictionally disengage from, the adjacent surfaces of the structural support 300. The amount or extent of disengagement will be a function of the pressure, and the location or locations of the apertures 164. In the example of an incompressible fluid and sufficient apertures 164 distributed along the cavity 206, substantially all of the outer tubular element will release from the structural support 300, both circumferentially and longitudinally. When all or any portion of the outer tubular element releases from adjacent surfaces of the limbs 302, the flexibility of the catheter in the area of the outer tubular element commensurately increases and the stiffness commensurately decreases. Conversely, as more of the outer tubular element comes into contact with adjacent surfaces of the limbs 302, the flexibility of the catheter in that area commensurately decreases and the stiffness commensurately increases.

Figure 5:
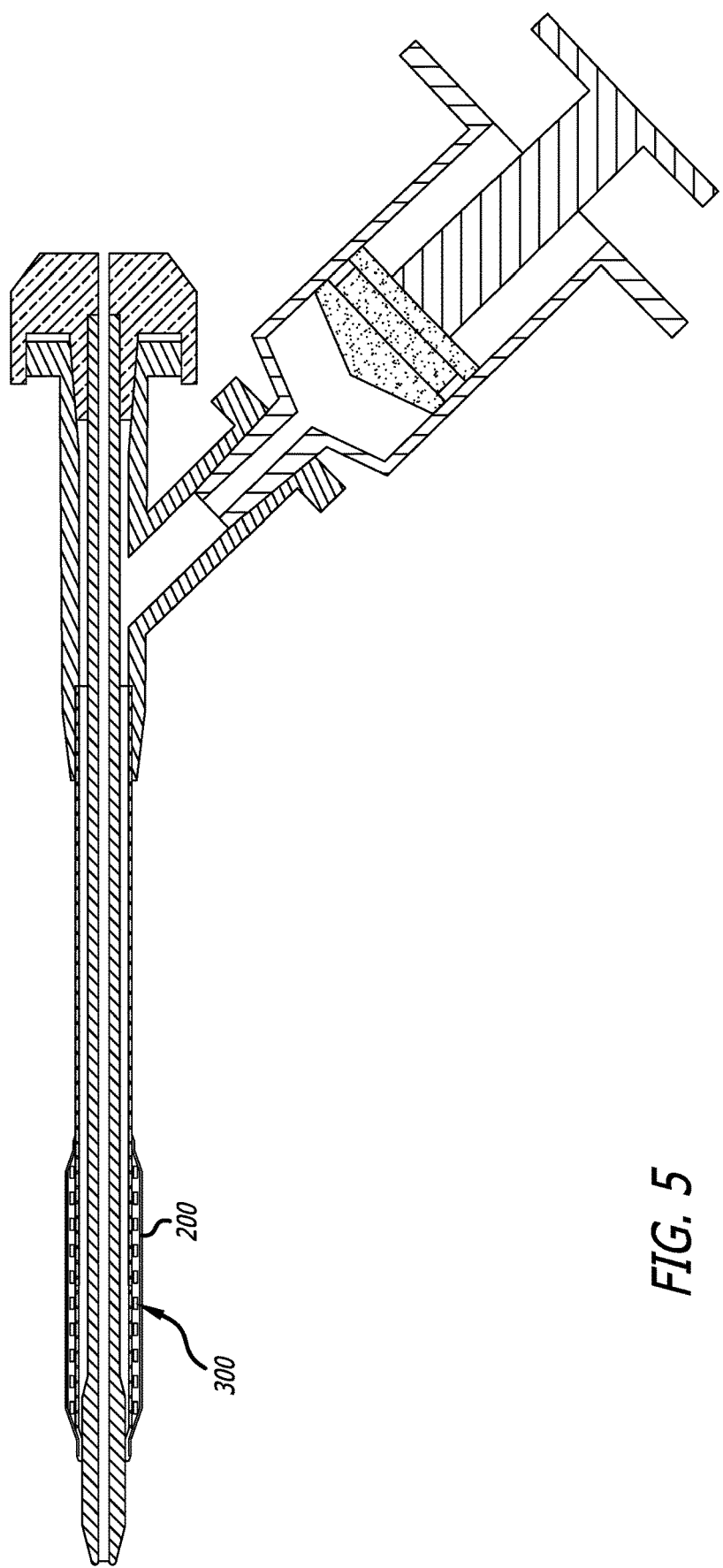
FIG. 5 is a longitudinal cross section of the catheter assembly of FIG. 1 with a portion of the catheter enlarged or inflated.
Figure 6:
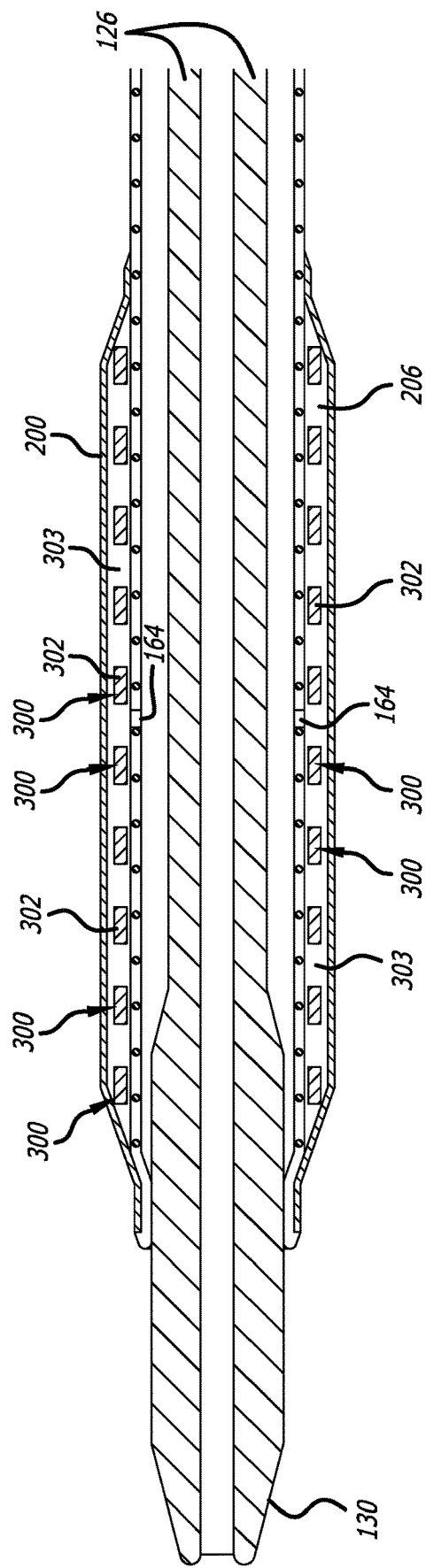
FIG. 6 is a detail of the enlarged or inflated portion of the catheter assembly illustrated in FIG. 5.

In the example illustrated in FIGS. 5-6 and other examples herein, variable stiffness is incorporated in a portion of a catheter. For example, when the outer tubular element is in a relaxed state, such as when excess fluid is removed from the annular cavity 206 and the catheter lumen, such as by withdrawing the plunger 112 on the syringe 108, or by applying vacuum, that portion of the catheter has increased stiffness. Conversely, when the outer tubular element is expanded or inflated, such as by injection of fluid into the catheter lumen and the cavity 206, the portion of the catheter has decreased stiffness. Therefore, in the examples herein using inflation and deflation, inflation and deflation can be used to affect stiffness or flexibility of the tubular element. In the present example, inflation increases flexibility. Similarly, a relaxed or natural state of the outer tubular element decreases flexibility and provides a stiffer construction. Additionally, the ability to increase or decrease stiffness or flexibility depends in part on the encapsulated or encased structural member 300, which is independent of structures outside the outer tubular element or structures inside the dilator. The intermediate or medial structural support 300 is sandwiched between opposing continuous surfaces, one or both of which are movable, for example radially, such as where the outer tubular element 200 can expand radially outward relative to the structural support 300.

In the present examples, the outer tubular element wall is movable with fluid pressure, outward with increasing fluid pressure, and inward with decreasing fluid pressure. Increasing the fluid pressure separates or widens the spacing between the facing walls of the outer tubular element and the inner tubular element, 208 and 154, respectively. Decreasing the fluid pressure decreases the spacing between the facing walls of the outer tubular element and the inner tubular element, and eventually brings the outer tubular wall into contact with one or more limbs of the structural support 300. As pressure is removed, the outer tubular element applies pressure to the structural support 300 squeezing the structural support between the outer and inner tubular elements, thereby changing the mechanical properties, stiffness and flexibility of that portion of the catheter. Where fluid is used to inflate the outer tubular element, it can be seen that the structural support 300 is in a closed fluid system, and in a cavity that is closed except for fluid communication with a source of fluid for fluid pressure. Having the support structure in an enclosed cavity in the catheter provides more predictability in the adjustability of the stiffness or flexibility of the catheter. Additionally, when the outer tubular element is formed from a material and configured on assembly to be resiliently biased in the direction of the structural support member, the resiliency of the outer tubular element helps to maintain the sandwich or application of pressure on the support structure when pressure is reduced or removed. Flexibility of the catheter can be adjusted by changing how the structural support element 300 is captured between the layers or concentric tubular elements of the outer tubular element 200 and inner tubular element 150. Flexibility can be adjusted by manipulating fluid in the fluid system of the catheter lumen and the cavity 206, and the fluid can be used to separate or increase the spacing between the concentric tubular elements. Similar effects can be achieved by reducing fluid pressure in the cavity, for example where the outer tubular element has a relaxed or unbiased configuration, making little or no contact with the support structure. By reducing pressure in the cavity 206, the outer tubular element can be drawn into further contact with more surface area of the structural support, thereby increasing the surface area of contact and the rigidity or stiffness of that portion of the catheter. Alternatively in the examples illustrated herein where the outer tubular element is configured in its natural or relaxed state to be pressing against the structural support element, for example where in the relaxed state the outer tubular element has an inside diameter less than an outside diameter of the structural support element, the natural configuration of the assembly is to have the outer tubular element pressing against the structural support element absent increased fluid pressure in the cavity 206. Additionally, the assembly can be configured so that fluid pressure reduces naturally if no active pressure is being applied to the syringe 112 by a user.

Figure 7:
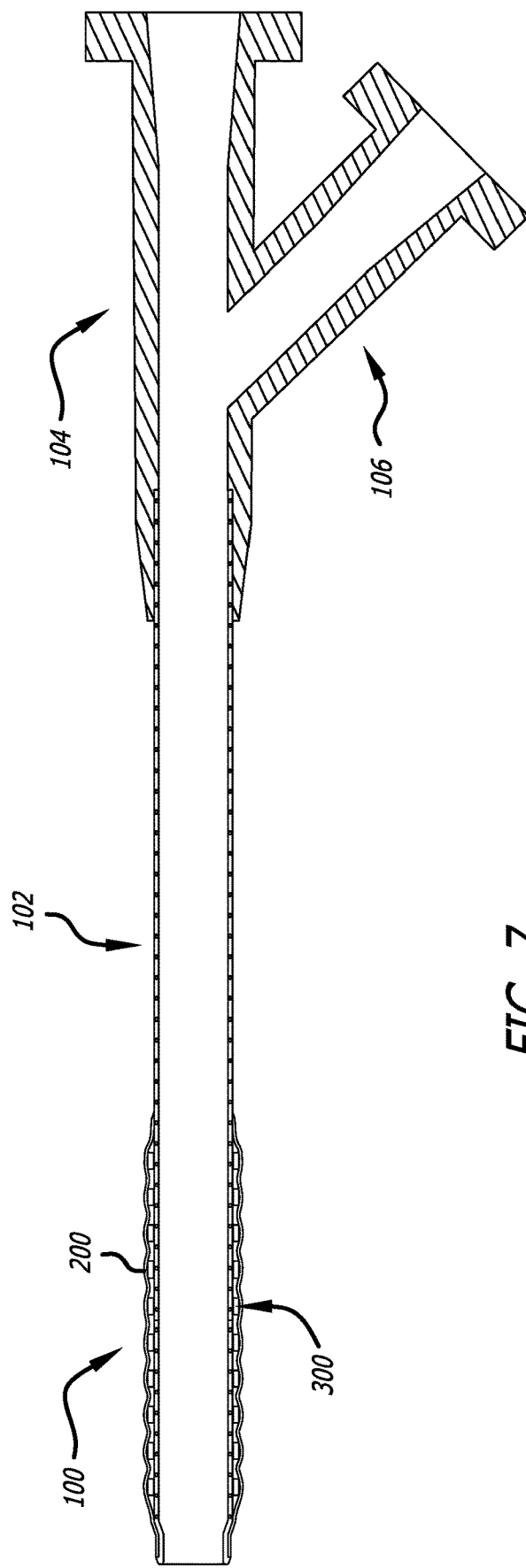
FIG. 7 is a longitudinal cross section of a portion of the catheter assembly of FIG. 1.

The catheter assembly is used so that the catheter 100 can be positioned in a desired position, for example within the vasculature, for example by using a guide device to guide the catheter into a desired location and position. For example, a guidewire (not shown) extends into the central lumen of the dilator and is guided into the appropriate vasculature, and the dilator and catheter with the outer tubular element inflated or enlarged is passed along the guidewire until positioned as desired. Once in position, the outer tubular element is deflated or reduced to fix the catheter geometry in position. The dilator 122 is then removed, and the remaining catheter with the adjustable flexibility element fixed remains in place for subsequent procedure. As shown in FIG. 7, the dilator has been removed and the syringe 108 has been removed from the injection port 106. The catheter is then ready to receive an intervention device, material or other component through the catheter hub 104. When the procedure is complete, fluid is reintroduced into the lumen either with the intervention device in place or a dilator, a syringe attached to the injection port 106 and the outer tubular element 200 inflated to allow removal of the catheter 100.

Figure 8:
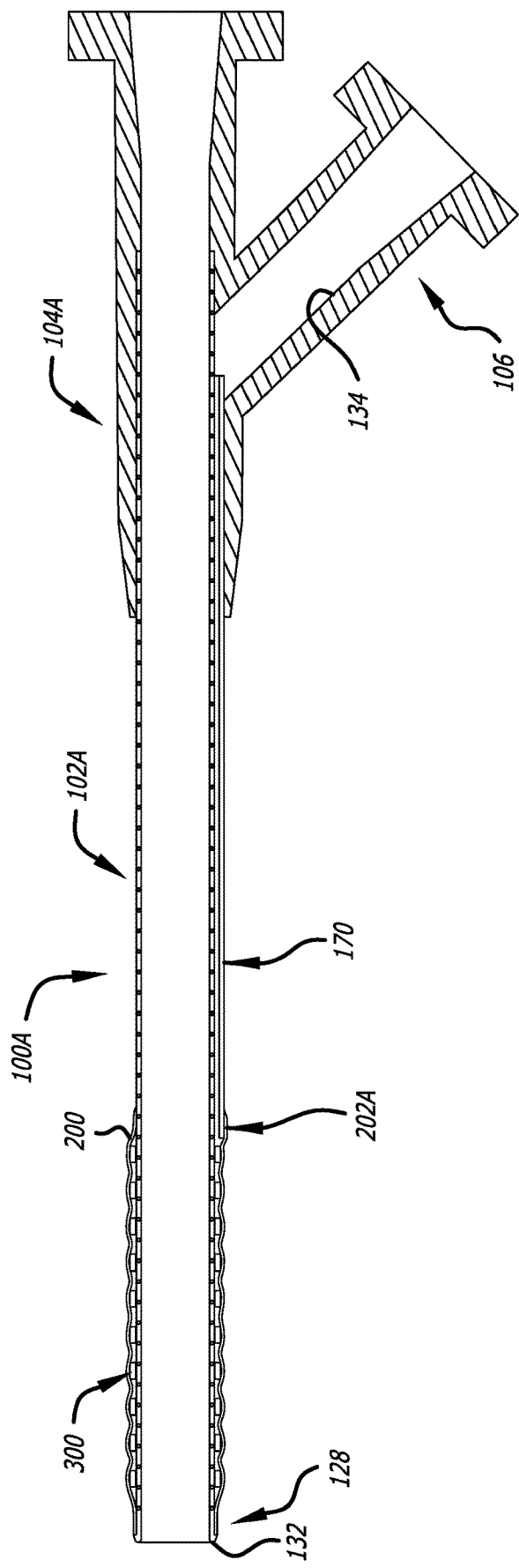
FIG. 8 is a longitudinal cross section of another example of a catheter assembly.
Figure 9:
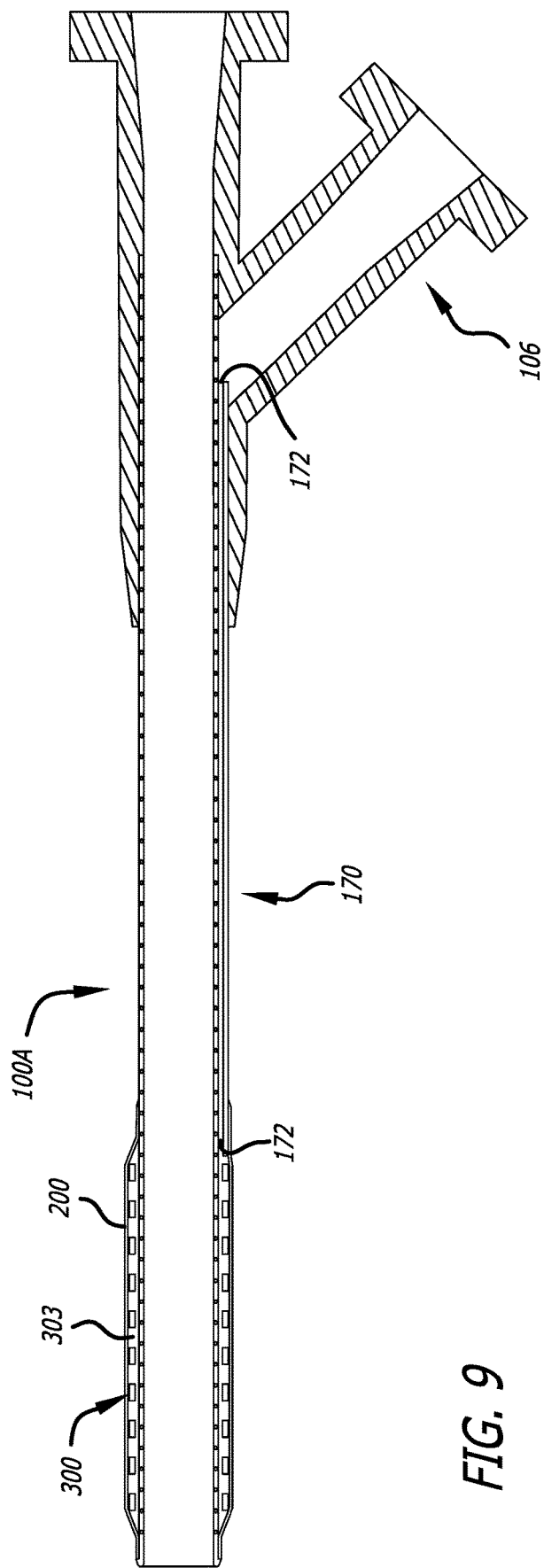
FIG. 9 is a longitudinal cross section of the catheter assembly of FIG. 8 with a portion of the catheter enlarged or inflated.

In an alternative embodiment of a catheter (FIGS. 8-9), a catheter 100A has an outer tubular element 200 enclosing a structural support 300, and has the structures and functions described above with respect to the example of FIGS. 1-7 except as discussed herein. In the present example, the catheter 100A includes a catheter shaft 102A identical to the catheter shaft 102 but for omitting the apertures 164, but for the proximal portion of the catheter shaft extending further into the catheter hub 104A beyond the opening of the injection port 106, and except for one or more inflation lumens 170. The construction, geometry and dimensions of the exemplary catheter shaft 102A is substantially identical to that for catheter shaft 102 except that the catheter shaft includes the inflation lumen 170 defined by an interior wall 172 extending from the inflation lumen 134 in the catheter hub 104A to the proximal portion 202A of the outer tubular element 200. The inflation lumen 170 has an interior lumen configured to permit the desired inflation of the outer tubular element, which allows the catheter to be used without a dilator for inflating or enlarging the outer tubular element 200. The proximal portion 202A is sealed around the catheter shaft and the distal portion of the inflation lumen 170, and withstands any fluid pressure expected within the lumen and the cavity 206 of the outer tubular element. The proximal portion of the catheter is supported by and sealed in the catheter hub 104A as would be done in a conventional catheter. The catheter is shown in FIG. 8 having the outer tubular element 200 deflated or in its collapsed configuration, pressing against the structural support 300, sandwiching or pressing the structural support 300 between the outer and inner tubular elements. Injecting fluid into the lumen 170 and increasing the pressure in the fluid system from the injection port 106 through the lumen 170 and into the cavity 206 within the outer tubular element 200 enlarges or inflates the outer tubular element 200, so that pressure is no longer applied to part or, in the illustrated example, all of the structural support element 300, and to reduce the stiffness and increase the flexibility of that portion of the catheter (FIG. 9).

Figure 10:
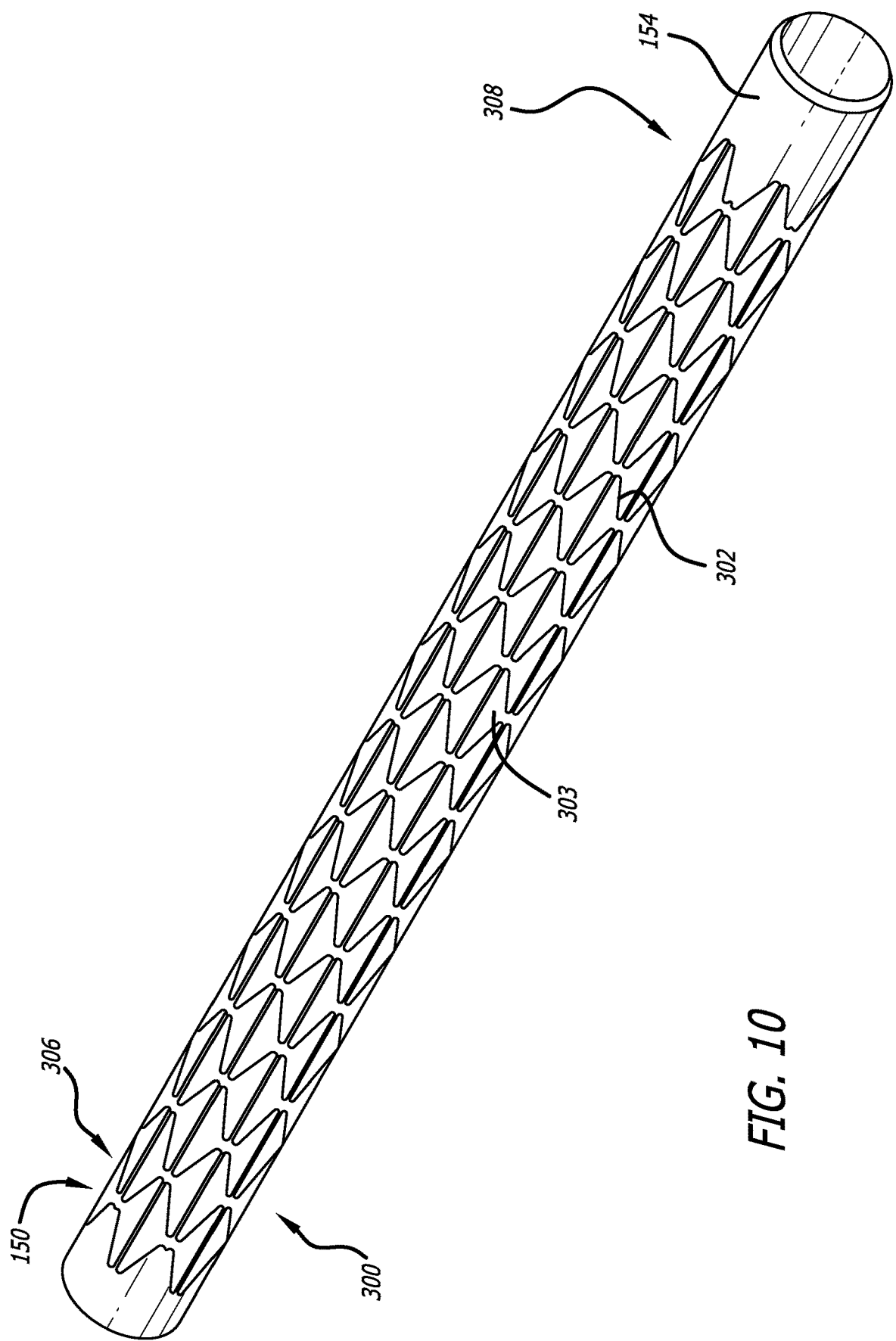
FIG. 10 is an isometric view of a portion of a catheter assembly.
Figure 11:
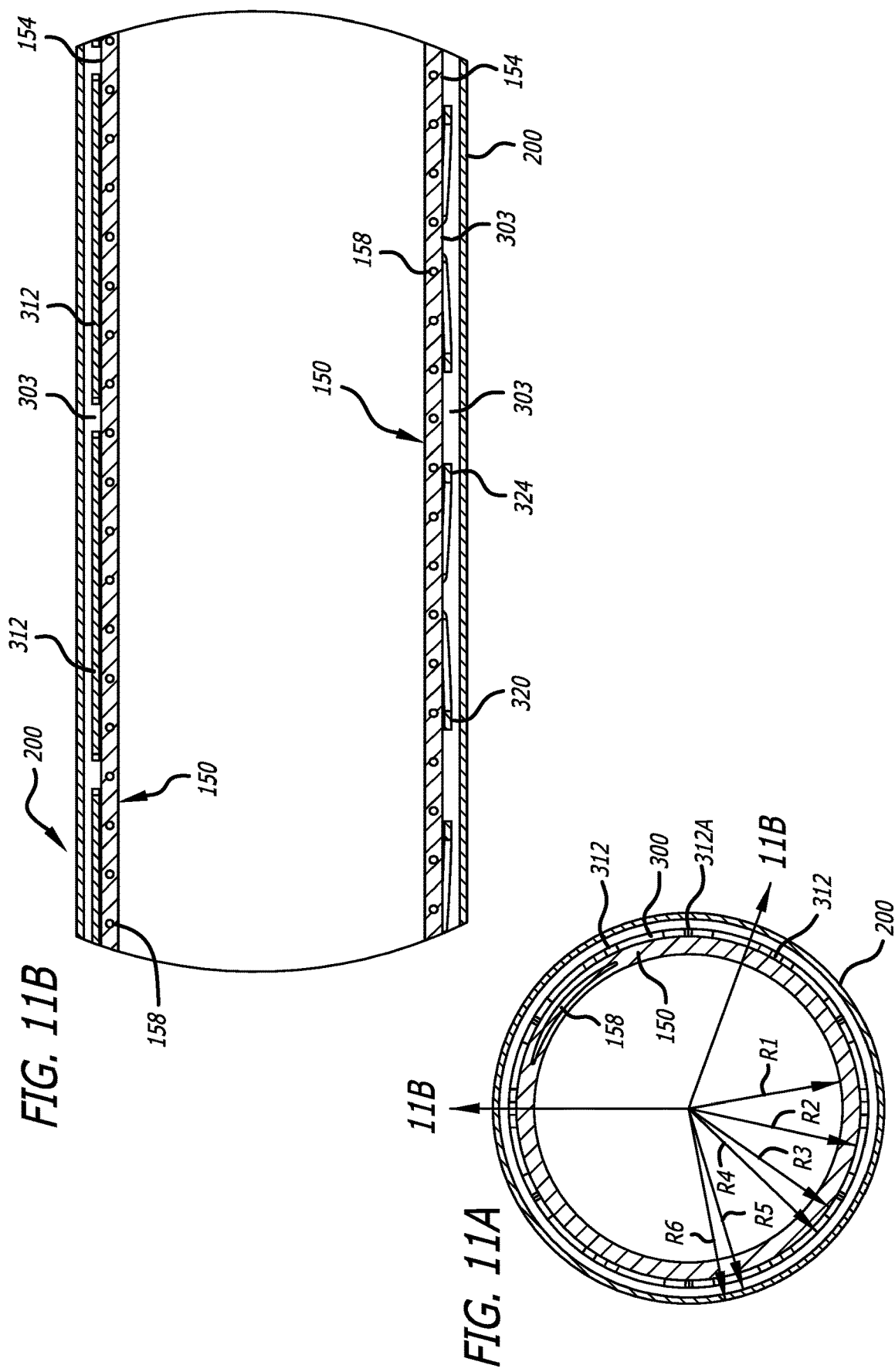
FIG. 11A is a transverse cross-section of the catheter portion of FIG. 10.
FIG. 11B is a detail of a section of the catheter portion of FIG. 10 taken at an angle as illustrated in FIG. 11A, though not necessarily at the axial location illustrated in FIG. 11A.

The structural support element 300 in the present example includes a repeating pattern (FIGS. 10-13). FIG. 10 shows the structural support element 300 extending along and around the adjacent portion of the inner tubular element 150 from a first end 306 to a second end 308. Because the structural support element is formed from a tubular mesh design, the first and second end portions are terminations of the pattern in between, and are not terminated with extra structures added to the end portions that are not present in the interior pattern.

The structural support element which has a repeating pattern can have the repeating pattern isolated into repeating groups or cells, while it is understood that a structural support element that does not have a recognizable repeating pattern will have a more complex structure that may not be amenable to identification of repeating groups or cells. The present support structure 300 (FIG. 12) includes a cell 310, which in the present example repeats circumferentially to provide six cells, and in the example illustrated in FIG. 10 repeats longitudinally to provide 11 cells plus a terminal boundary structure, which equates to approximately a half cell, depending on how the support structure is produced. Because the support structure is to be used in a catheter in the present example, it is desirable to exclude any free-ended limbs 302. In the illustrated examples, each limb terminates at both ends at respective ones or more other limbs.

In the structural support element 300, each cell 310 includes a first strut 312, which in the present configuration is a longitudinally-extending strut that extends longitudinally of the tubular support structure, and parallel to the axis of the inner tubular member 150. As shown in FIG. 10, the support structure and the tubular inner element 150 are concentric and coaxial over the length of the structural support element 300. The cell 310 also includes parts of adjacent longitudinal struts 312A and 312B. The longitudinal struts 312 extend parallel to each other, and are distributed circumferentially about the tubular support structure. In the present configuration, the longitudinal strut 312 is offset both circumferentially and axially relative to the adjacent longitudinal struts 312A and 312B.

Each longitudinal strut includes a first end 314 and a second end 316. Each of the first and second ends are joined or coupled to a pair of serpentine struts extending from opposite sides of the longitudinal strut. The first end 314 is joined or coupled to a first serpentine strut 318 on one side of the longitudinal strut, and to a second serpentine strut 320 on an opposite side of the longitudinal strut from the first serpentine strut 318. The first end 314 of the longitudinal strut forms a node at which three struts join or converge. Similarly, the second end 316 of the longitudinal strut 312 is joined or coupled to a third serpentine strut 322 on one side of the longitudinal strut, the same side as the first serpentine strut 318, and a fourth serpentine strut 324 on an opposite side of the longitudinal strut from the first and third serpentine struts 318 and 322. The first and second serpentine struts extend away from the longitudinal strut 314 and toward the third and fourth serpentine struts, which also extend away from the longitudinal strut 314 and toward the first and second serpentine struts, respectively.

The opposite ends of the second and fourth serpentine struts are joined or coupled at their respective ends to respective longitudinal struts 312B and 312A, the ends of which form their respective nodes. The second serpentine strut 320 is joined or coupled to a second end 328 of the adjacent longitudinal strut 312B, and the fourth serpentine strut 324 is joined or coupled to a first end 330 of the adjacent longitudinal strut 312A. A fifth serpentine strut 332 is coupled to the second end of the longitudinal strut 312B, and to the first end of a longitudinal strut 312'. A sixth serpentine strut 334 is coupled to the first end 330 of the longitudinal strut 312A, and to the second end of the longitudinal strut 312'. Therefore, in the present configuration, a cell 310 includes two longitudinal struts, as the outline is drawn formed from a full longitudinal strut and two halves, and the cell includes four serpentine struts formed from two complete serpentine struts and the sums of four partial serpentine struts. Each cell includes four nodes, and each node is the junction of three struts. As can be seen in the illustrated example, all struts are coupled or joined to at least two other struts, and the longitudinal struts are coupled to four serpentine struts, and each serpentine strut is coupled to two longitudinal struts. This arrangement provides a moderate degree of interconnectivity, allows free-form radial expansion and contraction (before the support structure is combined with any other structure), and allows free-form longitudinal expansion and contraction. The amount of expansion and contraction is determined in part by the starting angle of an angle 336 when the support structure is first formed. For example, when the support structure is first formed with a relatively small angle 336, greater radial expansion is permitted than radial contraction because the starting angle is small. Conversely, when the first support structure is first formed with a relatively large angle, the remaining radial expansion is less, and the available radial contraction is greater than for a smaller starting angle 336.

The structural support member 300 at any given transverse cross-section is configured to have at least two struts in the cross-section, and in many designs will have at least three struts, as three points define a plane. In the exemplary structural support member 300, a transverse cross-section will intersect at least six struts 312 (FIG. 11A). The six longitudinal struts 312 are distributed substantially uniformly about the circular support member 300. Such a transverse cross-section can be visualized in FIG. 12 at either of the lateral sides (as visualized in FIG. 12) of the cell 310. However, at other transverse cross-sections axially along the structural support member, additional struts will be visible, for example 12 when the transverse cross-section intersects a node such as 328, and for example 24 when the transverse cross-section intersects intermediate portions of the serpentine struts. Additionally as would be seen in a transverse cross-section, the longitudinal struts are different size from the serpentine struts, and have a larger cross-sectional area. There are more of the smaller struts than there are larger struts, and in the present example twice as many smaller struts than larger struts in a given cell. As can also be seen in FIG. 12, all of the struts are connected, and in the present example interlinked or interconnected so that each strut is connected to at least two other struts. Also as can be seen in FIGS. 10 and 12, no single longitudinal strut extends the entire length of the structural support member without a bend or transition to another longitudinal strut. Additionally, in the illustrated example, no single element of the structural support member, in the present example no single strut, extend the entire length of the structural support member without a bend or transition to another element/strut.

In the present examples of support structures, the support structures are formed from solid tubular elements having a constant wall thickness (thereby providing a substantially constant thickness for all of the struts) and laser cut in a manner similar to the formation of stents to form the tubular mesh illustrated in FIG. 10 or in FIGS. 16 and 17. In the example of the support structure 300, the angle 336 formed during formation of the support structure may be a small acute angle, for example as small as several degrees (1-2°), or a large acute angle, for example as large as 85-89°. Larger angles (obtuse) are possible as well and provide structural support, but do not provide the same structural support once incorporated into a catheter assembly as does the configuration of the support structure 300 having an acute angle 336 when initially formed.

In the configuration of the structural support produced using the pattern shown in FIG. 12, the angle 336 is selected to be approximately 8°. In the final assembled configuration of the structural support shown in FIG. 10, the angle represented by 336 is approximately 24° after expanding the support structure.

The support structure 300 in the present examples is formed from a solid tubular element having a wall thickness of 0.003 inch. The structural support 300 is then formed by laser cutting, in a manner similar to that used for forming stents, so that all of the struts have a thickness 338 equal to the starting wall thickness of the solid tubular element. In the present example, the width 340 of the longitudinal strut is approximately 0.004 inch, which is approximately twice as much as the width 346 of the serpentine strut, which is approximately 0.002 inch, in the present example, and greater than the thickness, while the thickness is approximately 0.003 inch, which is greater than the width 346 of the serpentine struts. Consequently, the longitudinal struts resist bending more than the serpentine struts. The geometry of the cells, the wall thickness of the struts, the width of the struts, and the angle 336 contribute to determining the stiffness, flexibility or resistance to bending of the support structure, in free-form separated or apart from the catheter assembly. Such stiffness, flexibility or resistance to bending of the support structure is carried into the assembly in the catheter, and will exhibit similar characteristics in the catheter assembly. The thicknesses and widths of the struts can be selected to be between approximately 0.0005 inch and 0.0100 inch. Additionally, the stiffness, flexibility or resistance to bending of the catheter assembly in the area of the support structure 300 is determined in part by the stiffness, flexibility or resistance to bending of the support structure per se, as well as the engagement and interaction of the components of the assembly with each other, including surface areas of contact between the structural support and adjacent surfaces. When such surface areas of contact are reduced or removed, such as by inflation or enlargement of the outer tubular element, the various contributions to stiffness, flexibility or resistance to bending are reduced but the inherent stiffness, flexibility or resistance to bending of the support structure per se remains. Therefore, the design or pattern of the support structure determines not only the stiffness, flexibility or resistance to bending of the support structure per se, but also the contribution to the stiffness, flexibility or resistance to bending of the catheter based on the interaction of the support structure with adjacent components. In the configuration described and illustrated in FIGS. 10-13, the structural support member has cells with the surfaces facing the outer tubular member wherein each cell has a facing surface area of about 0.00075824 in., and likewise with the surface of each cell facing the inner tubular member. Also in the configuration illustrated in FIGS. 10-13, each limb has an outer surface facing the outer tubular member and an inner surface facing the inner tubular member where the inner and outer surfaces are relatively uniformly smooth or flat, for example as illustrated in FIG. 13, to the extent permitted by the manufacturing techniques used for making the support member. Alternatively, as described herein, the outer and/or inner surface of at least one limb may be other than smooth, and may include discontinuities or other configurations that form structures extending outward from a respective surface for engaging a respective adjacent structure to change the relative contribution to the stiffness, flexibility or resistance to bending of the assembly at least in the area of the outward extending structures.

The effect of interaction between the support structure 300 and any adjacent components is affected in part by the radial position of the support structure. With a flexible inner tubular member 150 having an inside radius from the center R1 and an outside radius from the center of R2, the support structure 300 will be on or closely adjacent the outside surface 154 of the inner tubular element. In the present examples, the inside diameter of the support structure 300 is represented by radius from the center R3 which is substantially equal to the radius R2, so that the support structure contacts the outside surface 154 of the inner tubular member. The outside radius R4 of the support structure 300 is then determined by the wall thickness of the support structure. Additionally, the inside diameter of the outer tubular member 200 is represented by the radius from the center R5, and the outside diameter is represented by the radius R6, both of which are given while the outside tubular element is enlarged or expanded or inflated. The maximum inside diameter of the outer tubular element in a relaxed or collapsed state corresponds to substantially R4, namely the outside diameter of the support structure, and the maximum outside diameter of the outer tubular element in the relaxed or collapsed state is substantially R4 plus the wall thickness of the outer tubular element. The minimum inside diameter of the outer tubular element when in the collapsed or uninflated state will depend on the flexibility of the material of the outer tubular element, and the relative surface area of the open areas between struts that will allow the material of the outer tubular element to extend between the struts. The radius values of the structural support 300 are set forth in the Table I below:

TABLE I

| | |
|---|---|
| R1 | 0.044 in. |
| R2 | 0.055 in. |
| R3 | 0.055 in. |
| R4 | 0.058 in. |
| R5 | 0.060 in. |
| R6 | 0.063 in. |

Resistance to bending in tubular structures such as catheters generally occurs on an outer surface of the tubular structure. As illustrated in FIG. 11A, the support structure and the outer tubular element are positioned at the outer reaches of the assembly, and the mechanism in the form of the structural support that is used in the present examples to provide variable stiffness is located in the area of or on an outside surface of the inner tubular member, for example where the mechanical properties of the structural support can have a strong effect. As illustrated in FIG. 11A, the structural support is in the area of approximately 95% of the maximum outer diameter of the catheter. Therefore, the effect of the structural support on the flexibility or stiffness of the portion of the catheter at which it is placed by having it applied at outer areas of the catheter relative to the center axis, for example between 50% and 100% of the overall outside diameter of that portion of the catheter. Additionally, the function of surface area of contact, such as between the structural support and the outer surface 154 of the inner tubular member 150, and/or between the structural support 300 and the outer tubular element 200, is improved by positioning the structural support element at a higher radial position than a lower radial position, because the surface area available increases with the square of the radius. Therefore, placing the structural support element outside the inner tubular element 150 enhances the contribution of the surface area of contact and frictional resistance developed between the structural support and any adjacent surfaces.

Figure 14:
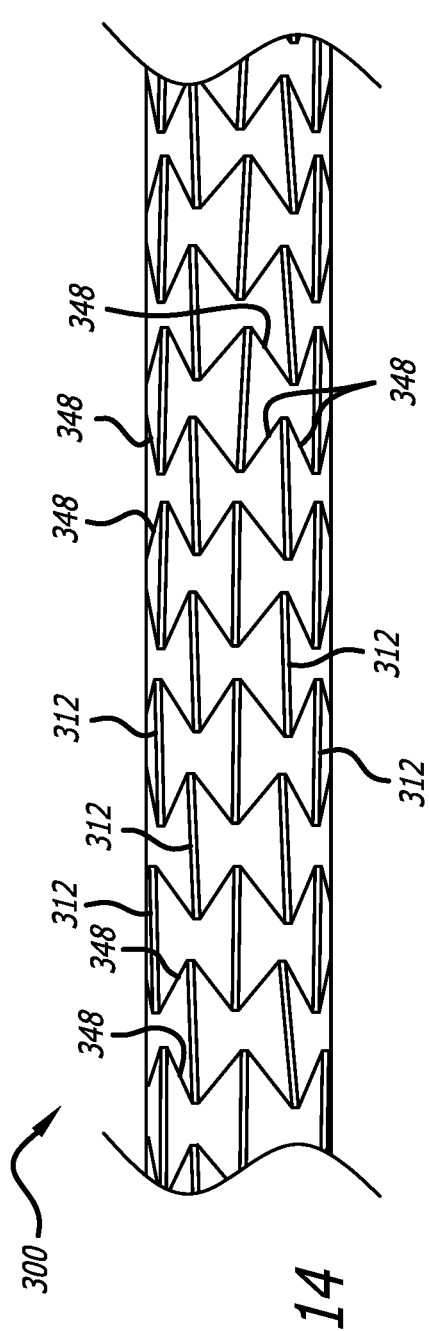
FIG. 14 is a schematic representation of a tubular mesh formed using the pattern of FIG. 12.

FIG. 14 illustrates a portion of the structural support 300 in an approximately neutral state, for example after assembly onto an inner tubular element and formed into a catheter assembly, ready for use though after some residual movement as not all of the longitudinal struts 312 are precisely parallel and the serpentine struts, labeled generically as 348, have adjusted accordingly. The longitudinal struts are not in compression or tension and are substantially regularly spaced from each other, and the serpentine struts 348 also are not in tension or compression, but such condition will depend on the initial magnitude of the angle 336 (FIG. 12) when the support structure was initially produced and its condition when positioned on the inner tubular element.

Figure 15:
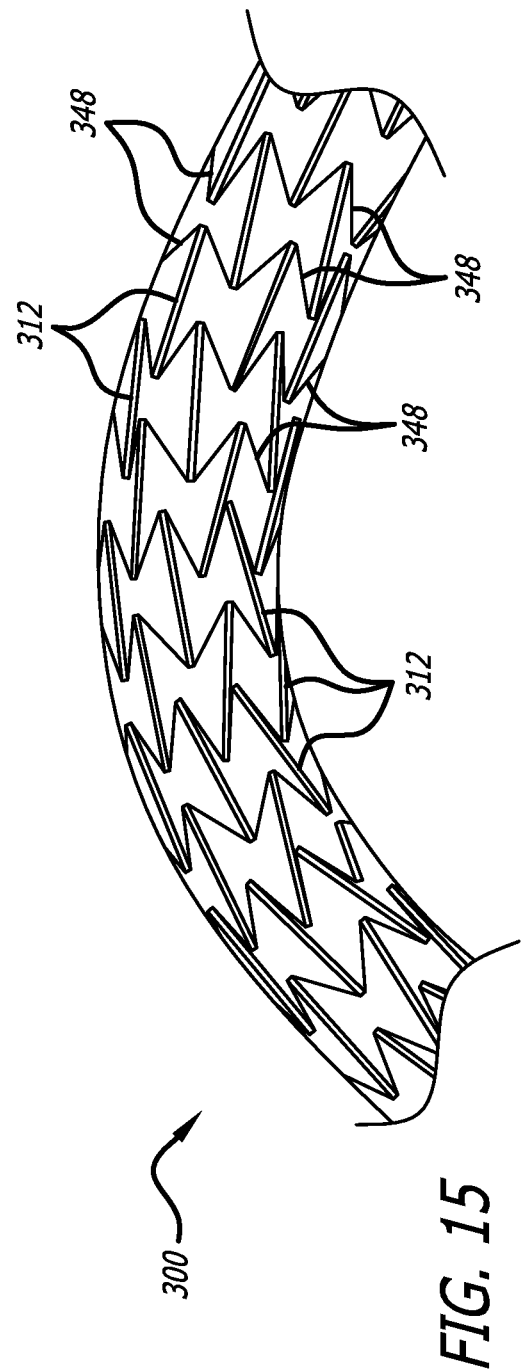
FIG. 15 is a schematic representation of the tubular mesh of FIG. 14 in a loaded or bent configuration.

The struts are free to bend relative to each other with minimal applied force when in an unconstrained state, such as when the outer tubular element 200 is enlarged or inflated, because of their relatively small thicknesses and widths. When the structural member 300 is bent in its unconstrained state based on an applied bending load, the struts rearrange themselves to accommodate the changed mechanical condition, as schematically represented in FIG. 15. In FIG. 15, the longitudinal and serpentine struts have rearranged themselves to the lowest energy configuration available with the imposed curvature, preserving the length and interconnection of the struts. In the concave portion of the support structure, the longitudinal struts are brought closer together, which approach is limited by the serpentine struts which are put in tension, and the angle 336 becomes more acute. The acute angle between adjacent longitudinal and serpentine struts helps in the force transfer between longitudinal struts as they rearrange themselves. On the convex side of the bend, the longitudinal struts tend to separate in some areas, subject to the restrictions of the attached serpentine struts and nearby longitudinal struts.

When the support structure is incorporated into catheters as described herein, rearrangement of the struts occurs with relatively low force required when the structural support element is unconstrained, or in a tracking mode, such as when the outer tubular element is enlarged, expanded or separated from the structural support element. When the structural support is constrained, such as when the catheter is in a support mode, such as when the outer tubular element is collapsed or pressing against the structural support element, rearrangement of the struts either does not occur or occurs at a much higher applied force compared to that in the unconstrained condition. The relatively high degree of interconnectedness between the struts allows for flexibility of the support structure to bend, but the points of interconnection between struts limit the degrees of freedom in which the struts may rearrange themselves. These factors can be changed by increasing or decreasing the number of nodes per unit length, increasing or decreasing the number of struts at a node, separate the struts into groups of struts and have one group of struts connected at more nodes and another group of struts connected at fewer nodes, and similar variations.

In one exemplary catheter configuration, the length of the catheter distally from the catheter hub is approximately 36 inches or approximately 90 cm, and the length of the variable flexible portion with the support structure 300 and the outer tubular element 200 is approximately 8 inches or 20 cm. The portion of the catheter shaft that can include a variable flexible portion can be greater or lesser than this example.

The structural support element can take a number of configurations, especially considering the number of stent configurations that have been developed. As one example of an alternative structural support element (FIG. 16), a support element 400 includes a cell 402 forming the basis of a repeating pattern, extending longitudinally and circumferentially. The cell 402 forms part of a helical pattern where the cell includes a rectangular frame 404 having four sides and defining an opening 406. Each cell is separated from a longitudinally adjacent cell by a laser cut separation, forming the helically wound ribbon. The openings 406 receive flexible portions of the outer tubular element when collapsed or pressing against the structural support element, thereby helping to limit or restrict movement by mechanical engagement or frictional resistance. In an alternative configuration, the cells 402 can take a non-helical configuration, for example with two or more circumferentially adjacent cells connected together as shown in FIG. 16, or connected at one or more nodes (not shown) providing greater flexibility between circumferentially adjacent cells. Longitudinally adjacent cells can also be connected at one or more nodes (not shown) as a function of the desired flexibility in the constrained and unconstrained states.

In another example of a structural support element (FIG. 17), structural support element 410 is formed from a helically cut tube or helically wound ribbon. The structural support element includes a longitudinally extending projection 412 in one part of the winding extending into a complementary longitudinally extending cavity for 14 in an adjacent winding. Windows or apertures (not shown) may be provided interior to edge surfaces of windings of the helix to provide frictional engagement surfaces with the outer tubular element.

Adjustment of the flexibility or stiffness of a portion of the catheter 100/100A/100B is used to allow the catheter to track a path in a vessel, for example over a guidewire or other guide device, and alternately to provide structural support within the vessel when desired, for example to support passage of an intervention device or the like. In a tracking mode, the inner tubular member is flexible for easy track ability, and kink resistant to minimize damage during use and to provide suitable force transmission along the long axis of the catheter for pushing and advancing through the vessel. In the tracking mode when the structural support element is flexible and not constrained, the struts of the structural support element are free to bend, adjust and realign and move freely, subject to the positioning of adjacent struts. The struts align to the lowest energy configuration possible. When the catheter is positioned as desired, the structural support element is pressed between the outer tubular element and the inner tubular element, thereby becoming constrained and the struts are no longer free to move relative to each other or relative to the adjacent surfaces without a significant amount of force. In the constrained or supportive configuration, the structural support resists bending of the catheter, reducing its flexibility and increasing its stiffness. The configuration is analogous to a clutch, whereby disengaging the outer tubular element from the structural support element and further away from the inner tubular element allows free motion of the structural support element and the struts therein, as may be limited by the bending limitations in the structural support element per se. Applying a vacuum or negative pressure or removing inflation fluid from inside the outer tubular element engages the clutch structure, mechanically linking the outer tubular element, the structural support element, and the inner tubular element, rendering the catheter structure in the area of the structural support element less flexible, and better able to support devices to be passed through the catheter lumen.

In operation, a fully assembled catheter assembly 100/100A/100B is placed in a tracking configuration by injecting fluid into the cavity 206 within the outer tubular element 200, or otherwise increasing the pressure in the cavity. The tubular element is expanded or enlarged so that the outer tubular element releases or mechanically disengages from the structural support element 300, thereby reducing or eliminating the frictional resistance to bending with the structural support element 300. The pressure is maintained within the cavity 206 or the outer tubular element is otherwise maintained in the inflated or enlarged configuration. The catheter assembly is introduced into a body lumen, for example through a trocar, introducer, or other structure and moved through vasculature 500 (FIGS. 18-20), for example with the assistance of a guidewire 502. As the guidewire 502 is moved to a new position, as illustrated in FIG. 18, the catheter 100/100A/100B is advanced over the guidewire in the catheter tracking mode. When the catheter has reached the desired location, such as illustrated in FIG. 19, the catheter assembly can be placed in the support mode by withdrawing fluid or applying negative pressure to the lumen in fluid communication with the cavity 206, or by allowing the recoil or memory of the inflated outer tubular element 200 to return toward its relaxed state, contracting into mechanical engagement or contact with the structural support element, and applying pressure to the structural support element and clamping the structural support element between the outer and inner tubular elements. The flexible wall of the outer tubular element can also bulge into the openings 303 between struts of the structural support element 300 (and possibly contacting the outer surface 154 of the inner tubular element), thereby increasing the mechanical engagement or frictional force resisting movement of the structural member relative to adjacent surfaces, and thereby increasing the stiffness and support of the catheter assembly. The reinforcement, for example the coil 158 in the inner tubular element, resists deformation of the inner tubular member, for example due to any compressive loading from the outer tubular member, either alone or in combination with any bending load. In the examples herein, the inner tubular element is substantially incompressible for the pressure loads that would be experienced under normal operating conditions. The guidewire can then be withdrawn and replaced by an interventional or other device 504 (FIG. 20) to carry out the desired procedure, which may also have its own structural support element and flexible outer tubular element for adjustable support. The catheter assembly can then be withdrawn after returning the catheter assembly to a tracking mode, which may include reinserting a dilator, and then withdrawn in accordance with conventional methods.

Before the catheter is introduced into a lumen, and as the catheter is transiting a body lumen such as depicted in FIG. 18, the catheter can be in the tracking or flexible mode in the area of the structural support member. In that configuration, the catheter takes a number of shapes configurations, for example after manufacture the catheter can be straight, including the variable stiffness region in the area of the structural support member, and while the catheter is transiting the body lumen, the catheter including the variable stiffness region will take shape configurations conforming to the body lumen. In those shape configurations, while the structural support member is released or free to adjust its shape, the structural support member can have a number of configurations. One configuration is illustrated in FIG. 15, in which the struts have rearranged themselves to the lowest-energy configuration imposed on it by the wall of the inner tubular member. However, when part or all of the structural support member takes on a fixed shape configuration, for example by being sandwiched, pressed or squeezed between the inner and outer tubular elements, the structural support member and the surrounding catheter structure maintains the fixed shape configuration, which is also the configuration of the surrounding lumen wall. As a result, the variable shape portion of the catheter adopts the shape of the surrounding lumen and does not substantially change that shape until released. For example, once the catheter has been positioned as desired while in the tracking, flexible or released mode, such as in FIG. 19, the variable shaped portion of the catheter takes on a second shape configuration different than previous shape configurations while the catheter was transiting the lumen. When the structural support element is sandwiched, laminated or fixed in the second shape configuration, the variable shaped portion of the catheter applies little if any force 506 or pressure on the lumen wall as a result of the transition from tracking or flexible mode to the support or fixed mode in the second shape configuration. If the catheter were theoretically able to be lifted from the body lumen without having to transit the lumen passageway again, it would be seen that the catheter maintains the shape of the lumen it has adopted as though it has shape memory. In other words, the variable shaped portion of the catheter in going from the tracking or flexible mode to the support or fixed mode applies little if any force on the adjacent lumen wall. Such results can be illustrated with a three-point bending flexural test with the variable shaped portion of the catheter arranged in a second shape configuration, and the force measured before and after fixing or pressing the structural support member would not be very different. For example, the force difference could be approximately 20%-25%, and could be in the range of 15-25%, and with the configuration of the structural support member 300 illustrated in FIGS. 10-13, can be less than 10% (force after fixing or pressing the structural support member minus the force before fixing or pressing the structural support member divided by the force before).

A difference between the tracking mode and the support mode can be illustrated by comparing forces used to deflect a straight catheter assembly at the area of the variable stiffness. With a substantially straight catheter, a middle portion or other selected portion of the variable stiffness area can be bent for an inch or other selected distance by having a normal force applied and measuring the force required to move the selected distance. The force is measured when the catheter is in the tracking mode or a more flexible state, and when the catheter is in the support mode or a more rigid or stiff and less flexible state. In one example where the outer tubular element is completely spaced apart from the underlying structural support member and the catheter bent 1 inch, the measured force is about 0.38 pounds force (lbf.). The catheter is then returned to a straight configuration, and placed in the support mode or with the outer tubular member pressing against the structural support member and bent 1 inch. The measured force is about 0.54 pounds force. A Bend Force Ratio of the Support Mode Force divided by the Tracking Mode Force in this example is approximately 1.42. Ratios greater than one provide a desirable catheter configuration, and ratios of approximately 1.2 and above are more desirable.

The catheter assembly can be assembled in a number of ways, including in part conventional methods for assembling a catheter. In one method (FIGS. 21-28) a mandrel assembly 600 is used, similar to conventional assembly apparatus. The mandrel assembly is selected to have a mandrel 602 to provide the desired size catheter with the selected internal diameter. In one process, the inner tubular member 150 is assembled by sliding a polytetrafluoroethylene liner over the mandrel 602 and applying a braid or coil reinforcement over the liner. An extrusion is applied over the braid or coil reinforcement, after which the layers are securely laminated inside a removable heat shrink tube to merge all of the components together into the inner tubular member 150. One or more holes or apertures 164 are formed in the laminate, extending completely through, in the area where the structural support element will be positioned. The structural support element is formed for example by focused laser cutting a monolithic metal tube according to the desired pattern. The structural support element 300 is placed over the tubular member 150 and positioned as desired. It may be tack bonded at its distal and proximal ends to secure it to the inner tubular member for assembly.

Figure 23:
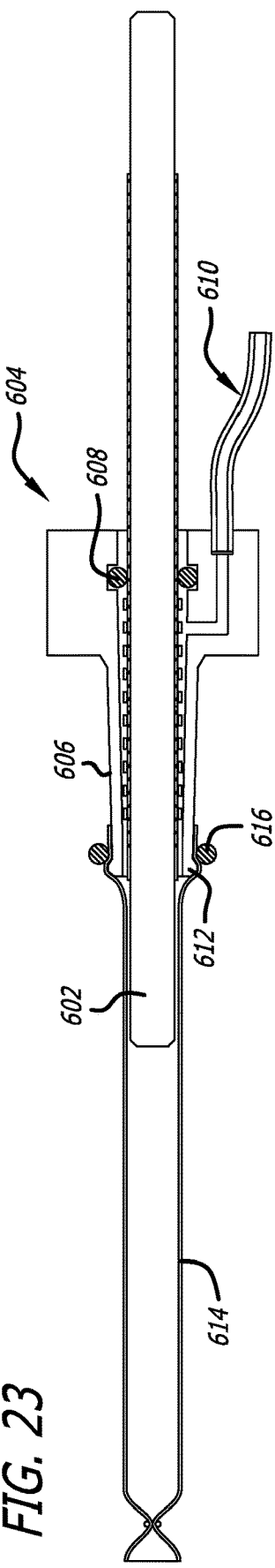
FIG. 23 is a schematic representation of the assembly of FIG. 22 with a balloon inflation and assembly apparatus.
Figure 24:
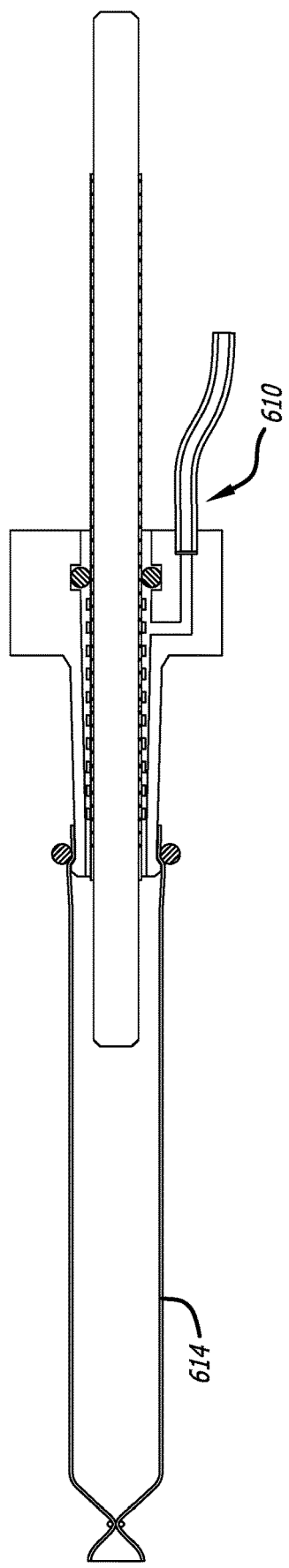
FIG. 24 is a schematic representation of the assembly of FIG. 23 with a tubular element inflated.
Figure 25:
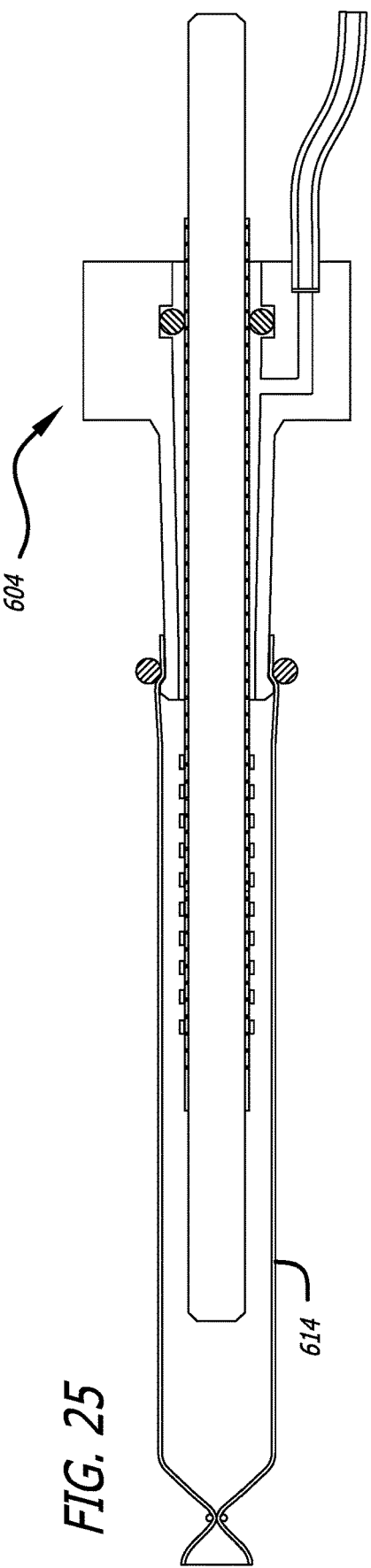
FIG. 25 is a schematic representation of the assembly of FIG. 24 with the mandrel assembly being inserted into the inflated tubular element.
Figure 26:
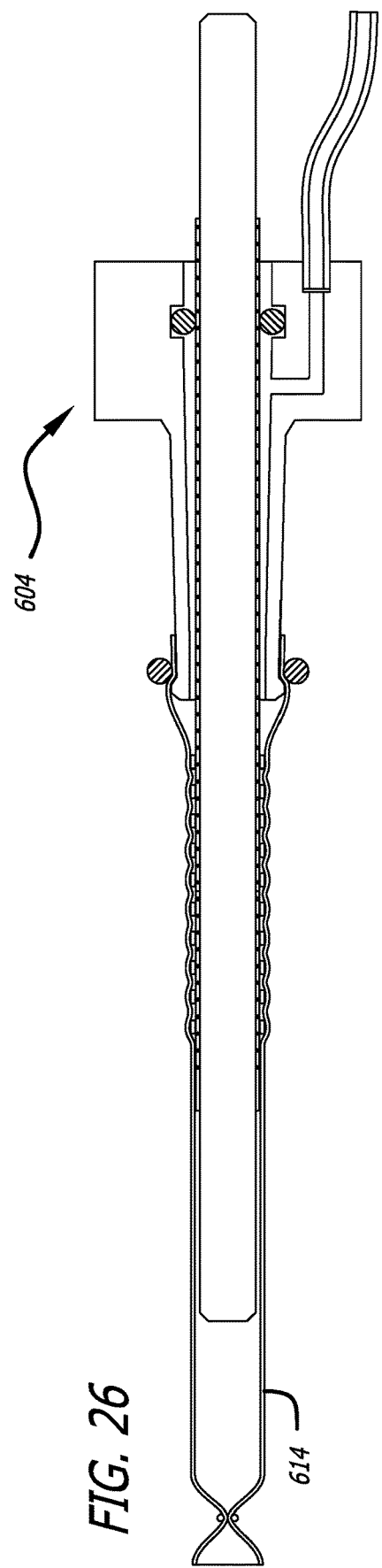
FIG. 26 is a schematic representation of the assembly of FIG. 25 with the mandrel inserted into the inflated tubular element and the tubular element deflated.
Figure 27:
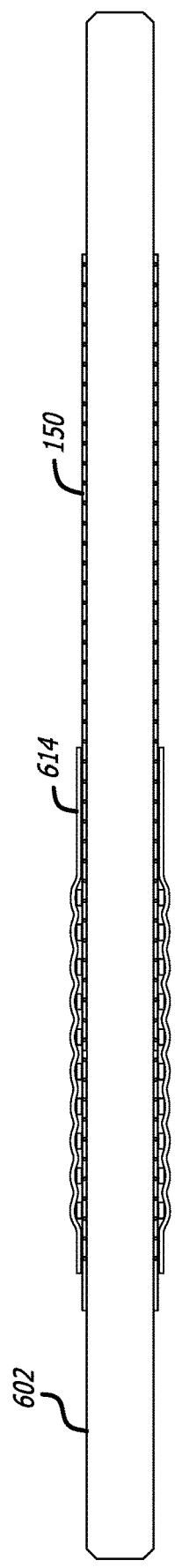
Figure 28:
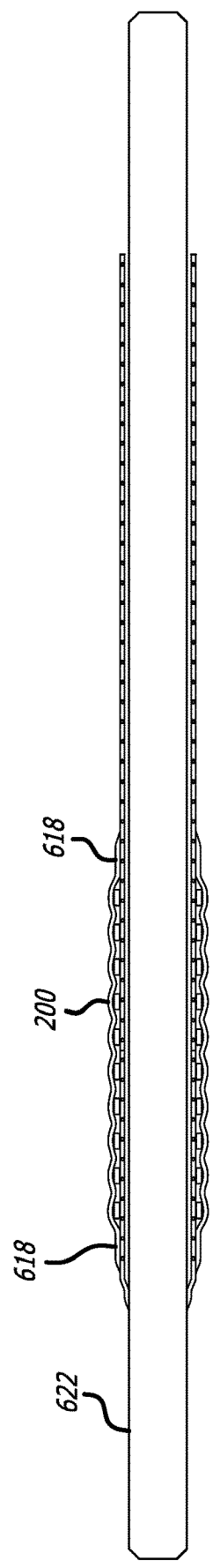
FIG. 28 is a schematic representation of a further mandrel assembly with the catheter assembled there on configured to provide the catheter for an interference fit with a dilator assembly.
Figure 31:
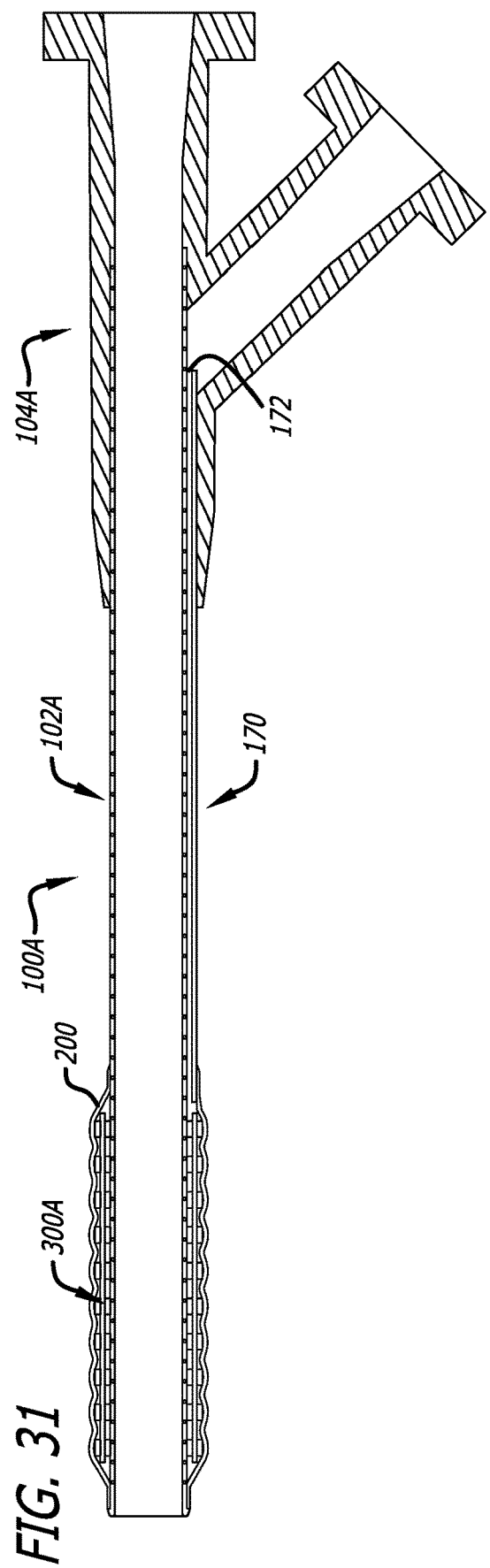
FIG. 31 is a longitudinal cross section of the catheter assembly of FIG. 29 with a portion of the catheter assembly reduced or deflated or constricted.
Figure 32:
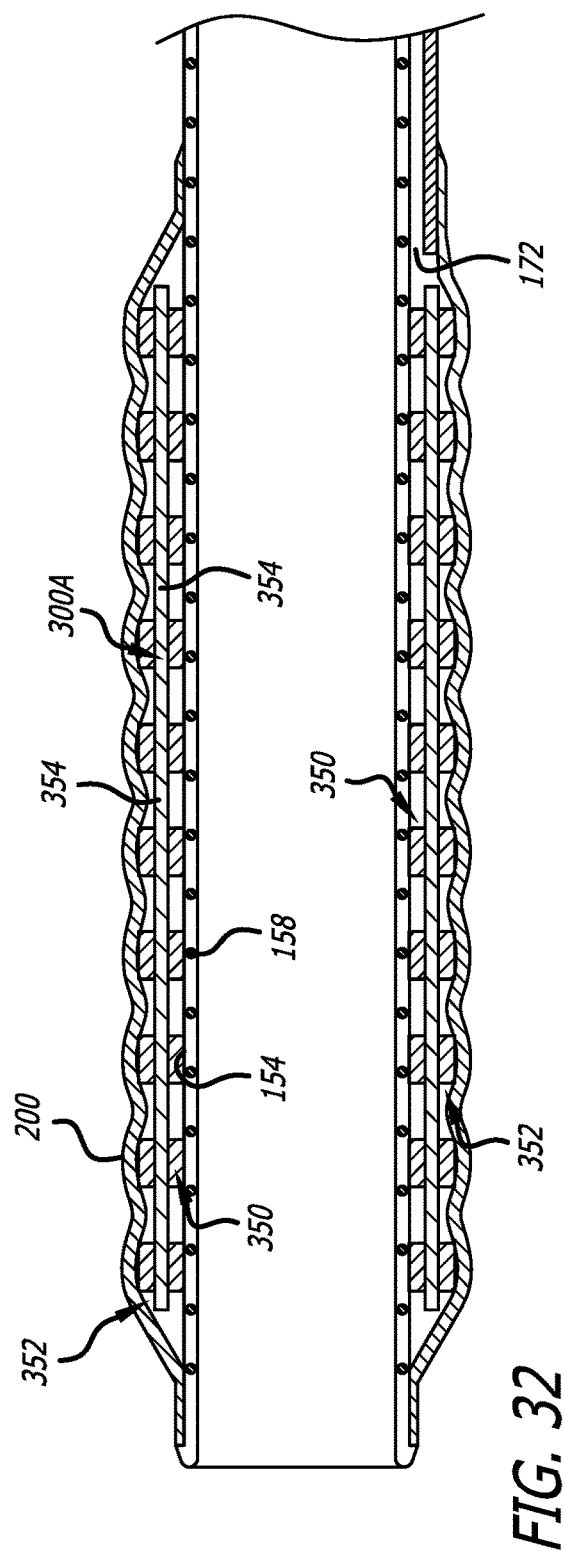
FIG. 32 is a detail of a distal end portion of the catheter of FIG. 31.
Figure 34:
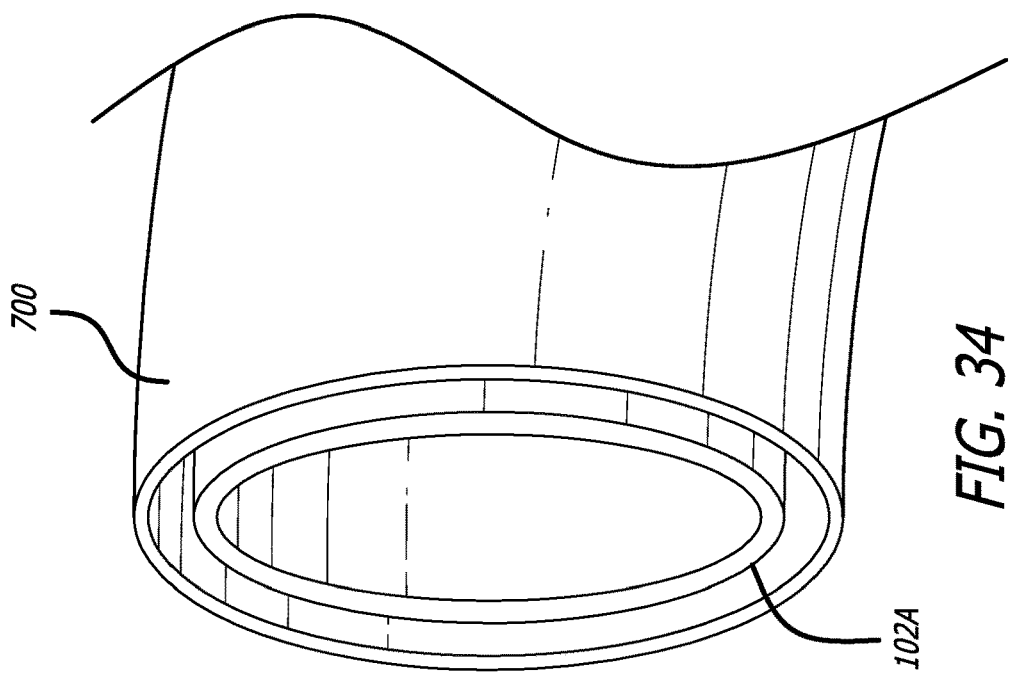
FIG. 34 is an isometric and transverse cross-sectional view of a portion of the catheter assembly of FIG. 33.
Figure 33:
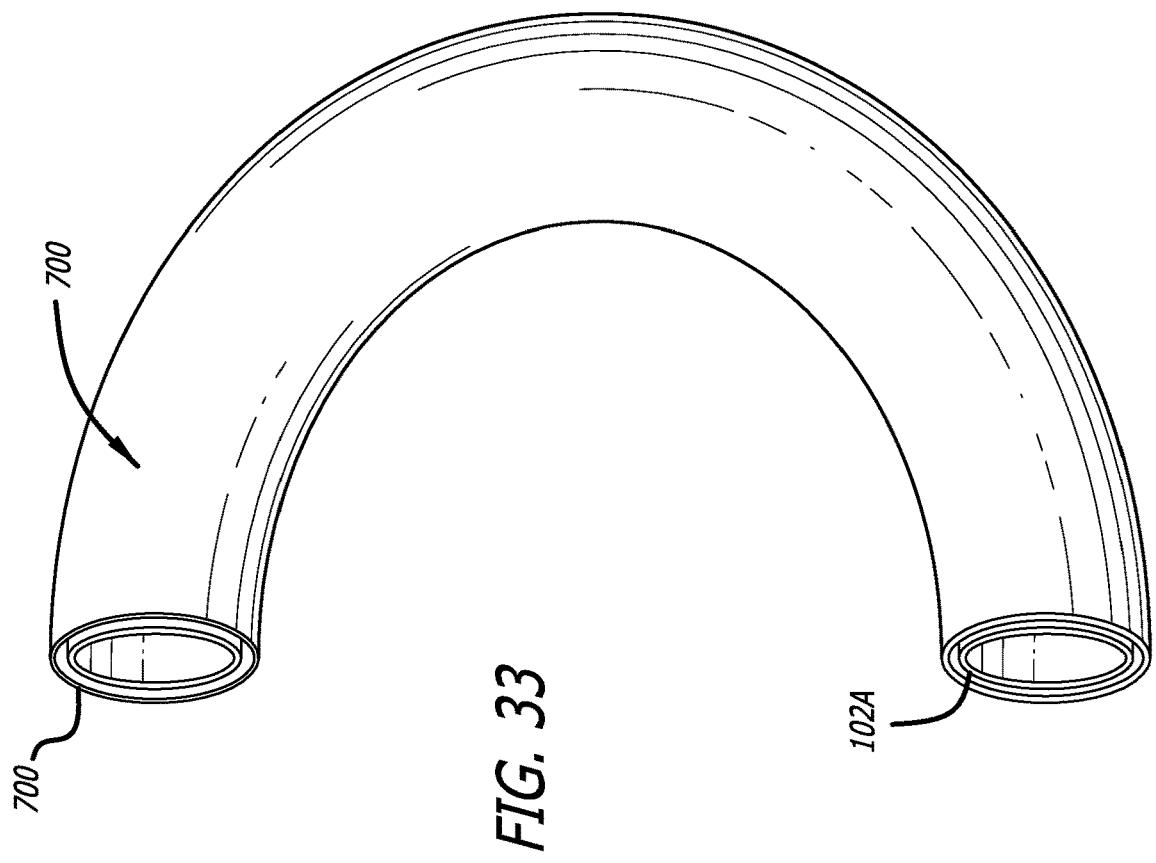
FIG. 33 is a schematic and plan view of part of a catheter assembly showing an alternative inflation lumen over a portion of the catheter wherein the alternative inflation lumen can provide structural support for the adjacent portion of the catheter.

The mandrel with the inner tubular member assembly is then inserted into a tubular loading tool 604 (FIGS. 23-26) with the structural support element within a barrel 606 of the loading tool. The barrel 606 can include multiple parts, for example to be separated for inserting the mandrel and inner tubular member. The loading tool includes an O-ring seal 608 at a distal portion for providing an airtight seal around the inner tubular member and mandrel. The loading tool 604 also includes a pressurization port 610 proximal of the seal 608 for providing pressurized air or other pressurized fluid around the outside of the inner tubular element extending toward the distal end of the tubular element. The barrel 606 includes an annular lip or ridge 612 at a distal end for receiving one end of an inflatable tubular element 614 to be sealed around the barrel with an O-ring seal or other seal element 616. The parts of the barrel can be separated and the proximal portion placed over the proximal portion of the mandrel and inner tubular element, and the distal portion placed over the structural support element and the two parts brought together and sealed. The inflatable tubular element 614 is applied to the distal portion of the barrel and sealed with the seal 616. As illustrated in FIG. 23, the relaxed state of the inflatable tubular element 614 is less than the outer diameter of the structural support element 300, and FIG. 23 shows the relationship schematically and greater spacing between the inflatable tubular element and the mandrel 602 for ease of illustration. The opposite end of the inflatable tubular element is closed, for example with a closure knot, clip, ligation or the like. Inflation pressure is then applied at the inflation port 610 to inflate the inflatable member 614, as illustrated in FIG. 24, for example approximately 40 psi and possibly as much as 80-100 PSI. The applied pressure inflates or expands the inflatable member diametrically. When the inflatable member is stabilized, the mandrel and inner tubular member assembly are slid inside the outer tubular element 614 (FIG. 25) so that the inflatable member is suitably positioned over the structural support member and an underlying assembly. Pressure is then removed from the inflatable member, for example through the pressurization port, and the inflatable member collapses around the structural support member and the adjacent portion of the inner tubular member (FIG. 26). The assembly is then removed from the loading tool 604 (FIG. 27) and the inflatable member trimmed to the desired length around the structural support member. The outer tubular element 200 is then bonded at 618 and 622 the inner tubular element, and further trimmed if necessary (FIG. 28). The mandrel 602 is then replaced by a smaller mandrel 622, and the tip of the catheter is re-flowed to reduce its diameter to that of the smaller mandrel, to provide the desired interference fit with an appropriate dilator tip. The mandrel 622 is then removed, and the tubular assembly bonded or otherwise secured at its proximal end to a proximal hub, for example catheter hub 104 (FIGS. 1-2).

With selection of suitable material for the outer tubular element 200, resilience or pressure memory can be incorporated into the outer tubular member on assembly, for example by using a relaxed tubular member having an inside diameter in the relaxed condition less than the structural support member and possibly even less than the inner tubular element. Inflation of the inflatable material allows easy assembly of the outer tubular element onto the catheter assembly to provide the desired resilience so that the outer tubular member can apply an appropriate pressure to the structural support element.

Other structures and assemblies can be used in addition to or as alternatives to those described herein for controllably changing the support provided in a lumenal assembly, for example a catheter assembly such as those described herein. In the examples shown in FIGS. 29-44, structures with the same reference numbers have the same or similar structures and functions as described herein. In one exemplary alternative, described in conjunction with FIGS. 29-32, an assembly for controllably varying a stiffness of a catheter assembly 100A includes a medial member that is an assembly having a structural support assembly 300A. The structural support assembly 300A includes an inner structural support member 350 extending about an adjacent portion of the catheter wall 154 in a manner similar to the structural support 300 described herein. The inner structural support member 350 can be configured to have the structure and function of any of the structural support members described herein, and in the present configuration extends circumferentially completely around the adjacent portion of the catheter lumen.

In the illustrated configuration in FIGS. 29-32, the structural support assembly 300A includes an outer structural support member 352 laterally outward of the inner structural support member 350. In the present example, the outer structural support member 352 extends circumferentially around the adjacent portion of the catheter lumen, outboard of the inner structural support member, and interior to the adjacent surface 208 of the inflation lumen 200. The outer structural support member 352 can have a structure and function identical to that of the inner structural support member 350, or it can have a structure and/or function different than that of the inner structural member. The outer structural support member 352 can be configured to have the structure and function of any of the structural support members described herein.

The structural support assembly 300A may also include, but need not include, a secondary material such as a sleeve 354. The sleeve in the exemplary configuration extends and is positioned between the inner and outer structural support members, coaxial therewith, but may be inside or outside both structural support members. In the present example, the sleeve material is a flexible material, and may include surface characteristics allowing free sliding movement of the adjacent structural support members, or providing frictional engagement to reduce free sliding movement of the adjacent structural support members relative to the sleeve material. The sleeve may be a continuous tubular element, may be formed with a porous configuration, may be a random or non-random mesh material, or may have other configurations as desired.

The configurations illustrated in FIGS. 29-30 show the inflation lumen in an expanded or inflated configuration, providing a reduced measure of structural support to the assembly. When inflation fluid is removed or allowed to escape or evacuate the interior of the inflation lumen 200, spacing between the inner and outer structural support elements and the sleeve and the adjacent surfaces of the inflation lumen and the catheter lumen decreases. With sufficient removal or outflow of inflation fluid, the inflation lumen 200 may contact the adjacent surfaces of the outer structural support member 352. Additionally, interior surfaces of the outer structural support member 352 may contact the outer surface of the sleeve 354, and the inner surface of the sleeve 354 may contact the adjacent outer surfaces of the inner structural support member 350. Interior surfaces of the inner structural support member may contact the adjacent surface 154 of the catheter lumen, and the assembly may provide additional stiffening, rigidity or structural support for the catheter assembly when in the configuration illustrated in FIGS. 31-32.

Figure 36:
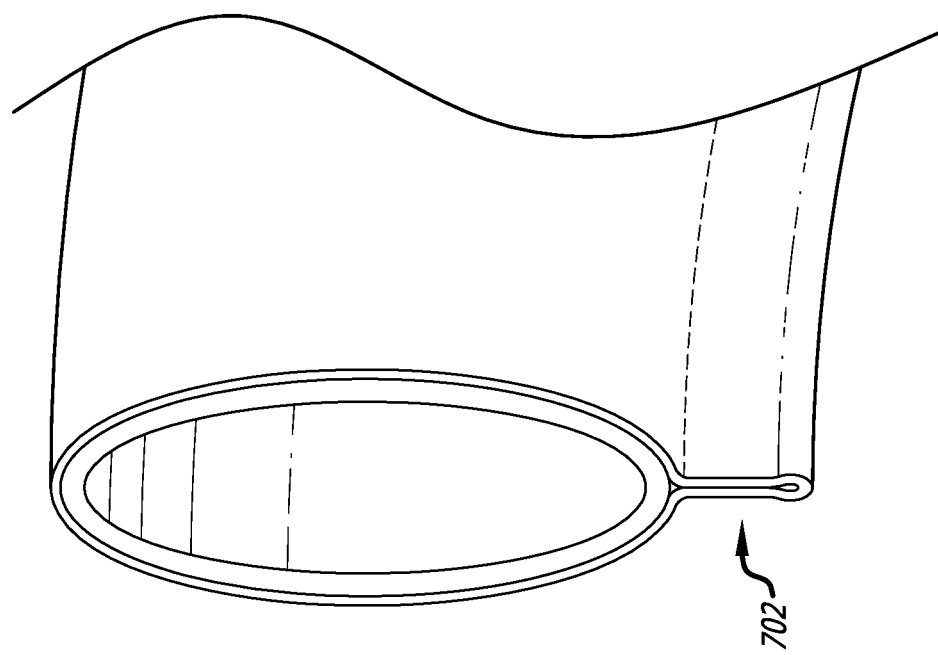
FIG. 36 is an isometric and transverse cross-sectional view similar to FIG. 34 wherein the inflation lumen is shown in a collapsed configuration with a pleat as represented in FIG. 35.
Figure 35:
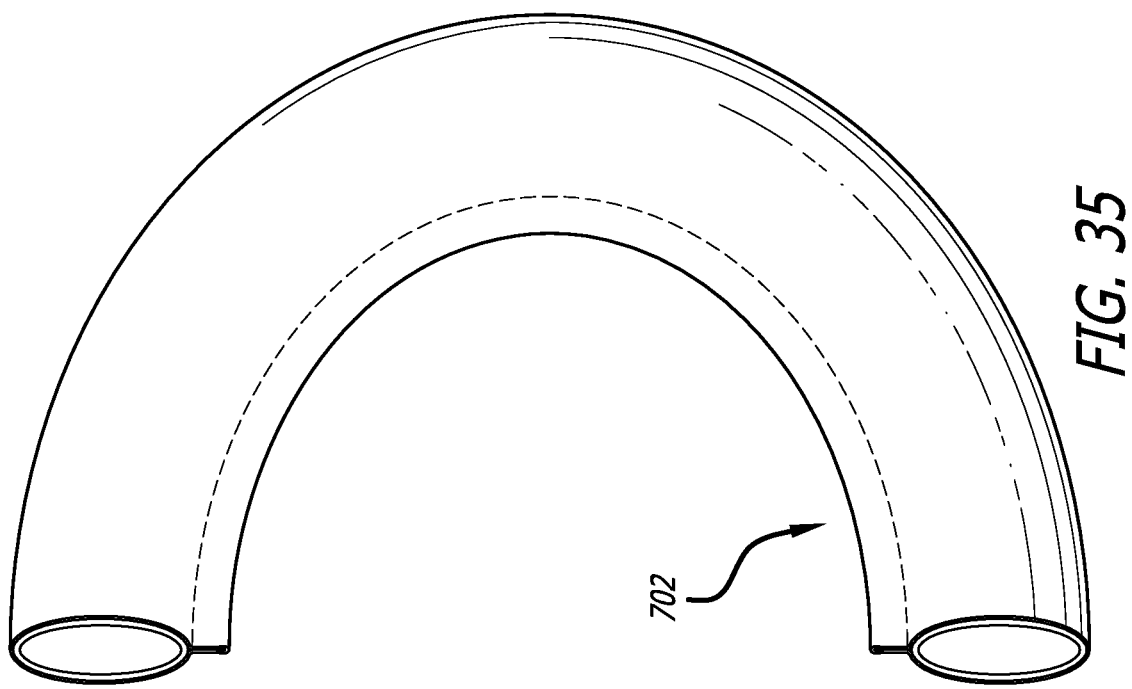
FIG. 35 is a plan view of the catheter assembly portion of FIG. 33 wherein the inflation lumen is shown in a collapsed configuration with a pleat over the adjacent portion of the catheter lumen.
Figure 43:
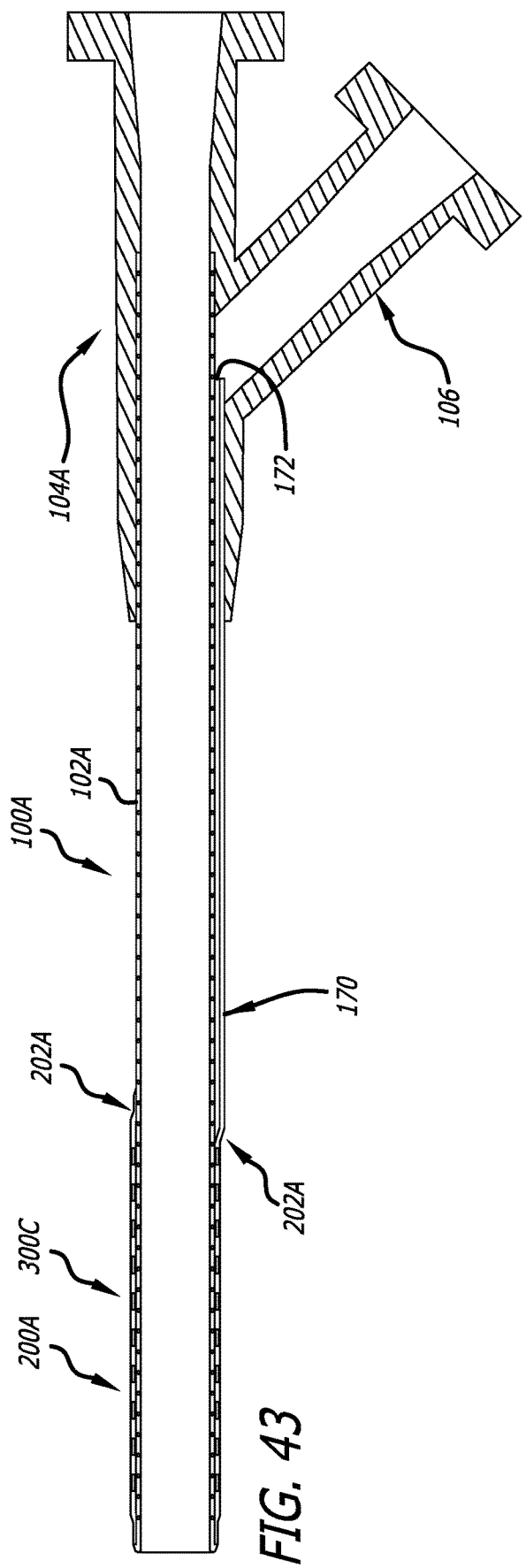
FIG. 43 is a view similar to that of FIG. 41 with the inflation lumen in a reduced, constricted or deflated configuration.
Figure 44:
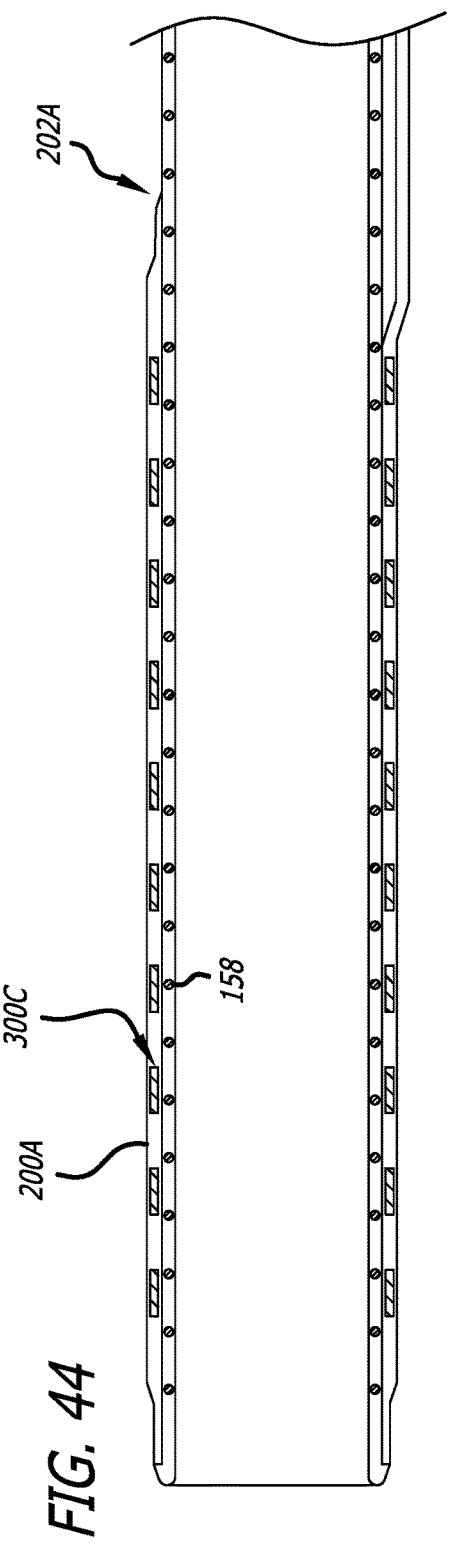
FIG. 44 is a detail of a distal portion of the catheter of FIG. 43.

In another configuration of a catheter assembly having controllably variable stiffness or rigidity in at least a portion of the catheter assembly, a portion of a catheter lumen 102A (FIGS. 33-36) may be enclosed in or surrounded by an inflation lumen or inflation balloon 700. The inflation lumen 700 may enclose only the adjacent portion of the catheter lumen, or may enclose the portion of the catheter lumen along with other structures and/or materials, including possible structures and/or materials between the inflation lumen 700 and the catheter lumen 102A. In the present illustrated example, the inflation lumen 700 surrounds the catheter lumen 102A without any intermediate structural material between the inflation lumen 700 and the catheter lumen 102A. in the present example, the inflation lumen 700 is formed from a relatively non-compliant material. When the inflation lumen 700 deflates or contracts inwardly around the catheter lumen 102A, for example to contact the catheter lumen, and for example with removal of inflation fluid or otherwise similar to methods described herein, one or more portions of the inflation lumen 700 form one or more pleats 702 (FIGS. 35-36). One or more pleats on the inflation lumen 700 provides structural support to the assembly. In the illustrated example, a pleat forms on the interior of a curved surface of the assembly, or on a concave surface of the assembly. In the configuration illustrated in FIGS. 35-36, the inflation lumen 700 has a deflated configuration where the lumen makes substantial contact with adjacent surfaces of the catheter lumen.

In another exemplary alternative illustrated in FIGS. 37-40, the assembly is identical to or substantially identical to that described with respect to FIGS. 29-32 but the medial member is omitting one or the other of the outer or inner structural support 352 (as illustrated) or 350, respectively. In an alternative configuration not illustrated, the structural support assembly can omit the inner structural support 350 and instead include the sleeve 354 and the outer structural support 352. Other configurations of a medial member of an assembly having a structural support member and a secondary material can be used.

In a further exemplary alternative illustrated in FIGS. 41-44, an assembly 100A includes an inflation lumen or balloon 200A incorporating with it a structural support material 300C. As illustrated, the structural support material 300C is embedded in or formed in part of the interior of the material of the inflation lumen 200A. In other configurations, the structural support material 300C may be formed on either or both of the interior or exterior surfaces of the inflation lumen 200A. In this example, the structural support material 300C may be any of the structural support elements described herein.

In any of the assemblies of the type described herein, and for any of the support members/structural supports or support structures described herein, the support structure can be made more or less amenable to easy movement within the assembly for example when an outer tubular element is in a relaxed state or otherwise pressing the support structure against the outer surface of the inner tubular structure 150, or otherwise when the support structure is contacting an outer surface of the inner tubular structure. To provide for easier movement, for example, steps can be taken to render the adjacent surfaces of the support structure smoother than otherwise, and/or change the structural configuration of the support structure, for example by decreasing the density of the limbs and/or their interconnection. In one example, easier movement can be accomplished by electro-polishing of a nytinol support structure.

In addition to other ways described herein, configurations of a support structure can also be used to contribute to higher frictional forces when in contact with one or more adjacent surfaces, including configurations described previously. In one example, a support structure may be configured so that one or more surfaces on the support structure facing respective adjacent structures on another part of the lumenal assembly have surface geometries that are other than smooth, or that are discontinuous, nonuniform or otherwise changed to be other than smooth. For example, the support structure has surfaces facing one or more of the adjacent structures, for example facing the tubular member 150 outer surface or facing the tubular element 200 inner surface, and such facing surfaces will have surface geometries. The relevant surface geometries of the structural support illustrated in FIGS. 12-13, for example, are substantially smooth. Alternatively, one or more of the surface geometries can be other than smooth, have discontinuities or non-uniformities. For example, a support structure may have an element such as a limb, or a plurality of limbs, that may be configured with a facing surface geometry that is non-smooth, for example to include one or more raised structures extending outwardly from one or more facing surfaces a desired distance so that the raised structure can contact a respective surface adjacent the facing surface for generating higher frictional force when they contact. In examples of the present assemblies, the adjacent surfaces can be adjacent surfaces on either or both of the outer tubular element or the inner tubular structure, or on intermediate or associated structures such as those described with respect to FIGS. 29-44.

Figure 45:
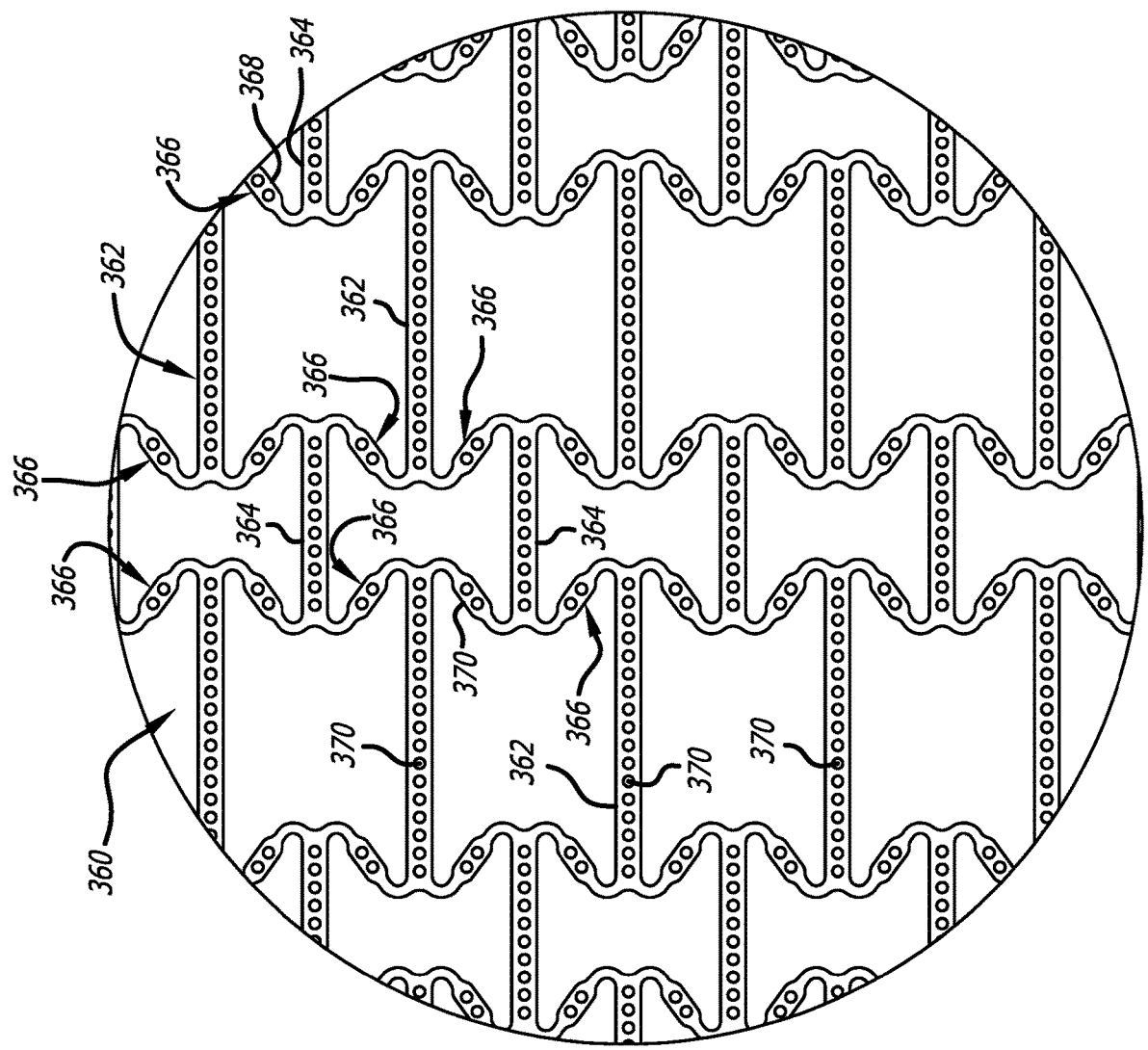
FIG. 45 is a schematic and plan view of a pattern for use as a structural support element for use with or as a medial member, for example in a catheter or similar assembly.
Figure 46:
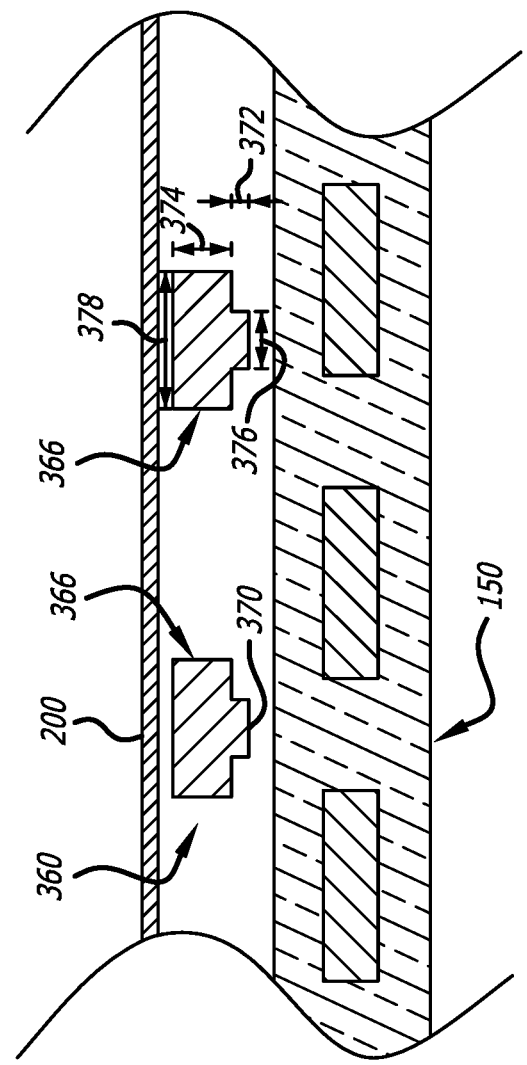
FIG. 46 is a detail and schematic and longitudinal cross section of a portion of a wall having an enlarged or inflated portion in an assembly analogous to the assembly illustrated in FIG. 6 showing the alternative structural support element of FIG. 45 for such an assembly.
Figure 47:
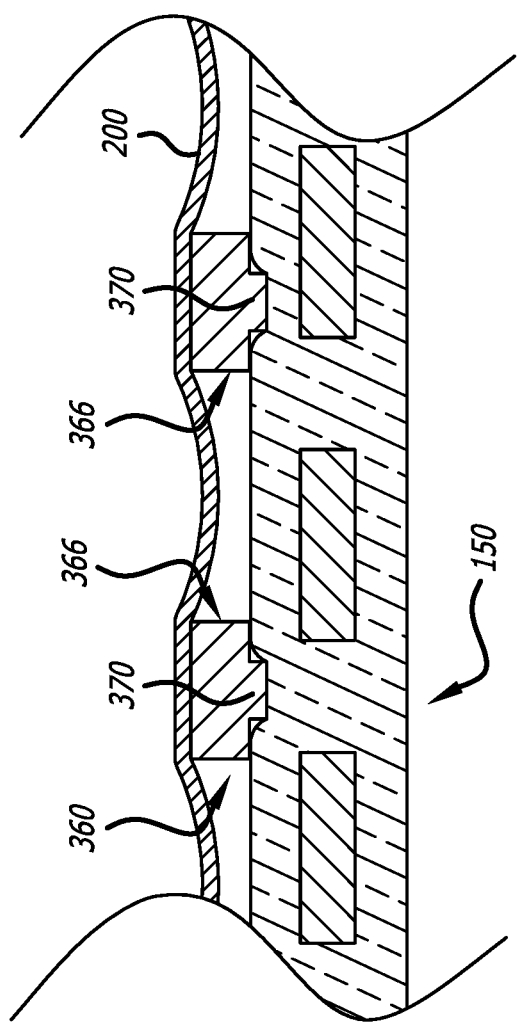
FIG. 47 is a detail and schematic and longitudinal cross section of the assembly of FIG. 46 analogous to the assembly illustrated in FIG. 4 showing the structural support element and outer tubular element collapsed or deflated with raised structures contacting an adjacent surface of a lumen structure.

An example of a support structure configuration that can contribute to higher frictional forces in the assembly for resisting movement or geometry changes with raised structures is a support structure 360 (FIGS. 45-47). In the present example, the support structure 360 is described as having raised structures on an interior facing surface to face an adjacent outside surface on the inner tubular structure 150, but it should be understood that raised structures can instead or additionally be placed on a facing surface facing an adjacent inside surface of the outer tubular element in the configuration shown in FIGS. 45-47. The present description has the raised structures for the support structure 360 on the inside surface of the support structure, but identical raised structures or different raised structures can be on the outside surface of the support structure.

The support structure 360 is similar to the support structure 300 in that it includes cells of limbs in the form of primary longitudinal struts 362 and secondary longitudinal struts 364 interconnected by serpentine struts 366, and the cells generally repeat. Other configurations are possible, and non-smooth surface geometries can be incorporated in any of the support structures as described herein or similar thereto. In the present configuration of the support structure 360, the primary longitudinal strut is less than twice the length of the secondary longitudinal strut but greater than 1½ times the length, as can be seen by the relative number of, substantially equally spaced in the illustrated example, raised structures on each of the longitudinal struts. Each primary longitudinal strut at each end is coupled to respective pairs of oppositely arranged serpentine struts 366. Each serpentine strut in the present example includes an enlarged portion 368 for providing a support for a raised structure. However, it is understood that fewer than all or that any number of struts can include raised structures, in any desired distribution, density, geometry and configuration, as desired, while the illustration shows all struts with raised structures, equally spaced, uniformly distributed, and with identical geometries.

In the example of the support structure 360 illustrated in FIGS. 45-47, each strut includes a raised structure 370. In the present example, each of the raised structures 370 are identical to the others, and are relatively evenly distributed across the longitudinal struts and across the enlarged portions 368 of the serpentine struts 266. In alternative configurations, the raised structures can be different from each other, and can be distributed unevenly or randomly, omitted from one or more limbs, or otherwise. One or more of the raised structures can be created according to a defined process at defined locations, according to a defined process at random locations, or according to a random process at random locations. In the present example, each of the raised structures 370 are identical to the extent that manufacturing or formation processes allow any predictable precision in the formation of the raised structures 370 or the support structure 360 having such raised structures. However, it is understood that conventional manufacturing processes may produce raised structures with variations in location on a strut, geometry and orientation, and the visual appearance of the geometry may be different from a drawing characterizing the structure or from which the structure was created by currently available forming techniques.

The raised structures can take a number of configurations. In the present example, they are illustrated as being substantially round having a relatively constant and consistent heights relative to each other and relative to the underlying strut. However, it should be understood that the actual resulting raised structures may not be identical in height or in cross-sectional configuration as between one another, or from one manufacturing lot to another. The raised structures are illustrated in the present example as being consistent in cross-section and also in height for simplicity. The geometries of the actual raised structures may vary. In one example of a configuration for the raised structures, the raised structure can have a height 372 less than a height or thickness 374 of the strut. If the raised structure 370 were configured to be round, the raised structure could have a diameter or equivalent dimension 376, which may be less than a width 378 of the strut from which the raised structure 370 extends. As illustrated, the ratio of the height of the raised structure is less than 50%, and the ratio of the diameter is also less than 50% of the width of the strut. These ratios may vary from about 10% to about 50%, respectively, with resulting variations in the frictional forces developed in the assembly for resisting movement or geometry changes in the assembly.

For a given assembly of a support structure and adjacent surfaces, the raised structures can decrease the surface area of contact between the struts and the adjacent surfaces, such as between the struts and the outer surface of the inner tubular element, relative to such an assembly without the raised structures. Decreasing the surface area of contact, such as by adding the raised structures, increases the force per unit area for a given configuration of the assembly in the area of the support structure, which produces an increase in the traction or frictional engagement between the support structure and the adjacent outer surface of the inner tubular element. For example, relative to comparable structures with the support structure 300 as illustrated in FIGS. 4 and 6, a support structure 360 having raised structures 370 will apply a higher force per unit area for each raised structure for a given outer tubular element 200. The higher force per unit area can occur when the outer tubular element is in its relaxed state or when the outer tubular element is contracted, such as when fluid is removed or pressure within the outer tubular element is reduced, for example so that the outer tubular element applies pressure to the structural support 360 squeezing it between the outer and inner tubular elements, and thereby changing the mechanical properties, stiffness and flexibility of that portion of the assembly. In the present example, the raised structures engage an outer surface on the inner tubular element 150. During the engagement, for example as illustrated in FIG. 47, the pressure applied to the struts 366 forces the raised structures 370 into the plastic surface of the inner tubular element 150. The raised structures engage the material creating frictional engagement, thereby changing the mechanical properties, stiffness or flexibility of that portion of the assembly. For a given pressure applied by the outer tubular element 200, the raised structures 370 produce a higher force per unit area against the outer surface of the inner tubular element 150.

Raised structures can be created on surfaces of the support structure according to a pattern, or randomly. They can be created as raised structures per se, or they can be produced by removing adjacent material, or they can be generated as a combination of raised and depressed areas or cavities. Raised structures can be formed in a number of ways. In one process, raised structures can be photochemically milled during the formation of a stent or stent-like structure, such as any of the support structures of the type described herein, and the support structure formed accordingly. For example, raised structures can be formed on a planar stent pattern and then rolled to form the final support structure, with the raised structures on the interior surface, exterior surface, or possibly both depending on the desired method of formation. In another process of forming raised structures on a support structure, the support structure can be created as desired, and then covered with a photomask or photoresist, which can then be used to create a random or non-keyed pattern of raised structures.

In another example of lumenal or tubular structures, including any of those described herein, a surface of an inner tubular structure facing an adjacent surface of a support structure such as any of those described herein can be formed other than entirely smooth, for example with surface roughness different than the surface configuration of other parts of the inner tubular structure, surface dimples, surface cavities or other surface discontinuities. The facing surface of the inner tubular structure can be other than entirely smooth to increase the frictional engagement between the surface and the adjacent support structure.

In any of the lumenal members described herein, including for example the catheter assembly 100, and 100A, the lumenal members may include one or more medical devices associated with the assembly, for example adjacent the distal portion of the assembly. In one example (FIG. 48), a catheter assembly 100B is identical to the catheter assembly 100A, and has the same structures and functions as described with respect to catheter 100A, for example as described in conjunction with FIGS. 8-9, with the addition of one or more medical devices. In the illustrated example, medical device 750 is positioned on an external surface of the catheter shaft 102A, for example as illustrated over and contacting the seam or seal between the catheter shaft and the inflation lumen. Alternatively, the medical device 750 can be mounted on or supported by a portion of the catheter shaft (not shown) extending distally of the seam or seal. The medical device can be configured to extend around the catheter shaft, or may be configured to extend over an arcuate portion of the shaft. The medical device can extend longitudinally and radially as desired for the intended purpose of the device.

Figure 48:
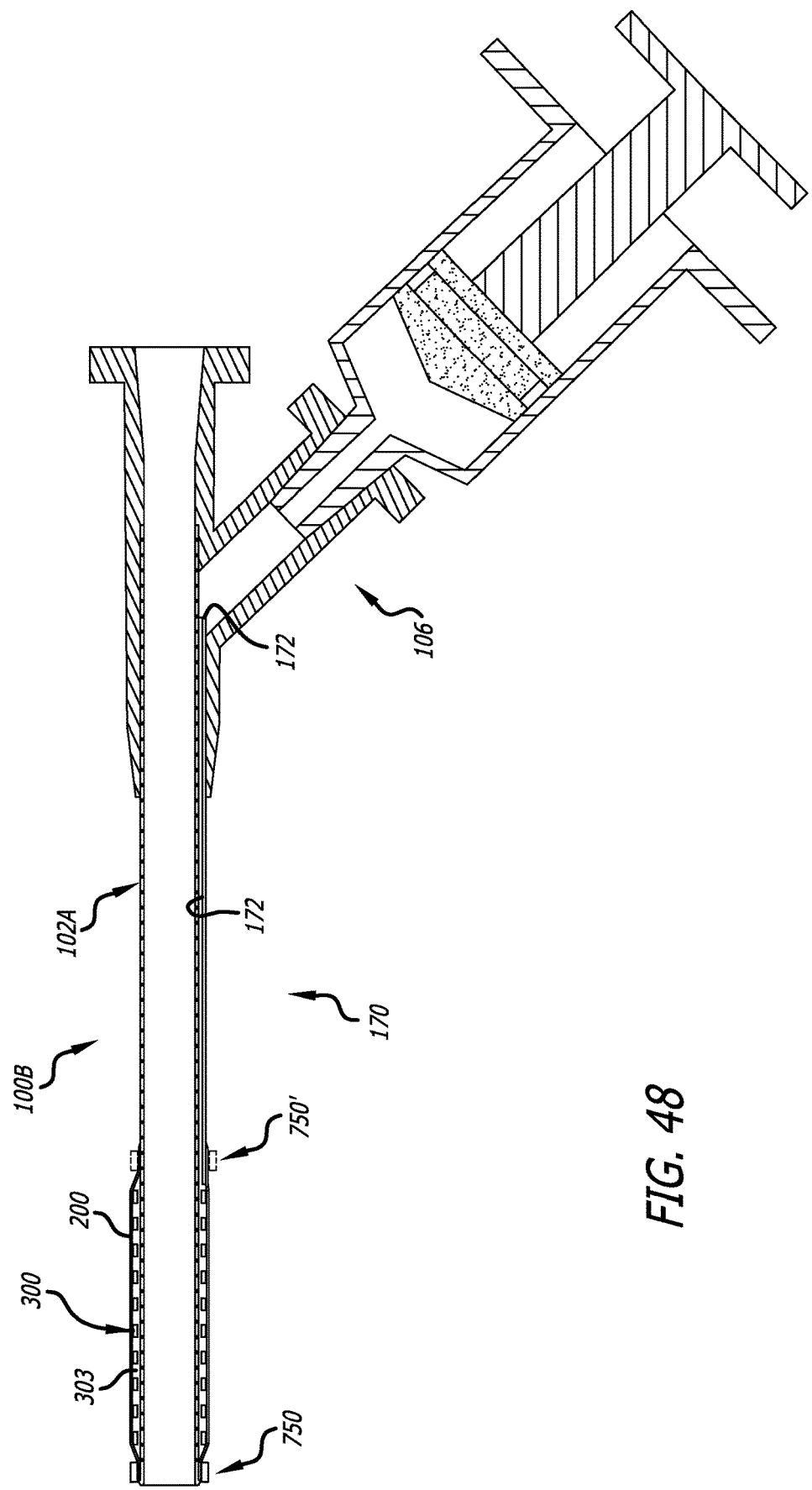
FIG. 48 is a longitudinal cross section of a catheter assembly similar to that shown in FIGS. 8-9 with a medical device in the form of a diagnostic or therapy device associated with the catheter.

In a further configuration of the assembly 100B is illustrated in FIG. 48, the medical device 750 alternatively or additionally can be supported adjacent a distal portion of the catheter shaft 102A, as illustrated at 750'. The characteristics and configuration of the medical device 750' can be the same as or different from the medical device located distally of the inflation lumen.

The medical device 750/750' can be any number of devices. The medical device can be any one or more of a diagnostic or therapy device, including but not limited a device for angioplasty, ablation, angiography, occlusion, radiation, visualization, or a stent.

Having thus described several exemplary implementations, it will be apparent that various alterations and modifications can be made without departing from the concepts discussed herein. Such alterations and modifications, though not expressly described above, are nonetheless intended and implied to be within the spirit and scope of the inventions. Accordingly, the foregoing description is intended to be illustrative only.

What is claimed is:
1. An apparatus comprising a catheter assembly configured for transiting a body lumen, the catheter assembly comprising:
   a lumenal element extending longitudinally,
   a structural support extending longitudinally and about a portion of the lumenal element and including a plurality of limbs with integral raised structures on a facing surface of the structural support facing the lumenal element, and a tubular element sealed at least in part to the lumenal element and extending on a side of the structural support outside of the lumenal element and configured such that the tubular element contacts at least a portion of the structural support to provide a first stiffness for the lumenal element adjacent the structural support and such that the lumenal element has a second stiffness lower than the first stiffness when contact between the tubular element and the at least a portion of the structural support is decreased.

2. The apparatus of claim 1 wherein the raised structures are distributed substantially uniformly.

3. The apparatus of claim 1 wherein the raised structures have similar geometries.

4. The apparatus of claim 1 wherein the raised structures extends from a respective surface and wherein the raised structures have heights extending from the respective facing surface that are similar to each other.

5. The apparatus of claim 1 wherein a plurality of the raised structures have a non-circular geometry in plan view.

6. The apparatus of claim 1 wherein the structural support includes a material having a thickness and wherein at least one of the raised structures has a height that is less than a thickness of the material from which the at least one raised structure extends.

7. The apparatus of claim 1 wherein the structural support includes a material and wherein at least one of the raised structures is substantially centered widthwise relative to the material from which the at least one raised structure extends.

8. The apparatus of claim 1 wherein the tubular element is configured to releasably compress the structural support.

9. The apparatus of claim 1 wherein the structural support is a tubular structural support.

10. The apparatus of claim 1 wherein the structural support is a tubular mesh.

11. The apparatus of claim 10 wherein the tubular mesh includes a non-random tubular mesh.

12. The apparatus of claim 1 wherein the structural support is positioned in a cavity between the lumenal element and the tubular element.

13. The apparatus of claim 1 wherein the tubular element substantially encloses the structural support.

14. The apparatus of claim 1 further including a passageway for fluid to enter and exit an area between the structural support and the tubular element.

15. The apparatus of claim 1 wherein the tubular element is flexible.

16. The apparatus of claim 1 wherein the tubular element is resiliently flexible.

17. The apparatus of claim 1 wherein the tubular element is a balloon.

18. The apparatus of claim 1 wherein the tubular element is configured to have an enlarged configuration and a reduced configuration, and wherein in the reduced configuration the tubular element applies pressure to at least a portion of the structural support.

19. The apparatus of claim 18 wherein the structural support is sandwiched, concentric, layered, or positioned between the lumenal element and the tubular element.

20. The apparatus of claim 18 wherein the apparatus is configured such that application of pressure by the tubular element to the structural support presses the structural support against the lumenal element.

21. The apparatus of claim 18 wherein the apparatus is configured such that enlargement of the tubular element relieves at least part of the pressure on the structural support.

22. The apparatus of claim 21 wherein the apparatus is configured such that enlargement of the tubular element relieves all of the pressure on the structural support.

23. The apparatus of claim 21 wherein the apparatus is configured such that relieving pressure on the structural support includes reducing a surface area of contact between the tubular element and the structural support.

24. The apparatus of claim 1 wherein the structural support comprises a plurality of component elements and wherein a transverse cross-section of the structural support includes at least two component elements.

25. The apparatus of claim 24 wherein the transverse cross-section of the structural support includes at least three component elements.

26. The apparatus of claim 24 wherein at least two of the component elements have different sizes.

27. The apparatus of claim 24 wherein at least two of the component elements have different transverse cross-sectional areas.

28. The apparatus of claim 24 wherein at least two of the component elements have different lengths.

29. The apparatus of claim 24 wherein the structural support comprises at least first and second groups of component elements wherein each of the component elements in the first group is different from each of the component elements in the second group.

30. The apparatus of claim 29 wherein there are more component elements in the second group than in the first group.

31. The apparatus of claim 29 wherein there are twice as many component elements in the second group than in the first group.

32. The apparatus of claim 29 wherein respective ones of the component elements in the first group are coupled to respective ones of the component elements in the second group.

33. The apparatus of claim 24 wherein the at least two component elements are connected to each other.

34. The apparatus of claim 24 wherein the at least two component elements are connected to each other at respective ends.

35. The apparatus of claim 24 wherein the at least two component elements include at least one smooth surface.

36. The apparatus of claim 24 wherein the structural support extends longitudinally a first distance, and wherein one of the component elements includes a component element less than the first distance.

37. The apparatus of claim 36 wherein each of the component elements in the structural support includes respective lengths less than the first distance.

38. The apparatus of claim 24 wherein the structural support includes at least three component elements having a first transverse cross-sectional area, and at least three components having a second transverse cross-sectional area less than the first transverse cross-sectional area.

39. The apparatus of claim 24 wherein the component elements are distributed around a perimeter of the structural support substantially uniformly.

40. The apparatus of claim 24 wherein each of the component elements is coupled to at least one other component element.

41. The apparatus of claim 40 wherein each of the component elements is coupled at each end respectively to at least one other component element.

42. The apparatus of claim 24 wherein each of the component elements extends substantially linearly.

43. The apparatus of claim 24 wherein the at least two component elements includes first and second component elements and wherein the first and second component elements are coupled to each other at an angle.

44. The apparatus of claim 43 wherein the angle is greater than zero and less than 90°.

45. The apparatus of claim 1 wherein the lumenal element includes a reinforcement.

46. The apparatus of claim 45 wherein the reinforcement includes either a coil or a braid embedded in the lumenal element.

47. The apparatus of claim 1 wherein the lumenal element is substantially incompressible under normal operating conditions.

48. The apparatus of claim 1 wherein the structural support is a stent.

49. The apparatus of claim 1 further including a catheter hub having an injection port.

50. The apparatus of claim 1 further including a fluid lumen coupled to a space between the tubular element and the structural support, and extending off-center from a central axis of the assembly.

51. The apparatus of claim 50 wherein the fluid lumen extends along an outside wall of the lumenal element.

52. The apparatus of claim 1 wherein the catheter assembly is configured to receive a guidewire.

53. The apparatus of claim 1 wherein the catheter assembly is configured to receive a dilator element or therapy device.

54. The apparatus of claim 1 wherein the catheter assembly is configured to receive a syringe.

55. The apparatus of claim 1 wherein the tubular element is configured to be biased for pressing against the structural support.

56. The apparatus of claim 1 wherein the tubular element is sufficiently flexible to have surface portions extend between individual components of the structural support.

57. The apparatus of claim 1 wherein the structural support is configured in the catheter assembly to have an inside diameter substantially the same as an outside diameter of the adjacent lumenal element.

58. The apparatus of claim 1 wherein the plurality of limbs are arranged circumferentially around the structural support.

59. The apparatus of claim 58 wherein the plurality of limbs comprises at least three longitudinally extending elements.

60. The apparatus of claim 58 wherein the plurality of limbs includes six longitudinally extending elements.

61. The apparatus of claim 1 wherein the structural support comprises a second plurality of limbs extending at an acute angle to respective ones of the plurality of limbs.

62. The apparatus of claim 61 wherein the second plurality of limbs includes raised portions.

63. The apparatus of claim 62 wherein each of the limbs in the second plurality of limbs extending at an acute angle includes respective first and second ends and wherein each first and second end is connected to a respective longitudinally extending limb.

64. The apparatus of claim 62 wherein the limbs in the plurality of limbs have a size different from a size of the limbs in the second plurality of limbs.

65. The apparatus of claim 64 wherein the longitudinally extending limbs have at least one of a larger transverse cross-sectional area or longer length.

66. The apparatus of claim 62 wherein the limbs in the second plurality of limbs extend at an angle to respective ones of longitudinally extending limbs greater than zero and less than 90°.

67. The apparatus of claim 66 wherein the angle is between 5° and 30°.

68. The apparatus of claim 1 wherein a second plurality of limbs are arranged circumferentially around the structural support and shifted longitudinally from the plurality of limbs.

* * * * *